US006458758B1

United States Patent
Hsia

(10) Patent No.: US 6,458,758 B1
(45) Date of Patent: *Oct. 1, 2002

(54) COMPOSITIONS AND METHODS UTILIZING NITROXIDES IN COMBINATION WITH BIOCOMPATIBLE MACROMOLECULES

(75) Inventor: Jen-Chang Hsia, Irvine, CA (US)

(73) Assignee: Synzyme Technologies, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/824,739

(22) Filed: Mar. 26, 1997

Related U.S. Application Data

(63) Continuation-in-part of application No. 08/605,531, filed on Feb. 22, 1996, now Pat. No. 5,840,701, which is a continuation-in-part of application No. 08/482,952, filed on Jun. 7, 1995, now abandoned, which is a continuation-in-part of application No. 08/417,132, filed on Mar. 31, 1995, now Pat. No. 5,767,089, which is a continuation-in-part of application No. 08/291,590, filed on Aug. 15, 1994, now Pat. No. 5,591,710, which is a continuation-in-part of application No. 08/107,543, filed on Aug. 16, 1993, now abandoned.

(30) Foreign Application Priority Data

Oct. 3, 1996 (WO) ................................ PCT/US96/03644

(51) Int. Cl.[7] ......................... A61K 38/38; A61K 38/42

(52) U.S. Cl. ................................ 514/2; 514/6; 514/277; 514/315; 514/579; 530/362; 530/385; 544/184; 544/216; 548/401; 548/541

(58) Field of Search ................................ 514/2, 6, 277, 514/315, 579; 530/362, 385; 544/184, 216; 548/401, 541

(56) References Cited

U.S. PATENT DOCUMENTS

| 4,529,719 A | * | 7/1985 | Tye et al. | ................ 514/6 |
| 5,804,561 A | * | 9/1998 | Hsia | ................ 514/21 |
| 5,840,701 A | * | 11/1998 | Hsia | ................ 514/21 |

FOREIGN PATENT DOCUMENTS

| WO | WO 88/05044 | * | 7/1988 |

OTHER PUBLICATIONS

Samuni et al. 'Nitroxide Stable Radical Protect Beating Cardiomyocytes Against Oxidative Damage', Journal of Clinical Investigation, vol. 87, pp. 1526–1530, May 1991.*

* cited by examiner

*Primary Examiner*—Christopher S. F. Low
*Assistant Examiner*—Anish Gupta
(74) *Attorney, Agent, or Firm*—Lyon & Lyon LLP

(57) ABSTRACT

Compositions and processes to alleviate free radical toxicity are disclosed based on the use of nitroxides in association with physiologically compatible macromolecules. In particular, hemoglobin-based red cell substitutes are described featuring stable nitroxide free radicals for use in cell-free hemoglobin solutions, encapsulated hemoglobin solutions, stabilized hemoglobin solutions, polymerized hemoglobin solutions, conjugated hemoglobin solutions, nitroxide-labelled albumin, and nitroxide-labelled immunoglobulin. Formulations are described herein that interact with free radicals, acting as antioxidant enzyme-mimics, which preserve nitroxides in their active form in vivo. Applications are described including blood substitutes, radioprotective agents, imaging agents, agents to protect against ischemia and reperfusion injury, particularly in cerebral ischemia in stroke, and in vivo enzyme mimics among others.

2 Claims, 44 Drawing Sheets

(7 of 44 Drawing Sheet(s) Filed in Color)

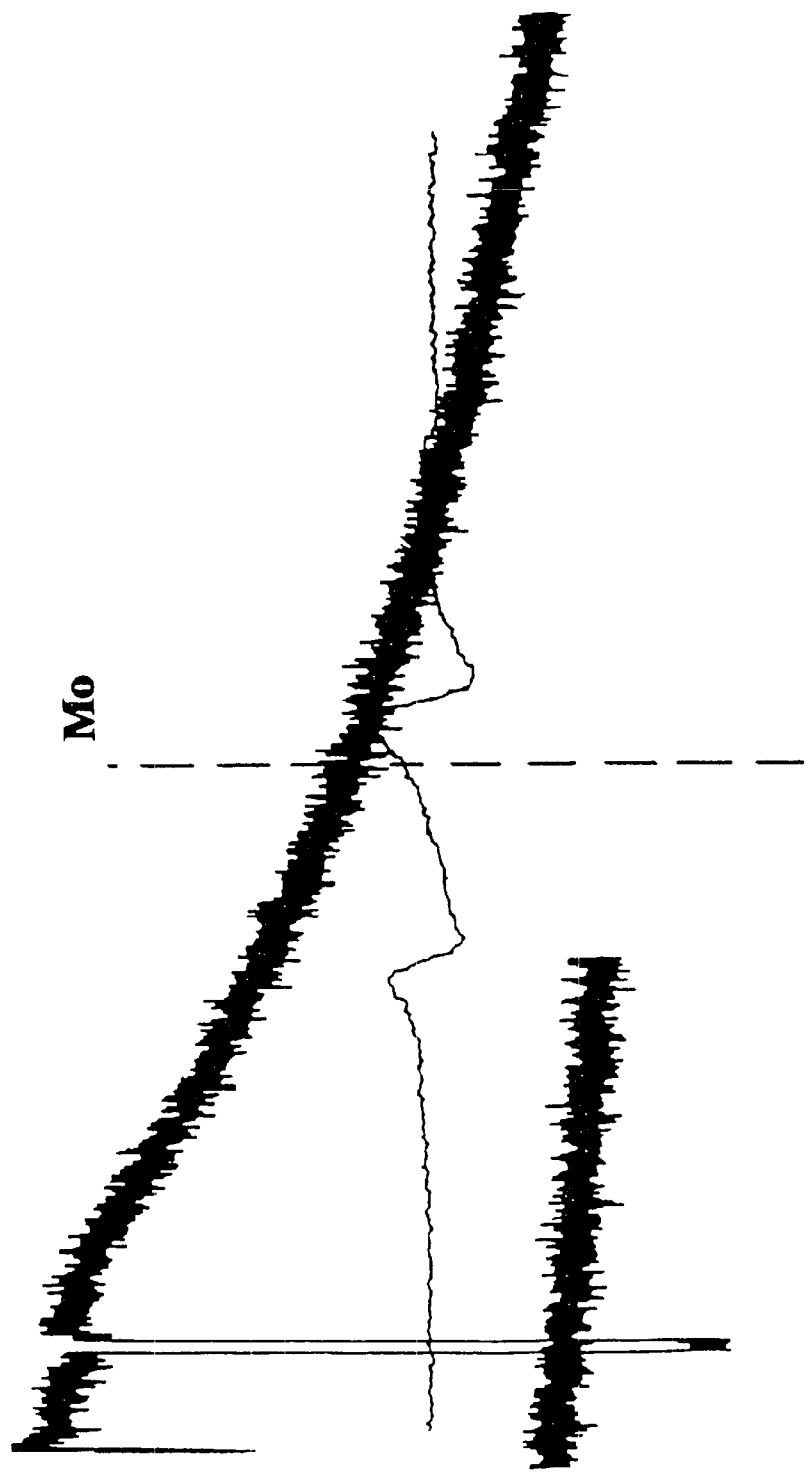

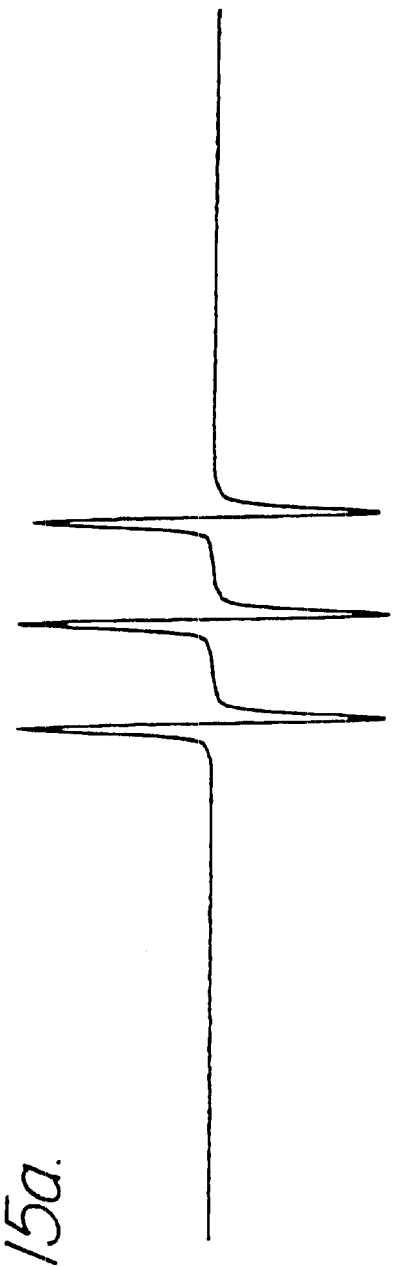
FIG. 15a.
FIG. 15b.
FIG. 15c.

Full view    Cutout view

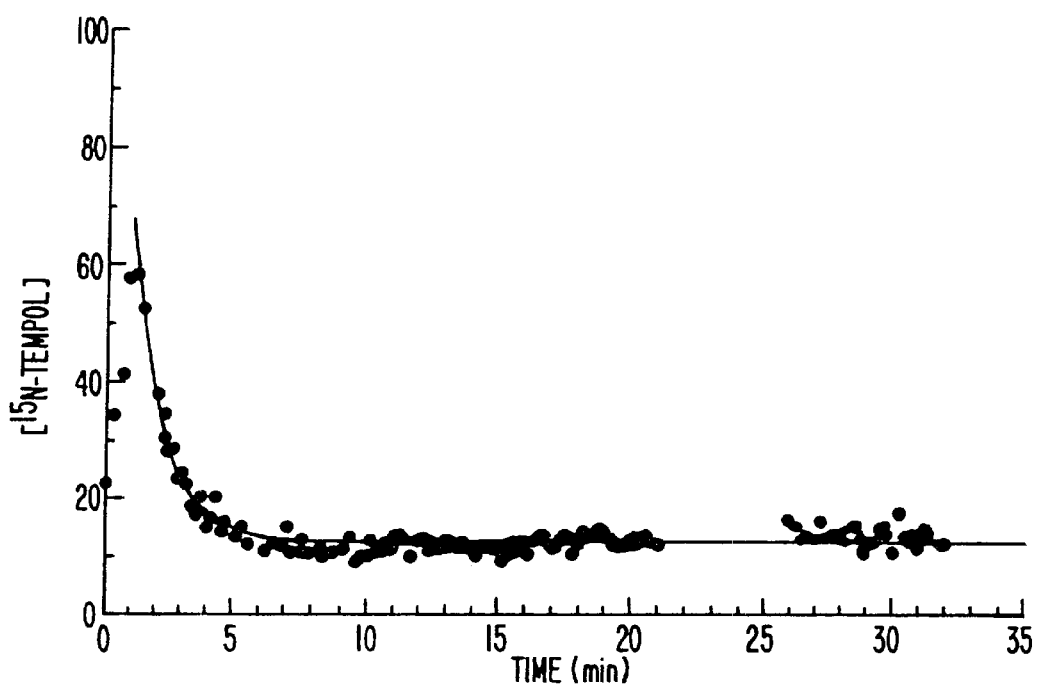
FIG. 41.
FIG. 42a.
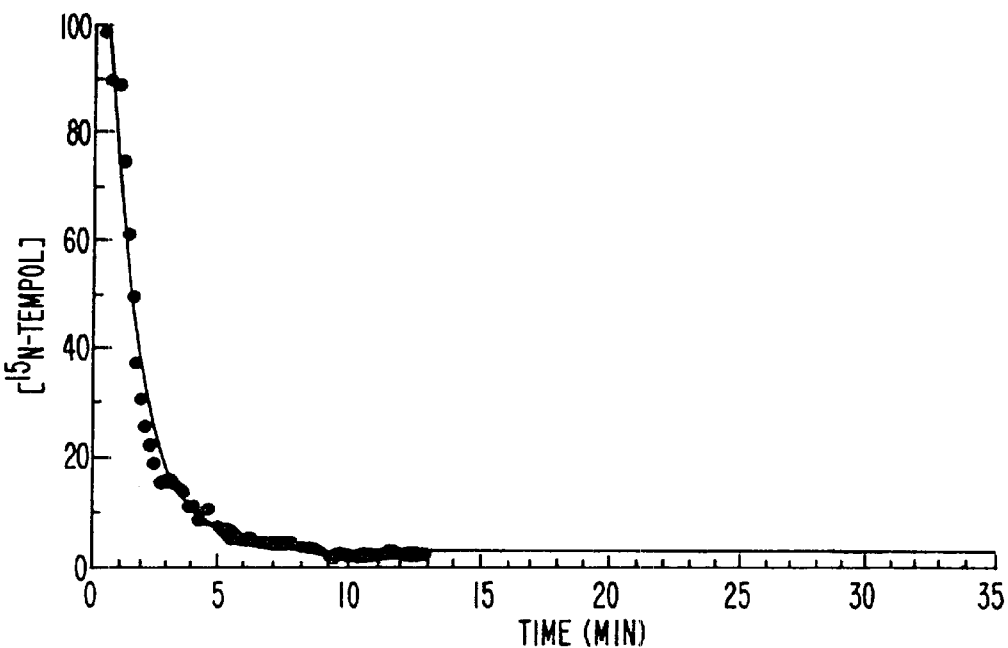

COMPOSITIONS AND METHODS UTILIZING NITROXIDES IN COMBINATION WITH BIOCOMPATIBLE MACROMOLECULES

This application is a continuation-in-part of application Ser. No. 08/605,531 filed Feb. 22, 1996 and now U.S. Pat. No. 5,840,701, which is a continuation-in-part of application Ser. No. 08/482,952 filed Jun. 7, 1995 and now abandoned, which is a continuation-in-part of application Ser. No. 08/417,132 filed Mar. 31, 1995 and now U.S. Pat. No. 5,767,089, which is a continuation-in-part of application Ser. No. 08/291,590 filed Aug. 15, 1994 and now U.S. Pat. No. 5,591,710, which is a continuation-in-part of application Ser. No. 08/107,543 filed Aug. 16, 1993 and now abandoned, and incorporates each by reference.

FIELD OF THE INVENTION

This invention relates to the therapeutic and diagnostic use of nitroxides, including the combined use of a membrane permeable nitroxide with a membrane impermeable nitroxide including nitroxide-labelled macromolecules, including polypeptides e.g., hemoglobin, albumin, immunoglobulins, and polysaccharides, e.g., dextran, hydroxylethyl starch, and artificial membranes, e.g., liquid bilayer, hemoglobin and albumin microbubbles. Nitroxide-containing formulations are disclosed which alleviate the toxic effects of oxygen-related species in a living organism and provide ability to diagnose and treat a wide variety of pathological physiological conditions. This invention also relates to nitroxides, synthetic nitroxide polymers and copolymers and nitroxide-labelled macromolecules used in combination with low molecular weight and membrane-permeable nitroxides to sustain the in vivo effect of nitroxides. This invention also discloses novel compounds and methods featuring nitroxides used in combination with physiologically compatible cell-free and encapsulated hemoglobin solutions for use as a red cell substitute. Furthermore, this invention describes the methods and novel compounds for the topical delivery of cell membrane impermeable nitroxides in its membrane permeable form leading to intracellular accumulation of therapeutic concentrations of the said nitroxide for treatment of skin photo aging and as an anti-skin wrinkle agent. Additionally, this invention describes the above nitroxides in combination with other physiologically active compounds, including other nitroxides, to protect from pathological damage and oxidative stress caused by free radicals and describes their use in diagnosis and in the treatment of disease.

BACKGROUND OF THE INVENTION

Although the physiological mechanisms of oxygen metabolism have been known for many years, the role played by oxidative stress in physiology and medicine is not completely understood. The impact of oxygen-derived free radicals on physiology and disease is a topic of increasing importance in medicine and biology. It is known that disease and injury can lead to levels of free radicals which far exceed the body's natural antioxidant capacity—the result is oxidative stress. Oxidative stress is the physiological manifestation of uncontrolled free radical toxicity, most notably that which results from toxic oxygen-related species. Toxic free radicals are implicated as a causative factor in many pathologic states, including ischemia-reperfusion injury resulting from heart attack or stroke, shock, alopecia, sepsis, apoptosis, certain drug toxicities, toxicities resulting from oxygen therapy in the treatment of pulmonary disease, clinical or accidental exposure to ionizing radiation, trauma, closed head injury, burns, psoriasis, in the aging process, and many others.

Therefore, a need exists for compositions and methods which detoxify free radicals and related toxic species and which are sufficiently active and persistent in the body to avoid being rapidly consumed when increases in free radical concentrations are encountered.

Furthermore, evidence has been developed which demonstrates that free radicals aggravate a number of other disease states including cancer, ulcers and other gastrointestinal conditions, cataracts, closed head injury, renal failure, injury to the nervous system, and cardiovascular disease to name a few. As a result of their high reactivity, free radicals can oxidize nucleic acids, biological membranes, and other cell components, resulting in severe or lethal cellular damage, mutagenesis, or carcinogenesis. Anti-cancer radiotherapy, as well as a number of antitumor drugs, act by generating free radicals which are toxic to tumor cells, but are also toxic to normal cells which are exposed during cell division causing the undesirable side-effects of cancer therapy. Indeed, it is believed that many pathologic processes have as their common final pathway the generation of free radicals which are the direct, or a substantial contributing cause, of the observed pathology. Additionally, a dramatic increase in free radical concentrations can be observed as part of a cascade initiated by the interruption of the flow of oxygenated blood, such as in heart attack or stroke, often followed by the reperfusion of oxygenated blood to the affected area. As the importance of such oxidative stress in living systems becomes appreciated, a continuing need exists for compounds and methods that can function as anti-oxidants and which can be designed to interact with oxygen-derived free radicals to alleviate their toxicity in biological systems, particularly in humans. In other applications, the toxic free radicals may be coincident to a beneficial treatment such as radiation administered as part of cancer radiotherapy. For example, since the mechanism by which ionizing radiation causes physiologic damage to an organism involves, at least in part, a free radical interaction with cells, compounds which possess or interact with free radicals exhibit a localized effect on tissues exposed to radiation therapy thereby controlling the collateral damage caused by a therapeutic treatment. Additionally, apart from any clinically significant function, since the unpaired electrons in free radicals species are detectable by spectroscopy, free radical reactions may be monitored in vivo and compounds which interact with free radicals are observable by spectroscopic techniques.

Several therapeutic approaches have been proposed to reduce pathologic levels of free radicals. Ideally, safe and effective antioxidant agents would augment a patient's antioxidant capacity and assist in blocking many pathologic free-radical based toxicities at the stage of free radical generation. However, the development of methods and compounds to combat oxidative stress or the toxicity associated with oxygen-related species has enjoyed limited success. The usefulness of many anti-oxidants is limited by short duration of action in vivo, toxicity at effective dosage levels, the inability of many compounds to cross cell membranes, and an inability to counter the effects of high levels of free radicals. For example, the administration of the enzyme superoxide dismutase (SOD) or catalase can promote the conversion of toxic free radical related species to a non-toxic form. However, these enzymes do not function effectively in the intracellular space. Procysteine as a GSH precursor, as well as vitamins and other antioxidant chemicals, can enhance the body's natural antioxidant capacity, but are unable to deal with the higher levels of free radicals encountered in injury and disease and are rapidly consumed by the body.

Free radical species are notoriously reactive and short-lived. Such reactivity is a particularly serious hazard in biological systems because detrimental chemical reactions between a free radical and body tissue occurs in very close proximity to the site where the free radial is generated. Therefore, compounds which inherently function to reduce free radical concentrations have some beneficial effect, although the effect may not be clinically significant unless the therapeutic effect can be concentrated and localized in a particular region of the body such as the brain, the epidermis, the gut, the cardiovascular system or in discrete tissue such as the site of radiation administration.

The difficulties encountered in creating a blood substitute suitable for large volume intravenous administration are an acute example of the difficulty in preventing or alleviating systemic toxicity caused by oxygen-related species in the vascular space. Scientists and physicians have struggled for decades to produce a blood substitute that could be safely transfused into humans. Persistent blood shortages and the problems of incompatible blood types, cross-matching, and the communication of disease have led to a broad-based effort by private industry, universities, and governments to discover a formulation that would allow a large volume of a blood substitute to be safely transfused without significant physiological side effects. At present, several companies are conducting clinical trials on experimental blood substitutes. However, adverse physiological reactions and the inherent complexity of the research and development process have impeded progress through the regulatory approval stages and have impeded the development of a clinically useful blood substitute.

A Research Advisory Committee of the United States Navy issued a report in August 1992 outlining the efforts by several groups to produce a blood substitute, assessing the status of those efforts, and generally describing the toxicity problems encountered. The Naval Research Advisory Committee Report reflects the current consensus in the scientific community that even though the existing blood substitute products, often termed "hemoglobin-based oxygen carriers" (HBOC), have demonstrated efficacy in oxygen transport, certain toxicity issues are unresolved. The adverse transfusion reactions that have been observed in clinical studies of existing hemoglobin-based oxygen carriers (HBOC) include systemic hypertension and vasoconstriction. These adverse reactions have forced a number of pharmaceutical companies to abandon their clinical trials or to proceed at low dosage levels.

Solving the toxicity problem in the existing hemoglobin-based blood substitutes has been given a high priority by the United States Government. A Naval Research Committee recommendation has been implemented by the National Institute of Health in the form of a Request For Proposal (PA-93-23) on the subject of "Hemoglobin-Based Oxygen Carriers: Mechanism of Toxicity." Therefore, the medical and scientific community suffers from an acute and pressing need for a blood substitute that may be infused without the side effects observed with the existing hemoglobin-based oxygen carriers.

The red blood cells are the major component of blood and contain the body's oxygen transport system. It has long been recognized that the most important characteristic of a blood substitute is the ability to carry oxygen. The red blood cells are able to carry oxygen because the primary component of the red cells is hemoglobin, which functions as the oxygen carrier. Most of the products undergoing clinical testing as blood substitutes contain hemoglobin that has been separated from the red blood cell membranes and the remaining constituents of the red blood cells and has been purified to remove essentially all contaminants. However, when hemoglobin is removed from the red cells and placed in solution in its native form, it is unstable and rapidly dissociates into its constituent subunits. For this reason, the hemoglobin used in a hemoglobin-based oxygen carrier (HBOC) must be stabilized to prevent dissociation in solution. Substantial expenditures in scientific labor and capital were necessary to develop hemoglobin-based products that are stable in solution, and which are stabilized in such a way that the oxygen transport function is not impaired. The ability of the existing hemoglobin-based oxygen carriers to transport oxygen has been well established (See U.S. Pat. Nos. 3,925,344; 4,001,200; 4,001,401; 4,053,590; 4,061,736; 4,136,093; 4,301,144; 4,336,248; 4,376,095; 4,377,512; 4,401,652; 4,473,494; 4,473,496; 4,600,531; 4,584,130; 4,857,636; 4,826,811; 4,911,929 and 5,061,688).

In the body, hemoglobin in the red cells binds oxygen molecules as the blood passes through the lungs and delivers the oxygen molecules throughout the body to meet the demands of the body's normal metabolic function. However, the atmospheric oxygen that most living beings must breathe to survive is a scientific and medical paradox. On the one hand, almost all living organisms require oxygen for life. On the other hand, a variety of toxic oxygen-related chemical species are produced during normal oxygen metabolism.

With respect to oxidative stress resulting from the transportation of oxygen by hemoglobin, it is known that in the process of transporting oxygen, the hemoglobin (Hb) molecule can itself be oxidized by the oxygen ($O_2$) molecule it is carrying. This auto-oxidation reaction produces two undesirable products: met-hemoglobin (met-Hb) and the superoxide anion ($.O_2^-$). The chemical reaction may be written as follows:

$$Hb + 4O_2 \rightarrow met\text{-}Hb + 4.O_2^- \quad [1]$$

The superoxide anion ($.O_2^-$) is an oxygen molecule that carries an additional electron and a negative charge. The superoxide anion is highly reactive and toxic.

As described in detail herein, free radical species such as the superoxide anion are implicated as the agents of cell damage in a wide range of pathological processes. In the case of oxygen transport by hemoglobin, potentially damaging oxidative stress is manifested in the vascular space and originates with the superoxide anion being generated by the auto-oxidation of hemoglobin and results from the subsequent conversion of the superoxide anion to toxic hydrogen peroxide in the presence of the enzyme superoxide dismutase (SOD) by the following reaction:

$$2 \cdot O_2^- + 2H^+ \xrightarrow{SOD} 2 O_2 + H_2O_2 \quad [2]$$

The reaction whereby a free radical species generates toxic chemical species in vivo or causes cellular damage is seen repeatedly in pathologic conditions where oxidative stress is a factor, particularly in the instance of ischemic reperfusion injury as in heart attack or stroke. The presence of the superoxide anion and hydrogen peroxide in the red blood cells is believed to be the major source of oxidative stress to the red cells.

Apart from oxygen transport by the hemoglobin contained therein, a less recognized characteristic of the red cells is that they contain a specific set of enzymes which are capable of detoxifying oxygen-related chemical species produced as by-products of oxygen metabolism. Without the protection of these specific enzyme systems, autoxidation of hemoglobin would lead to deterioration and destruction of the red cells. In the body, however, the reserve capacity of the enzyme systems in the red cells protects the body from oxygen toxicity by converting the superoxide anion generated during normal metabolism to non-toxic species and thereby controls the level of oxidative stress. However, if this enzyme system breaks down, the integrity of the red cells will be damaged. A lesion of the gene that produces one of the enzymes in the protective system in the red blood cells will cause an observable pathological condition. For example, glucose-6-phosphate dehydrogenase deficiency, a genetic disorder of red cells, is responsible for hydrogen peroxide induced hemolytic anemia. This disorder is due to the inability of the affected cells to maintain NAD(P)H levels sufficient for the reduction of oxidized glutathione resulting in inadequate detoxification of hydrogen peroxide through glutathione peroxidase (P. Hochstein, Free Radical Biology & Medicine, 5:387 (1988)).

The protective enzyme system of the red blood cells converts the toxic superoxide anion molecule to a non-toxic form in a two-step chemical pathway. The first step of the pathway is the conversion of the superoxide anion to hydrogen peroxide by the enzyme superoxide dismutase (SOD) (See Equation [2]). Because hydrogen peroxide is also toxic to cells, the red cells contain another enzyme, catalase, which converts hydrogen peroxide to water as the second step of the pathway (See Equation [3]).

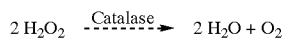

[3]

Red cells are also capable of detoxifying hydrogen peroxide and other toxic organoperoxides using the enzyme glutathione peroxidase which reacts with glutathione to convert hydrogen peroxide and organoperoxides to water. Red cells also contain an enzyme to prevent the build up of the met-hemoglobin produced by the auto-oxidation of hemoglobin. The enzyme met-hemoglobin reductase converts met-hemoglobin back to the native form of hemoglobin. Therefore, in the body, the toxic effects of the auto-oxidation of hemoglobin are prevented by specific enzyme-based reaction pathways that eliminate the unwanted by-products of oxygen metabolism.

The enzymatic oxygen detoxification functions of superoxide dismutase, catalase, and glutathione peroxidase that protect red blood cells from oxygen toxicity during normal oxygen transport do not exist in the hemoglobin-based oxygen carriers (HBOC) developed is to date. Without the oxygen detoxification function, the safety of the existing HBOC solutions will suffer due to the presence of toxic oxygen-related species.

The principle method by which the existing HBOC solutions are manufactured is through the removal of hemoglobin from the red cells and subsequent purification to remove all non-hemoglobin proteins a nd other impurities that may cause an adverse reaction during transfusion (See U.S. Pat. Nos. 4,780,210; 4,831,012; and 4,925,574). The substantial destruction or removal of the oxygen detoxification enzyme systems is an unavoidable result of the existing isolation and purification processes that yield the purified hemoglobin used in most HBOC. Alternatively, instead of isolating and purifying hemoglobin from red cells, pure hemoglobin has been produced using recombinant techniques. However, recombinant human hemoglobin is also highly purified and does not contain the oxygen detoxification systems found in the red cells. Thus, the development of sophisticated techniques to create a highly purified hemoglobin solution is a mixed blessing because the purification processes remove the detrimental impurities and the beneficial oxygen detoxification enzymes normally present in the red cells and ultimately contributes to oxygen-related toxicity.

One of the observed toxic side effects resulting from intravenous administration of the existing HBOCs is vasoconstriction or hypertension. It is well known that the enzyme superoxide dismutase (SOD) in vitro will rapidly scavenge the superoxide anion and prolong the vasorelaxant effect of nitric oxide (NO). Nitric oxide is a molecule that has recently been discovered to be the substance previously known only as the "endothelium-derived relaxing factor" (EDRF). The prolongation of the vasorelaxant effect of nitric oxide by SOD has been ascribed to the ability of SOD to prevent the reaction between the superoxide anion and nitric oxide. (M. E. Murphy et. al., Proc. Natl. Acad. Sci. USA 88:10860 (1991); Ignarro et.al. J. Pharmacol. Exp. Ther. 244: 81 (1988); Rubanyi Am. J. Physiol. 250: H822 (1986); Gryglewski et.al. Nature 320: 454 (1986)).

However, in vivo, the inactivation of EDRF by the superoxide anion has not been observed and is generally not thought to be likely. Nevertheless, certain pathophysiological conditions that impair SOD activity could result in toxic effects caused by the superoxide anion (Ignarro L. J. Annu. Rev. Pharmacol. Toxicol. 30:535 (1990)). The hypertensive effect observed in preclinical animal studies of the existing HBOC solutions suggests that the concentration of superoxide anion in large volume transfusions of the existing HBOCs is the cause for the destruction of EDRF and the observed vasoconstriction and systemic hypertension.

It is, therefore, important to delineate the hypertensive effect resulting from the reaction of the superoxide anion with nitric oxide (NO) from that resulting from extravasation and the binding of NO by hemoglobin. Upon transfusion of an HBOC, the hemoglobin can also depress the vasorelaxant action of nitric oxide by reacting with nitric oxide to yield the corresponding nitrosylheme (NO-heme) adduct. In particular, deoxy-hemoglobin is known to bind nitric oxide with an affinity which is several orders of magnitude higher than that of carbon monoxide.

These hemoglobin-NO interactions have been used to assay for nitric oxide and to study the biological activity of nitric oxide. For example, the antagonism of the vasorelaxant effect of nitric oxide by hemoglobin appears to be dependent on the cell membrane permeability of hemoglobin. In intact platelets, hemoglobin did not reverse the effect of L-arginine which is the precursor of nitric oxide. In contrast, in the cytosol of lysed platelets, hemoglobin is the most effective inhibitor of L-arginine induced cyclic-GMP formation mediated by nitric oxide. These experiments demonstrated that the hemoglobin did not penetrate the platelet membrane effectively. (Radomski et al., Br. J. Pharmacol. 101:325 (1990)). Therefore, one of the desired characteristics of the HBOCs is to eliminate the interaction of nitric oxide with hemoglobin.

Hemoglobin is also known to antagonize both endothelium-dependent vascular relaxation (Martin W. et. al. J. Pharmacol. Exp. Ther. 232: 708 (1985)) as well as NO-elicited vascular smooth muscle relaxation (Grueter C. A. et al., J. Cyclic. Nucleotide Res. 5:211 (1979)). Attempts have been made to limit the extravasation and hypertensive effect of hemoglobin by chemically stabilizing, polymerizing, encapsulating, or conjugating the hemoglobin in the HBOCs to prolong the circulation time. Therefore, although the current HBOCs are relatively membrane impermeable and able to transport oxygen, the HBOC solutions do not have the capability of preventing the reaction between superoxide anion and nitric oxide when transfused. The above example demonstrates the difficulty in addressing the oxygen toxicity/stress issue, even where the reactions mechanisms of oxygen transport are reasonably well understood, and despite decades of research to improve the hemoglobin production and formulation process.

An ideal solution to the toxicity problems of the existing blood substitutes would be a hemoglobin-based formulation that combines the oxygen-transport function of the existing HBOCs with the oxygen detoxification function of the red cells. However, a simple addition of the enzyme superoxide dismutase (SOD) into an existing HBOC solution would not be desirable because, by reducing the concentration of superoxide anion, the reaction whereby hemoglobin is oxidized to met-hemoglobin would be encouraged, leading to an undesirable build-up of met-hemoglobin (See Equation [1]). Also, it is not desirable to encourage the conversion of the superoxide anion to hydrogen peroxide in a hemoglobin solution because the hydrogen peroxide is toxic and reactive and will decompose to toxic hydroxyl radicals or form other toxic organoperoxides during storage.

Because synthetic blood substitutes would ideally be infusible in large quantities, compounds which interact with free radicals must be able to offer sustained in vivo function and must be stable and non-toxic. Pursuant to this invention, nitroxides and nitroxide-labelled macromolecules, including hemoglobin, albumin and others are used to alleviate the toxic effects of free radical species in a living organism.

Another example of physiological damage resulting from a free radical cascade originating in the vascular compartment is the cerebral edema, necrosis, and apoptosis, which is associated with a number of pathologies, including cerebrovascular occlusion and ischemic events commonly known as a "stroke". A significant portion of the brain damage from a stroke also arises from a reperfusion event following the occlusion.

The brain damage resulting from stroke exacts large human and health care costs and scientists and physicians have long sought a treatment for preventing stroke injury to the brain. A primary contribution to the brain damage attendant to the ischemic/reperfusion injury in stroke is free radical formation in the vascular space and the resulting cascade leading to cellular injury. Oxygen free radical toxicity is linked to the edema and neural injury resulting from stroke, as shown, for example, in transgenic (Tg) SOD-1 mouse. Chan, P. H., C. J. Epstein, H. Kinouchi, H. Kamii, S. Imaizumi, G. Yang, S. F. Chen, J. Gafni, and E. Carlson (1994). SOD-1 transgenic mice are a model for studies of neuroprotection in stroke and brain trauma. *Ann. N.Y. Acad. Sci.* 738: 93–103. Chan, P. H., C. J. Epstein, H. Kinouchi, S.Imaizumi, E. Carlson, and S. F. Chen (1993). Role of superoxide dismutase in ischemic brain injury: Reduction of edema and infarction in transgenic mice following focal cerebral ischemia. In *Molecular Mechanisms of Ischemic Brain Damage*, K. Kogure and B. K. Siesjo, eds. Amsterdam: Elsevier. pp. 96–104. Kinouchi, H., C. J. Epstein, T. Mizui, E. Carlson, S. F. Chen, and P. H. Chan (1991). Attenuation of focal cerebral ischemic injury in transgenic mice overexpressing CuZn superoxide dismutase. *Proc. Natl. Acad. Sci. USA* 88: 11158–11162.

In the SOD-1 transgenic mouse, a human SOD transgene is expressed in the mouse brain at up to three times normal level, and provides 30% protection against stroke injury as measured by infarction size, edema and neurological deficit following a focal ischemic insult. Free radical damage in stroke is localized in both the intracellular and vascular spaces, reflecting (a) damage to cell membranes and organelles in tissue, and (b) damage specifically to the vascular endothelium. Imaizumi, S., V. Woolworth, and R. A. Fishman (1990). Liposome-encapsulated superoxide dismutase reduces cerebral infarction in cerebral ischemia in rats. *Stroke* 21: 1312–1317. Liu, T. H., J. S. Beckman, B. A. Freeman, E. L. Hogan, and C. Y. Hsu (1989). Polyethylene glycol-conjugated superoxide dismutase and catalase reduce ischemic brain injury. *Am. J. Physiol.* 256: H586–H593. Chan, P. H., S. Longar, and R. A. Fishman (1987). Protective effects of liposome-entrapped superoxide dismutase on post-traumatic brain edema. *Ann. Neurol.* 21: 540–547.

No drug therapy has yet been proven completely effective in preventing brain damage from cerebral ischemia. A large number of experimental neuroprotective agents, thrombolytics, and anticoagulants have been tested, but the adverse side effects associated with many such agents may discourage their use. Also, the ischemia/reperfusion injury, which may also arise during surgery, for example, following embolism by gas bubbles, from embolism by endogenous or exogenous particles, or from hypotensive episodes. These problems are unlikely to be addressed by anticoagulant therapy. Given the antioxidant protective mechanism of the nitroxide-based compounds of the invention, the invention provides the ability to substantially alleviate reperfusion injury by protecting the cells from damage during reperfusion. Furthermore, given the ability to detect the compounds spectroscopically, this invention may be used as a therapeutic and diagnostic agent for stroke as well as a prophylactic agent for perioperative stroke, perioperative cardiac damage and renal injury and may be used in combination with other anti-stroke drugs such as thrombolytics, glutamate release inhibitors, calcium influx blockers and NMDA receptor antagonists.

The prevention of oxidative stress in the vascular system also alleviates or reduces the development of oxidized lipids which may lead to arterial plaques and atherosclerosis in the walls of the cardiovascular system, particularly in arteries proximate to the heart. The mechanism of free radical reactivity also implicates an oxidation of plasma LDL and such oxidized lipids are also thought to play a role in reperfusion injury in the brain and central nervous system and in several diseases and conditions of the cardiovascular system.

As will be appreciated by the several embodiments of the invention described herein, the capability of nitroxides, used together with biological macromolecules pursuant to this invention, to control the damage caused by free radicals in vivo creates the ability to design therapeutic and diagnostic nitroxide-containing formulations and methods for their use which have a broad range of applications. A large number of physiological states and processes where oxygen-derived free radicals are present may be treated or diagnosed by the use of the compounds described herein. The use of membrane-permeable, low molecular weight nitroxides in combination with biocompatible macromolecules such as hemoglobin, albumin, and others, also allows the researcher to tailor the nitroxide-containing formulation to fit the specific environment of interest.

A multi-component nitroxide-based system also functions as a radioprotective agent for use in cancer radiotherapy and in the treatment of radiation exposure. In clinical applications, the efficacy of radiation therapy will be enhanced by allowing higher radiation dosages to be used safely.

There has long been a need for agents which can protect against the ill effects of ionizing radiation encountered in the course of medical radiotherapy or as the result of environmental radiation exposure. Such agents would also be useful tools in research on mechanisms of radiation cytotoxicity. Cysteamine, a sulfur-containing compound, was one of the earliest radioprotective agents identified. Its discovery prompted the United States Department of Defense to sponsor the synthesis and systematic screening of over 40,000 compounds in an attempt to find more effective agents. This monumental undertaking resulted in the discovery of a few radiation protectors such as the aminothiol compound known as WR-2721. More recently superoxide dismutase, interleukin I, and granulocyte-macrophage colony-stimulating factor have been shown to have radioprotectant activity. In a comparison of these agents, WR-2721 showed the most substantial and selective protection of normal tissues. However, when used in patients undergoing cancer radiotherapy, concern over inherent toxicity and nonselective protection of tumor dampened enthusiasm for the use of WR-2721. The capability to protect tissue from "ionizing" radiation also provides the ability to protect and treat dermal tissue suffering from exposure to UV radiation. Thus, compounds formulated pursuant to this invention can be provided with a vehicle for administration such as a lotion or cream which enables application to the skin.

While certain stable nitroxides have been found to have antioxidant and radioprotectant activities. However, these membrane permeable nitroxides are rapidly reduced in vivo to an inactive form and may be toxic in elevated doses. The utility of administration of membrane permeable nitroxides can be substantially enhanced pursuant to this invention.

SUMMARY OF THE INVENTION

This invention discloses stable nitroxides used in connection with biologically compatible macromolecules, including other nitroxides for therapy and diagnosis in biological systems. In particular, this invention describes low molecular weight, membrane-permeable nitroxides used in connection with nitroxides bound in a high molar ratio to biocompatible macromolecules such as albumin and hemoglobin. In certain applications, an interaction between one form of a nitroxide and another form of nitroxide with a differential free radical stability facilitates electron or spin transfer between the species. The differential stability may result from the electrochemical environment of the species or from the inherent nature of the compound. This invention also contemplates the use of stable nitroxide free radicals, precursors and derivatives, hereafter referred to collectively as "nitroxide(s)", to provide the oxygen detoxification function of the red cells to hemoglobin-based blood substitutes and to alleviate oxidative stress and to avoid biological damage associated with free radical toxicity, including inflammation, radiation, head injury, shock, post-ischemic reperfusion injury, stroke, renal failure, endothelial damage, lipid peroxidation, sickle cell anemia, leukocyte activation and aggregation, apoptosis, ionizing radiation, alopecia, cataracts, sepsis, psoriasis ulcers, and the aging process, among others.

In certain embodiments, stable nitroxides or derivatives thereof are used to create several formulations for a blood substitute that will possess the oxygen detoxification function of the red cells. These formulations may be described herein as hemoglobin-based red cell substitutes (HRCS) because the oxygen transport capability of the hemoglobin-based oxygen carriers (HBOC) is enhanced by providing the oxygen detoxification function of the body's red cells. This permits the design of vasoneutral hemoglobin-based oxygen carriers which avoid the hypertension observed in many HBOC.

To overcome the drawbacks in the use of nitroxides alone, in preferred embodiments of this invention, a polynitroxide-labelled macromolecule, such as Tempo-labelled human serum albumin is infused either alone or together with a free membrane-permeable nitroxide to provide extended activity of the nitroxide in vivo. One benefit of such a formulation is an improved radioprotective agent which can be used in both diagnostic and therapeutic medical application and to protect against exposure to radiation from any source. In therapeutic medical applications, increased dosages of radiation are enabled to be administered thereby improving the possibility that radiation therapy will be successful. This capability is particularly significant in certain tumors such as those in the brain, and, is useful in combination with imaging and oxygen delivery as described herein, particularly with those tumors containing regions of hypoxia.

Also, nitroxides are detectable by electron paramagnetic resonance spectroscopy and nuclear magnetic resonance spectroscopy. With the development of advanced imaging instrumentation, images of intact biological tissues and organs are available based on a measurement and detection of the stable free radical of a nitroxide. Pursuant to this invention, active nitroxide levels in the body may be maintained for a prolonged period of time allowing both improved image contrast and longer signal persistence than seen with low molecular weight membrane permeable nitroxides alone. Moreover, unlike certain existing image-enhancing agents, the compositions disclosed here are capable of crossing the blood-brain barrier.

Additionally, due to their antioxidant activity, the compositions disclosed herein have therapeutic value which, in combination with their diagnostic value, allows the novel compositions and methods of this invention to be used advantageously in a wide variety of applications.

Materials and methods are also described for the preparation and administration of stable nitroxides in several forms. In particular, inactive, relatively non-toxic precursors or derivatives of membrane-permeable nitroxides are described which are converted in vivo by other compounds described herein to biologically active nitroxides, or antioxidant enzyme mimics. In either case, the chemically reduced (inactive) nitroxide may be reactivated, by other nitroxides of differential stability or by nitroxide-labelled macromolecular species, after having been reduced in the process of detoxifying harmful free radicals. As a result of this regeneration effect, the nitroxides of this invention have longer half lives in vivo compared to low molecular weight, membrane-permeable nitroxides alone. Thus, this invention provides compositions and methods to enhance the effectiveness of any application where nitroxides are efficacious.

Using the multi-component system of this invention, a dynamic equilibrium is created between low molecular weight, membrane-permeable nitroxides and membrane permeable nitroxide-containing species of differential stability. In particular, a nitroxide-based compound featuring a nitroxyl group capable of accepting an electron from another nitroxide, such as a membrane impermeable macromolecular-bound nitroxide capable of accepting an electron from the hydroxylamine derivative, may act as an enzyme mimic to regenerate the active function of the membrane permeable nitroxides, or vice versa as an electron acceptor, to convert the hydroxylamine form of a nitroxide to the free radical form.

The capability to maintain the concentration of an active nitroxide in vivo pursuant to this invention offers advantages in virtually any application where administration of a nitroxide is beneficial, but the utility is limited due to rapid reduction in vivo, or where the optimally effective dose of a membrane preamble nitroxide is toxic. For example, the increased active half-life of nitroxide in vivo pursuant to this invention provides radiation protection and improved imaging in clinical and other applications where the effective dose of a low molecular weight membrane permeable nitroxide is toxic or rapidly consumed.

Nitroxides, which are paramagnetic by virtue of a stable unpaired electron, function as imaging agents in nuclear magnetic resonance imaging (NMR/MRI) and in electron paramagnetic resonance imaging (EPR/ERI). However, due to the rapid reduction of nitroxide to a spectroscopically invisible species, most typically the hydroxylamine form, the utility of such agents is limited. Because free radical species are implicated in reperfusion injury, and are known to accompany oxygen metabolism, ischemic tissue injury, and hypoxia may be observed using the compositions of this invention as imaging agents. Additionally, the antioxidant, enzyme-mimic effect of the compositions of this invention provides the added benefit of protection from oxidative damage.

A distinct advantage of the multi-component nitroxide based system is the capability to deliver the antioxidant, radioprotective, anti-ischemic, image-enhancing, enzyme-mimic, etc. function to several regions of the body, such as the vascular compartment, interstitial space, and intracellular regions or to a particular region based on selective permeability of the biological structure or utilizing known methods of administration which provide targeted or localized effect. The researcher or clinician can tailor the multi-component system described here to fit the application. For example, different formulations described herein have differing levels of vasorelaxant effect. The ability to tailor the selection of the nitroxide-containing species of the multi-component system of the invention provides the ability to selectively treat or diagnose particular disease states or conditions or to provide increases or decreases in the free radical form of the nitroxide. For example, as will be appreciated by those skilled in the art, the invention can be particularly applied to the cardiovascular system by intravenous of one or more of the components of the multi-component system described herein. Similarly, a particular region of the skin may be selected by topical administration of one nitroxide while administering the other species by topical, oral, or intravenous administration depending on the particular application of this invention.

Fundamentally, in certain embodiments, a nitroxide (including precursors and metabolic substrates) is provided which is selected to perform the desired function, i.e., radioprotection, imaging, enzyme-mimic, etc., and another nitroxide-based species is provided as a reservoir of activity. In terms of electron spin transfer, one species may be considered an "acceptor" nitroxide and the other a "donor nitroxide." In certain embodiments, the "donor" and "acceptor" may remain substantially physically separated in vivo and should have different stabilities in their free radical moieties. In a preferred embodiment, the acceptor nitroxide is a polynitroxide albumin which distributes predominantly in the vascular space and acts as a storehouse of activity. The donor species is typically a low-molecular weight, membrane permeable species such as TPL or TPH. Alternatively, the donor species may be membrane impermeable and the acceptor species membrane permeable and the species selected such that the activity of a nitroxide is inhibited.

Those of ordinary skill will appreciate that the individual species selected as the donor or acceptor may vary as long as substantial physical separation is maintained and differential stability is achieved. For example, the same nitroxide species may act as both acceptor and donor. In such an example, TPL labelled at a number of amino groups on a macromolecular species such as albumin provides a substantially membrane-impermeable acceptor nitroxide. Differential stability of the macromolecular-bound TPL is provided by labelling at the amino groups such that the remaining carboxyl groups create an acidic microenvironment yielding a less stable free radical state in the albumin-bound TPL. Alternatively, different unbound nitroxide species may be provided which, by virtue of their inherent chemical and electrical structure, provide the requisite separation and differential stability.

The dynamic equilibrium which is created by the compounds of this invention is between a reduced form of a nitroxide and an oxidized form such that one is active in vivo and the other inactive. The fundamental mechanism is acceptance of an electron from a first nitroxide, particularly the reduced hydroxylamine derivative thereof, by the nitroxyl group of a second nitroxide. The second nitroxide is capable of accepting an electron when it contacts the first nitroxide by virtue of the differential stability of the free radical nitroxyl group. In one example, the free radical or "oxidized" form, e.g. TPL, becomes rapidly reduced to TPH until regenerated to TPL by polynitroxide albumin (PNA).

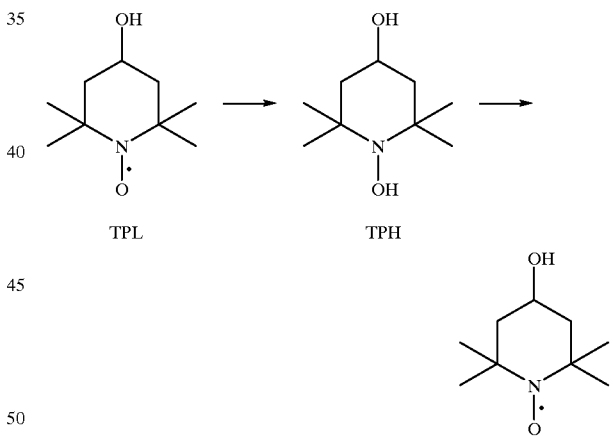

The preferred compositions using nitroxides in connection with biocompatible macromolecules may be varied; for example, with a physiologically compatible solution for infusion such as a hemoglobin-based oxygen carrier, the compositions include: 1) nitroxide-containing compounds added to a storage container or contained within a filter; nitroxides may be chemically attached to an insoluble matrix used in a filter or contained therein in several forms as an advantageous method of storage and administration, 2) nitroxide covalently linked to hemoglobin that is stabilized by chemical or recombinant cross-linking, 3) nitroxide covalently linked to polymerized hemoglobin, in particular, in 2, 4, and 8 molar equivalents of nitroxide, 4) nitroxide coencapsulated with hemoglobin inside a liposome or intercalated into a liposome membrane, (5) nitroxide covalently bound to conjugated hemoglobin, (6) nitroxide covalently bound to several forms of albumin in high molar ratios, i.e., between 6 and 95, (7) nitroxide covalently bound to immunoglobulins, and any combination of the above in a multicomponent system.

As noted, the above compositions may be used independently or in connection with low molecular weight, membrane permeable nitroxides depending on the application. Moreover, the above compositions may be specially formulated with other compounds to alter their reactivity or stability in vivo. In particular, cyclodextran and other recognized stabilizing agents may be used to enhance the stability of hemoglobin-based solutions. Also, the essential nutrient selenium is known to generate superoxide and may be used with a polynitroxide macromolecule to promote the oxidation thereof. These formulations may also be used with other known compounds that provide protection from oxidative stress, which enhance imaging, which increase or decrease sensitivity to radiation, and other known compounds with clinical or diagnostic utility.

Experimental results are presented below to demonstrate that low molecular weight nitroxides may be regenerated from a reduced inactive form to their active form by interaction with the nitroxide-labelled macromolecules of this invention. The experimental results and procedures below show that nitroxides may be attached to biocompatible macromolecules, including albumin and stabilized, polymerized, conjugated and encapsulated hemoglobin, for diagnosis therapy, and measurement of physiological conditions related to oxidative stress. The interaction of nitroxide-labelled hemoglobin and nitroxide-labelled albumin, both alone and in combination with a low molecular weight nitroxide, with free radicals suggests that other biologically compatible macromolecules with a substantial plasma half-life may be labelled with nitroxides and used pursuant to this invention to advantageously provide resistance to or protection from oxidative stress or toxicity caused by free radical chemical species.

Experimental results are also presented to demonstrate that the compositions and methods of this invention are anti-hypertensive when infused with an HBOC such that the infusion of an HBOC solution is rendered vasoneutral. Radioprotection is demonstrated both with cell cultures and with mice exposed to lethal doses of radiation. EPR images of the rat heart are shown which are capable of monitoring the progress of ischemia and reperfusion injury and which demonstrate that, in addition to image-enhancement, the compositions disclosed herein protect the ischemic heart from reperfusion injury. Protection from ischemic/reperfusion injury is shown in both the cardiovascular and cerebrovascular systems, experimental results are also presented to show the protective effect of the invention in inhibiting lipid oxidation and leukocyte activation and in treatment and protection of the skin.

DESCRIPTION OF FIGURES

The file of this application contains at least one photograph/image in color. Copies of this patent with color figures will be provided by the Patent and Trademark Office upon request and payment of the necessary fee.

FIG. 5 is an ESR spectra of 4-(2-bromoacetamido)-TEMPO-labelled HBOC with different molar ratios of nitroxides to Hb; FIG. 5A 2:1, FIG. 5B 4:1 and FIG. 5C 8:1. The instrument sensitivity were decreased proportionately from FIG. 5A to FIG. 5B to FIG. 5C to record the spectra so that the center peak (Mo) would be shown to have similar peak height.

FIG. 7 shows the plasma half-life of 4-(2-bromoacetamido)-TEMPO-labelled HBOC in a mouse. FIG. 7A is the ESR spectrum of the nitroxide signal recorded from the mouse tail approximately 10 minutes after intravenous infusion of 0.5 ml of the sample shown in FIG. 6. FIG. 7B is the time dependent (scan time 30 minutes) decrease in the center peak (Mo) signal intensity of FIG. 7A recorded at 10 times of the instrument sensitivity. FIG. 7C is a continuation of FIG. 7B at the end of its scan.

FIG. 8 shows the plasma half-life of a mixture of 4-(2-bromoacetamido)-TEMPO-labelled HBOC (8 g/dl of Hb and 8:1 TEMPO to Hb) and $^{15}ND_{17}$ TEMPOL (0.5 ml in a 32 g. mouse) recorded from the mouse tail with a cannula for immediate recording of the infused nitroxides. The ESR spectrum of the sample prior to injection is shown in FIG. 6.

FIGS. 15A, 15B, and 15C, respectively, are electron paramagnetic resonance (EPR) spectra of: 15A, TPL (2 mM) in sodium phosphate buffer 50 Mm, PH 7.6; 15B, TPH (2 mM) in the same buffer; 15C, polynitroxide albumin (PNA). EPR spectrometer setting conditions as follows. Microwave power: 8 mW; Receiver gain: 1.00e+03; Modulation amplitude: 0.5 G; Modulation frequency: 100 KHz; Microwave frequency: 9.43 GHz; Sweep width: 200 G.

FIGS. 18B and 18D show TOPS activation by albumin labelled with different species of nitroxide. FIG. 18C is nitroxide-labelled hemoglobin-based oxygen carrier. FIG. 18B shows (1) 50 Mm TOPS only; (2) 43 Mm PNA only; (3) PNA (43 mM) mixed with TOPS (50 Mm) in sodium phosphate buffer pH 7.8 for 2 min. FIG. 18C shows (1) 50 Mm TOPS only; (2) 15 Mm PN-HBOC; (3) PN-HBOC (15 mM) mixed with TOPS (50 mM) in sodium phosphate buffer pH 7.8 for 2 min. FIG. 18D shows (1) 50 mM TOPS only; (2) 10 Mm B3T-labelled albumin only; (3) B3T-labelled albumin (10 mM) mixed with TOPS (50 mM) in sodium phosphate buffer pH 7.8 for 2 min.

FIG. 34A is a section from the brain of an untreated animal, showing massive ischemic damage (unstained area) of essentially the entire hemisphere. Edema appears as enlargement of the infarcted hemisphere compared with the opposite hemisphere of the same brain. FIG. 34B is a section from the brain of a PNA-treated animal, showing normal histology and absence of edema. This indicates that PNA provides protection against stroke injury.

FIG. 41 shows pharmacokinetics of intravenous $^{15}$N-TPL (1% v/w), measured at the patch of skin on the back of the mouse where PNA had been injected intradermal. The intensity of the low field $^{15}$N-TPL peak is plotted against time. The $^{15}$N-TPL peak is plotted against time. The $^{15}$N-TPL signal rose after injection, then fell sharply within 5 minutes, reflecting bioreduction. In the presence of PNA as shown here, the $^{15}$N-TPL signal stabilized after 5 minutes and remained stable for at least 30 minutes, reflecting oxidation by PNA.

FIGS. 42A and 42B show the pharmacokinetics of intravenous $^{15}$N-TPL (1% v/w) measured at a patch of skin on the abdomen of the mouse. (A) The low field peak intensity rose and fell and fall within 5 minutes after the injection of $^{15}$N-TPL. (B) The increase in $^{15}$N-TPL signal intensity as a function of time after intradermal injection of 100 μl PNA was maintained for at least 30 minutes.

DETAILED DESCRIPTION OF THE INVENTION

Figure 1A:
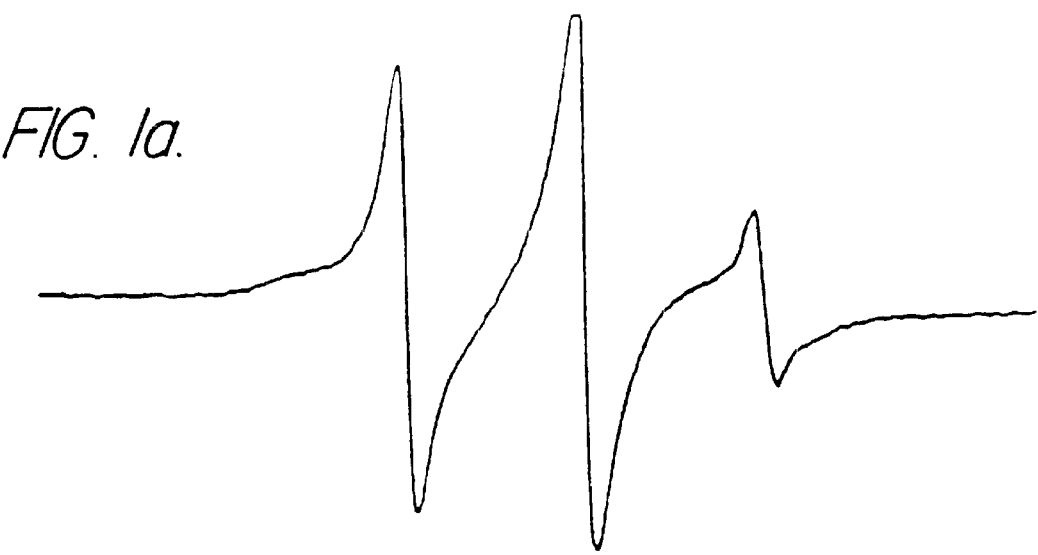
FIGS. 1A and 1B show the electron spin resonance spectra of 4-amino-TEMPO labelled o-raffinose polymerized hemoglobin recorded on (A) day 1 and (B) day 30 (TEMPO: 2,2,6,6 tetramethylpiperidine-1-oxyl).

Nitroxides are stable free radicals that are shown to have antioxidant catalytic activities which mimic those of superoxide dismutase (SOD), and which when existing in vivo, can interact with other substances to perform catalase-mimic activity. In the past, nitroxides have been used in electron spin resonance spectroscopy as "spin labels" for studying conformational and motional characteristics of biomacromolecules. Nitroxides have also been used to detect reactive free radical intermediates because their chemical structure provides a stable unpaired electron with well defined hyperfine interactions. In addition, nitroxides have been observed to act as enzyme mimics; certain low molecular weight nitroxides have been identified to mimic the activity of superoxide dismutase (SOD). (A. Samuni et. al. J. Biol. Chem. 263:17921 (1988)) and catalase (R. J. Mehlhorn et. al., Free Rad. Res. Comm., 17:157 (1992)). Numerous studies also show that nitroxides that are permeable to cell membranes are capable of short-term protection of mammalian cells against cytotoxicity from superoxide anion generated by hypoxanthine/xanthine oxidase and from hydrogen peroxide exposure.

The term "nitroxide" is used herein to describe stable nitroxide free radicals, including compounds containing nitroxyl groups such as synthetic polymers, their precursors (such as the N—H form), and derivatives thereof including their corresponding hydroxylamine derivative (N—OH) where the oxygen atoms are replaced with a hydroxyl group and exist in a hydrogen halide form. For the purposes of this invention, the chloride salt form of the hydroxylamine derivatives is generally preferred.

In the nitroxides described here, the unpaired electron is stable in part because the nitrogen nucleus is attached to two carbon atoms which are substituted with strong electron donors. With the partial negative charge on the oxygen of the N—O bond, the two adjacent carbon atoms together localize the unpaired electron on the nitrogen nucleus.

Nitroxides generally may have either a heterocyclic or linear structure. The fundamental criterion is a stable free radical. Structurally, nitroxides of the following formula are preferred where $R_1$–$R_4$ are electron donors and A is the remaining members of a heterocyclic ring.

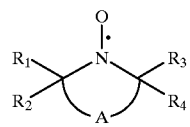

In these heterocyclic structures, "A" represents the remaining carbon atoms of a 5-membered (i.e., pyrrolidinyl or PROXYL with one double bond, i.e., pyrroline) or a 6-membered (i.e., piperidinyl or TEMPO) heterocyclic structure and in which one carbon atoms may be substituted with an oxygen atom (oxazolinyl or DOXYL) and certain hydrogen atoms may be substituted with up to two bromine atoms. In such heterocyclic structures, stable isotopes may be utilized (e.g., $_{15}$N, deuterium). Substitution at the α carbons should be such that the unpaired electron is maintained substantially in a πp orbital configuration. $R_1$ through $R_4$ are alkyls (straight and branched chain) or aryl groups but are preferred to be methyl or ethyl groups. The substituent groups on the alpha carbons in any nitroxide should be strong electron donors to enhance stability, thus methyl ($CH_3$) groups or ethyl ($C_2H_5$) groups are preferred although other longer carbon chain species could be used. See e.g., U.S. Pat. No. 5,462,946. Alternate structures which preserve the reactivity of the free radical are known to those of ordinary skill in the art and are continuing to be synthesized. See e.g., Bolton et al., "An EPR and NMR Study of some Tetramethylisoindolin- 2-yloxyl Free Radicals", J. Chem Soc. Perkin Trans. (1993); and Gillies et al., NMR Determination of EPR Hyperfine Coupling Constants of Some 5-(n-Alkyl)-1,1,3,3-tetrakis(trideuteriomethyl)isoindolin-2-yloxyls, J. Chem. Soc. Faraday Trans., 90(16), 2345–2349 (1994);

When linked with biocompatible macromolecules pursuant to this invention, the reactivity of the nitroxide is altered due to the microenvironment. This reactivity may be tailored by the labelling scheme employed and by the reaction with other compounds, such as selenium, which are known to alter the stability or reactivity of the free radical. In practice, stearic considerations may limit the scope of the nitroxide compounds that are practical and economical. The preferred nitroxides used with this invention include nitroxides having the following structure:

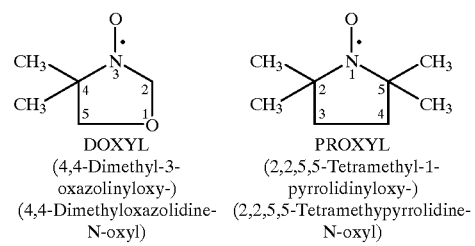

DOXYL
(4,4-Dimethyl-3-oxazolinyloxy-)
(4,4-Dimethyloxazolidine-N-oxyl)

PROXYL
(2,2,5,5-Tetramethyl-1-pyrrolidinyloxy-)
(2,2,5,5-Tetramethypyrrolidine-N-oxyl)

-continued

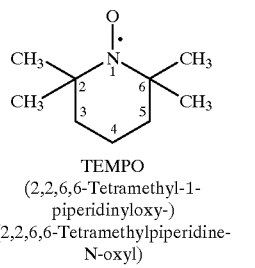

TEMPO
(2,2,6,6-Tetramethyl-1-piperidinyloxy-)
(2,2,6,6-Tetramethylpiperidine-N-oxyl)

As is apparent from the above, most suitable nitroxide compounds may be represented basically by the structural formula

assuming that the R group is selected from among the configurations which preserve the stability of the free radical.

As noted above, the structural form of the nitroxide may be varied without departing from its essential function. The nitroxide functional groups may also be incorporated into dimers, trimers such as B3T described below, oligomers, or polynitroxide synthetic polymers having a plurality of repeating subunits each containing at least one nitroxide. A preferred synthetic polymer has nitroxides and carboxyl groups in each subunit of the polymer. For example, the following compound may be synthesized by known techniques, for example as described in U.S. Pat. No. 5,407,657 from a diamine compound and a dianhydride to yield:

(1970); Hamilton et. al., "Structural Chemistry and Molecular Biology" A. Rich et. al., eds. W. H. Freeman, San Francisco, p.115 (1968); Griffith et. al., Acc. Chem. Res. 2: p.17 (1969); Smith I.C.P. "Biological Applications of Electron Spin Resonance Spectroscopy" Swartz, H. M. et. al., eds., Wiley/Interscience, New York p.483 (1972). Selected nitroxides have been covalently bound to hemoglobin molecules for the purpose of studying cooperative oxygen binding mechanisms of hemoglobin.

With respect to the macromolecules described here, at least two techniques for binding the nitroxides to a macromolecule, often known as "labelling strategies" are possible. The significance of specific labelling lies in the micro-environment in which the nitroxide is bound to the macromolecule and the nitroxide's resulting catalytic activity. Specific labelling at a particular ligand binding site or sites will yield a homogeneous product with a more consistent binding site micro-environment and thus a more reliable compound in terms of the catalytic specificity and activity of the nitroxide.

The term "hemoglobin" is used generally herein to describe oxy-, carboxy-, carbonmonoxy-, and deoxy-hemoglobin except as otherwise noted by the context of the description. The hemoglobin used with this invention may be human, recombinant or animal in origin and is obtained and purified by known techniques. The hemoglobin may be covalently bound to pyridoxal groups of pyridoxal-5'-phosphate or ring opened adenosine triphosphate (o-ATP) by reaction with the aldehyde groups and cross-linked derivatives of hemoglobin. The cross-linked derivatives may include polyfunctional, heterobifunctional and homobifunctional cross-linking regents such as dialdehyde, polyaldehyde, diepoxide, polyepoxide, activated polycarboxyl and dicarboxyl groups, for example, 3,5-bis-

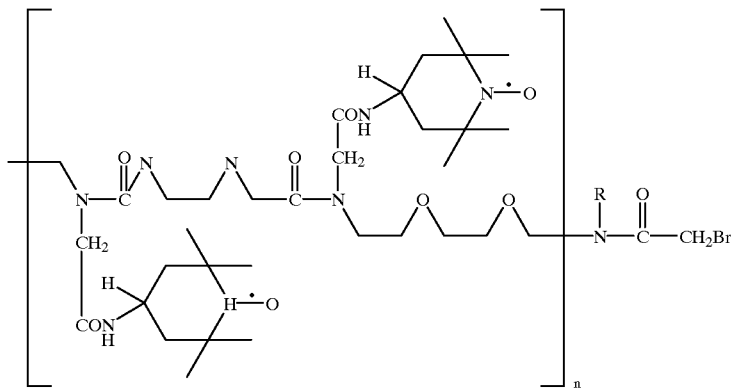

For purposes of the invention, nitroxide group of the polymer shown in U.S. Pat. No. 5,407,657 is preferably replaced with Bromo-TEMPO. Such synthetic polymers may be used to label hemoglobin, particularly native hemoglobin, by synthesizing the compound with a slight excess of the diamine to yield a free amino group at the terminal end of the polymer. The terminal amino group is reacted with a neutrophilic group such as bromoacetabromide yield a nitroxide polymer derivative of Bromo-TEMPO to enable labelling at the amino groups on the protein similar to that of PNA and PNH.

A variety of techniques have been described to covalently attach a nitroxide to biomacromolecules, including hemoglobin, albumin, immunoglobulins, and liposomes. See e.g., McConnell et. al., Quart. Rev. Biophys. 3:p.91 bromosilicyl-bisfumarate, and TEMPO succinate or TOPS See (U.S. Pat. No. 4,240,797) cyclodextrans and their anionic (e.g., sulfate) cross-linked hemoglobin as well as polymerized hemoglobin. The stabilized hemoglobin may be formed into microspheres having a cross-linked outer layer produced by cross-linking cysteine residues within the protein (VivoRx Pharmaceuticals, Inc., Santa Monica, Calif.). All hemoglobin solutions described herein and each at the other nitroxide-based solutions such as in other compounds of the invention described herein are administered in a physiologically compatible form such as in a physiologically accepted intravenous solution or suspended in an acceptable carrier, solvent or base. The hemoglobin solutions are cell-free to remove pyrogens, endotoxins, and other contaminants.

Preferred compositions using nitroxide in connection with albumin include:

1) non-specific labelling of albumin with nitroxide (e.g., 4-(2-bromoacetamido)-TEMPO at high nitroxide to albumin ratios;
2) specific labelling of albumin at specific ligand binding sites; and
3) enhanced labelling of albumin by reduction and alkylation of disulfide bonds.

As used herein, the term albumin includes human serum albumin, animal albumin, recombinant albumin, and fragments thereof. The albumin may be temperature or chemical treated to increase the available labelling sites. Additionally, the albumin may exist as a monomer, a dimer, a polymer, or may be enclosed in microspheres. Albumin as disclosed herein may also be treated with polyethylene glycol (PEG) by well-known techniques to increase its immunocompatibility.

A preferred technique for alleviating oxidative stress by augmenting the body's antioxidant capabilities is the use of multiple component nitroxide-based system. A first component is a membrane-permeable nitroxide, such as TEMPOL. By virtue of their charge characteristics and small molecular size, low molecular weight unbound nitroxides readily permeate the cell membrane and enter the intracellular space. A second component is another nitroxide-including species such as a biocompatible macromolecule-labelled with a high molar ratio of nitroxide (polynitroxide), for example, human serum albumin labeled with a 30:1 molar ratio of TEMPOL. The use of a multiple component nitroxide system of this invention helps to alleviate toxicity which could result from large, concentrated, or repeated doses of a low molecular weight membrane permeable nitroxide. Because the hydroxylamine form of the nitroxide is not active as an antioxidant, and because nitroxide toxicity at high doses is thought to be primarily due to the antioxidant activity causing perturbation of the cellular redox state, the hydroxylamine state displays much lower toxicity than the corresponding unreduced nitroxide. Thus, one embodiment of this invention describes the use of a non-toxic dose of a membrane-permeable nitroxide, in conjunction with a macromolecular polynitroxide, to activate a nitroxide in vivo which has been reduced to an inactive form. In similar fashion, the hydroxylamine may be administered as a non-toxic nitroxide precursor which is converted to an active antioxidant in vivo. The result is a safe and sustained therapeutic level of a powerful antioxidant in the body.

With regard to safety in vivo, the levels of nitroxide which may be administered pursuant to this invention are well tolerated in animals and are expected to be well tolerated in humans because nitroxides are known to be relatively safe: For example, the maximum tolerated intraperitoneal dose of TEMPO in mice is 275 mg/kg and the $LD_{50}$ is 341 mg/kg. Further, a macromolecule-bound nitroxide will be safer than a free nitroxide in its active form. The nitroxide-labelled macromolecules of this invention used in combination with free nitroxide will reduce the total quantity of nitroxide that otherwise would have to be administered to achieve an antioxidant effect. An added advantage of nitroxide-labelled macromolecules used in antioxidant formulations lies in the ability to achieve high active levels of nitroxides in their active antioxidant state with improved safety.

Most of the nitroxides studied to date in living organisms have been relatively low molecular weight compounds which can easily permeate across cell membranes into body tissues. The macromolecular-band nitroxides of this invention may be infused intravenously and may remain confined to the vascular compartment due to the membrane impermeability of the macromolecular species. In such an embodiment, a nitroxide which is covalently attached to a macromolecule will act to alleviate free radical toxicity while confining the nitroxide to a location, i.e., the vascular compartment, where the utility is optimized.

When TEMPOL is injected, it diffuses rapidly into the intracellular space, where it is reduced to the hydroxylamine form in the process of detoxifying (oxidizing) free radicals. In the process of scavenging the unpaired electron from a toxic free radical, the nitroxide is reduced to an oxoammonium intermediate. The oxoammonium intermediate can then react in either of two ways. It can be reoxidized back to a nitroxide by spontaneously donating the free radical-derived electron to some naturally occurring compound; this pathway may be described as enzyme-mimetic because the net result is that the nitroxide is unchanged. Alternatively, the oxoammonium intermediate can be further reduced to a hydroxylamine. The hydroxylamine is not paramagnetic (i.e., it is silent on EPR spectroscopy) and lacks the antioxidant catalytic activity of nitroxide. Reaction equilibria in vivo strongly favor reduction to the hydroxylamine. By virtue of its high membrane permeability and inert chemical backbone, the hydroxylamine also distributes freely in the intracellular and extracellular spaces, and persists in the body for a relatively long period of time. However, once the nitroxide is reduced to hydroxylamine the antioxidant activity is lost.

TEMPOL 4-hydroxyl-2,2,6,6-tetramethyl-piperidine-N-oxyl is rapidly consumed in the process of detoxifying free radicals; it is reduced to an oxoammonium intermediate, which can be oxidized back to nitroxide or further reduced to a hydroxylamine. Thus, the biotransformation of the nitroxide (in the process of free radical detoxification) yields a hydroxylamine. The hydroxylamine is not paramagnetic (it is silent on esr spectroscopy) and lacks the antioxidant catalytic activity of nitroxide. The use of TEMPOL alone is not favored therapeutically because it is rapidly converted to the hydroxylamine and may be toxic at the dosage level needed to achieve a meaningful antioxidant effect.

However, the hydroxylamine is chemically stable and relatively persistent in the body (the backbone of the nitroxide molecule is relatively inert) and, in accord with the teachings of this invention, can be chemically converted back to the active form of the nitroxide. This in vivo conversion enables the safe clinical use of nitroxides to provide a sustained antioxidant activity. As noted above, the unpaired nitroxyl electron gives nitroxides other useful properties in addition to the antioxidant activity. In particular, nitroxides in their free radical form are paramagnetic probes whose EPR signal can reflect metabolic information, e.g., oxygen tension and information on tissue redox states, in biological systems. Because naturally occurring unpaired electrons are essentially absent in vivo, EPR imaging has the further advantage that there is essentially no background noise. Nitroxides also decrease the relaxation times of hydrogen nuclei, and are useful as contrast agents in proton or nuclear magnetic resonance imaging (MRI). Nitroxides can also act as contrast agents to add metabolic information to the morphological data already available from MRI. For example, by substituting various functional groups on the nitroxide, it is possible to manipulate properties including relaxivity, solubility, biodistribution, in vivo stability and tolerance. Contrast enhancement obtained from nitroxide can improve the performance of MRI by differentiating isointense, but histologically dissimilar, tissues and by facilitating localization and characterization of lesions, such as blood brain barrier damage, abscesses and tumors.

A macromolecular polynitroxide tends to be distributed in the extracellular space due to its high molecular weight and low membrane permeability and is not readily reduced by the biochemical milieu. However, it has been discovered that the macromolecular polynitroxide is capable of accepting an electron from the hydroxylamine, causing an in vivo conversion back into a nitroxide with active antioxidant capabilities. This process effectively transfers antioxidant capacity from a high-capacity macromolecular storehouse of antioxidant activity outside the cell, to a high mobility membrane-permeable nitroxide which may cross the cell membrane to provide antioxidant activity inside the cell. Once inside the cell, the nitroxide is reduced to the hydroxylamine by oxidizing toxic free radicals, and then cycles out to the extracellular space, where it is reactivated by the macromolecular polynitroxide. Moreover, the reactivity of the macromolecular polynitroxide may be enhanced by adding other compounds such as Selenium.

Therefore, a particularly advantageous nitroxide-containing formulation can be prepared when a high molar ratio of a nitroxide is bound to a macromolecule (polynitroxide) and allowed to contact a therapeutically active amount of an unbound low molecular weight nitroxide in vivo thereby providing a catalytically active polynitroxide macromolecule. The interaction of the therapeutically active nitroxide with a catalytically active nitroxide provides a sustained antioxidant, radioprotectant, imaging agent, etc. in the surrounding tissues. In effect, the macromolecular species is a reservoir of antioxidant activity which can recharge the activity of the low molecular weight species which are able to permeate membranes. This symbiotic approach disclosed herein provides advantageous methods of administration, such as a topical application of a macromolecular nitroxide combined with oral administration of a low molecular eight nitroxide to provide localized, sustained antioxidant activity.

Based on the experimental results and formulation data presented here, the antioxidant, radioprotectant, antihypertensive, and spectroscopic activity of the nitroxide-containing species of this invention has been observed in vitro and in vivo with various formulations. Based on these results, the reaction mechanism whereby polynitroxide-labelled macromolecules and free nitroxides participates in the oxidation/reduction reaction of free radicals is sufficiently demonstrated that the capability exists to formulate novel HBOCs, and other nitroxide-containing macromolecules to detoxify free radicals which will be advantageously used in the diagnosis and treatment of a wide variety of physiological conditions.

In addition, this invention describes nitroxide-containing compounds that are associated with a container for storage or administration of pharmaceuticals such as intravenous fluids, topical agents and others. Nitroxide-containing compounds may be added in solid or liquid form to the interior of a container or may be covalently attached to the inner surface of a container. One advantageous technique for administration is the addition of nitroxide-containing compounds, with or without free nitroxide, to an in-line filter used in the administration of fluids. For example, a polynitroxide albumin may be incorporated within a filter along with free nitroxide or are attached to an insoluble matrix housed in a filter to be used with an intravenous fluid administration, such as an existing HBOC to scavenge toxic oxygen-related compounds before infusion into a patient.

The HRCS formulations and nitroxide-labelled macromolecules described below retard the formation of toxic oxygen-related species by causing a nitroxide to function as a "superoxide oxidase," an enzyme-like reaction not known to occur in the red cells. In these HRCS formulations, the nitroxide prevents the accumulation of the undesirable superoxide anion generated from the auto-oxidation of hemoglobin (See Equation [1]). The nitroxide-labelled macromolecules, such as albumin and immunoglobulins, similarly function as antioxidant enzyme mimics whose function remains localized in the vascular and interstitial compartments and which may react with membrane permeable nitroxides to provide intracellular protection.

Preferred compositions using nitroxide in connection with immunoglobulins include a nitroxide-labelled hapten or antigen bound to an immunoglobulin specific for the hapten or antigen.

Furthermore, pursuant to this invention, the beneficial therapeutic effects of nitroxide compounds can be controlled and sustained. For example, the nitroxide 2,2,6,6-tetramethyl-1-oxyl-4-piperidylidene succinic acid (TOPS), may be bound to the primary bilirubin binding site of human serum albumin. In vivo, this binding prolongs plasma half-life and slows the diffusion of the nitroxide into the intracellular space, reducing the necessary dosage (and hence reducing potential toxicity) and prolonging biological action. Thus, although nitroxides such as TOPS alone, without a macromolecular polynitroxide, may have utility as an antioxidant agent. Pursuant to this invention, it is possible to select or design carriers which can deliver nitroxides to particular sites in the body as a means of localizing therapeutic antioxidant activity.

In view of the stable chemical nature of the nitroxides, the compositions disclosed here can be administered by various routes. The membrane-permeable nitroxide can be administered parenterally or orally. In the reduced form, hydroxylamine, can act locally in the GI system or be taken up into the blood. Thus, sustained antioxidant activity can be provided in all body compartments. The macromolecular polynitroxide can be administered parenterally where it will remain localized in the extracellular space to reactivate reduced free nitroxide, orally, or topically/transdermally where it acts to activate circulating, reduced nitroxide thereby providing a localized antioxidant effect.

The particular reactivity of a protein-based macromolecular polynitroxide and a membrane-permeable nitroxide appears to be enhanced by heating of the macromolecule and labeling at primary amino groups in the polypeptide chain. Heating is known to alter the conformation of the macromolecule, stretching hydrogen bonds between amino and carboxyl groups and causing the macromolecule's quaternary structure to be altered. Subsequent covalent labeling by nitroxides at the amino groups may occur at relatively internal sites on the protein which were exposed as a result of heating. In the resulting nitroxide-labeled macromolecule, these nitroxide moieties are more protected from reaction with the solvent. Also, where nitroxides are attached to many amino groups on the protein, the preponderance of remaining carboxyl groups creates an acidic microenvironment surrounding the bound nitroxide. An acidic environment increases the reactivity of the nitroxide by drawing the unpaired electron in the N—O bond toward the oxygen atom.

In the embodiments of the invention directed to a red cell substitute, the requisite property of the nitroxides is their ability to influence the course of the superoxide anion cascade in HRCS by mimicking the superoxide oxidase, superoxide dismutase, and catalase activities without substantially being consumed in the process.

In the "superoxide oxidase" reaction, the superoxide anion is oxidized back into molecular oxygen without proceeding to the formation of hydrogen peroxide. This is accomplished in part by creating a storage condition wherein the concentration of nitroxide greatly exceeds that of oxygen. Used in the manner disclosed herein, the nitroxide prevents the cascade of undesirable oxidative reactions that begin with the formation of the superoxide anion. Furthermore, the physiologically compatible HRCS solutions described here will offer advantages over the existing HBOC solutions because the nitroxide will mimic the enzymatic activity of superoxide dismutase and catalase after the formulations described herein are infused into a patient.

Although a wide variety of nitroxides may be used with this invention, the nitroxide should be physiologically acceptable at a minimum concentration required to alleviate oxygen toxicity. In assessing an operative species, it is noteworthy that the relatively low toxicity of nitroxides has encouraged their development as contrasting agent in NMR imaging (See U.S. Pat. Nos. 4,834,964; 4,863,717; 5,104,641).

A number of methods for isolating and purifying hemoglobin solutions such that they are physiologically compatible are known to those skilled in the art. Typically, purified hemoglobin compositions contain at least 99% hemoglobin by weight of total protein, a total phospholipid content of less than about 3 $\mu$g/ml, less than 1 $\mu$g/ml of either phosphatidylserine or phosphatidylethanolamine and an inactive heme pigment of less than 6%. The purified hemoglobin solutions which are useful in this invention can be prepared using a variety of conventional techniques, including but are not limited to, those disclosed in Cheung et. al., Anal Biochem 137:481–484 (1984), De Venuto et. al., J. Lab. Clin. fled. 89:509–516 (1977), and Lee, et. al., Vith International Symposium on Blood Substitutes, San Diego, Calif. Mar. 17–20 Abstract H51 (1993).

The purified hemoglobin solutions used in this invention should be essentially free of oxygen. Hemoglobin in solution may be deoxygenated by admixture with a chemical reducing agent which causes the hemoglobin to release oxygen and to be maintained in a substantially deoxygenated state. A preferred method for deoxygenating a hemoglobin solution is performed by exposing a hemoglobin solution to an inert, essentially oxygen-free gas, such as nitrogen or carbon monoxide to cause removal of bound oxygen from the hemoglobin and conversion of the hemoglobin in solution to a form such as deoxy-hemoglobin or carbonmonoxy-hemoglobin that lacks oxygen. Alternatively, hemoglobin may be exposed to a vacuum or gas through a membrane that is permeable to oxygen yet impermeable to hemoglobin. For example, a hemoglobin solution may be passed through a diffusion cell having a membrane wall along which hemoglobin flows and through which oxygen is capable of passing, but hemoglobin is not. Inert gas is circulated along the side of the membrane wall opposite the hemoglobin solution causing the removal of oxygen and the conversion of the hemoglobin in solution to the deoxygenated state. Preferably, the deoxy-hemoglobin is maintained in an essentially oxygen-free environment during nitroxide-labelling, cross-linking, polymerization, or conjugation.

After removal of any bound oxygen, a nitroxide is covalently attached to the hemoglobin. Normally at least one, and preferably more than one, nitroxide will be covalently attached to a single hemoglobin molecule. The nitroxide may be covalently attached to the hemoglobin at any of several sites on the hemoglobin molecule including:

(a) at one or more of the free sulfhydro (—SH) groups, for example, at the β-93 site;

(b) at any reactive amino (—NH$_2$) groups, for example, in the DPG site at Val-1 of the β-chain and/or lysine-82 of the β-chain and/or lysine-99 of the α-chain;

(c) at any non-specific surface amino (—NH$_2$) or carboxyl (—COOH) group;

A nitroxide may also be bound to any residual aldehyde, epoxy, or activated carboxyl groups of a divalent- or a multivalent-cross-linker involved in the cross-linking and polymerization of hemoglobin or at any residual reactive groups on an agent such as dextran (Dx) or hydroxylethyl-starch (HES) or polyoxyethylene (POE) used to conjugate hemoglobin.

As described in Equation [1], above, during the storage period, the hemoglobin in an HBOC solution is slowly auto-oxidized by oxygen to form met-hemoglobin and the superoxide anion. However, during the storage of the HRCS that are the subject of this invention, the superoxide anion thus formed will reduce the nitroxide to a hydroxylamine derivative, and the superoxide anion will be oxidized to form molecular oxygen by the following reaction.

$$H^+ + RN\text{—}O \cdot + O_2 \cdot \rightarrow RN\text{—}OH + O_2 \qquad [4]$$

The conversion of superoxide anion to molecular oxygen described in Equation [4] prevents the accumulation of superoxide anion and the subsequent formation of hydrogen peroxide. This activity, described herein as a "superoxide oxidase" activity, will be most effective when the initial oxygen content in the composition is kept to a minimum, the composition is stored in an essentially oxygen free environment and the nitroxide concentration is sufficient to prevent the formation of superoxide anion and hydrogen peroxide. Therefore, storage of the HRCS in an essentially oxygen-free container is preferred.

Container systems that permit a solution to be stored in an oxygen free environment are well known because many non-hemoglobin based intravenous solutions are sensitive to oxygen. For example, a glass container that is purged of oxygen during the filling and sealing process may be used. Also, flexible plastic containers are available that may be enclosed in an overwrap to seal against oxygen. Basically, any container that prevents oxygen from interacting with hemoglobin in solution may be used.

Figure 1B:

To demonstrate the "superoxide oxidase" activity of a nitroxide, samples of nitroxide-labelled hemoglobin in solution are kept in an accelerated oxidative storage condition and the redox state of the nitroxide is studied over time by electron spin resonance spectroscopy. For example, an o-raffinose polymerized hemoglobin solution that has been labelled with 4-amino-TEMPO is stored in its oxygenated state in a sealed glass container (FIG. 1A). In such a state, the rate of superoxide anion and met-hemoglobin formation in solution is sufficiently rapid that the conversion of the nitroxide to its hydroxylamine derivatives may be conveniently monitored (See Equation [4] and compare FIGS. 1A and 1B). Equation 4 represents that the conversion of nitroxide to its diamagnetic hydroxyl derivative is coupled to the conversion of the superoxide anion back to molecular oxygen. The experimental evidence in support of such a conversion is shown in FIGS. 1A and 1B. The electron spin resonance spectrum of TEMPO covalently attached to the hemoglobin (FIG. 1A) was converted to its diamagnetic derivatives which result in the complete disappearance of the resonance peaks after storage of the sample for 30 days at 4° C. (FIG. 1B). The nitroxide is considered to have performed a "superoxide oxidase"-like activity when it is converted to its hydroxylamine derivative in the presence of hemoglobin.

Figure 1C:
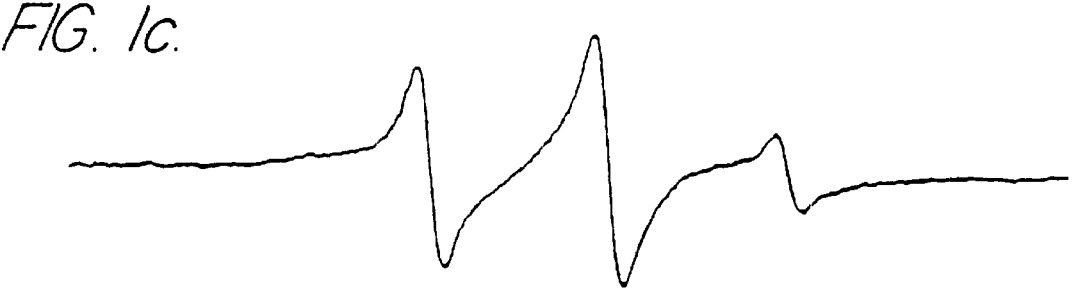
FIG. 1C is the spectra of the sample in FIG. 1A diluted with equal volume of unlabelled hemoglobin recorded on day 1.
Figure 1D:
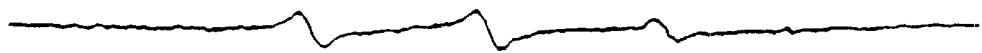
FIG. 1D is the sample in FIG. 1C recorded on day 30.

The "superoxide dismutase" activity of a nitroxide in an HBOC solution is demonstrated by showing the reconversion of the hydroxylamine derivative back to a nitroxide (See Equation [5] together with Equation [4]). Knowing that under the experimental conditions described in FIGS. 1A and 1B the nitroxide is fully converted to hydroxylamine (See Equation [4]), the nitroxide may be regenerated by simply providing more superoxide anion as shown in Equation 5. To demonstrate this reaction mechanism, the relative concentration of hemoglobin (and thus superoxide anion) to the nitroxide is increased by diluting the sample in FIG. 1A with an equal volume of unlabelled hemoglobin. A comparison of FIGS. 1A and 1C shows an approximate 50% reduction of the signal intensity of the nitroxide due to the dilution effect. On the other hand, after 30 days of cold storage at 4° C., the nitroxide was partially regenerated (See FIG. 1D) as predicted by Equation [5]. This observation is consistent with the reconversion of the hydroxylamine derivative to nitroxide coupled with the formation of hydrogen peroxide from superoxide anion.

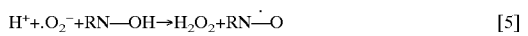

$$H^{+} + O_2^{-} + RN\text{—}OH \rightarrow H_2O_2 + RN\text{—}O \quad [5]$$

Summing equations [4] and [5] results in:

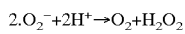

$$2 \cdot O_2^{-} + 2H^{+} \rightarrow O_2 + H_2O_2$$

which demonstrates that the nitroxide acts as a low molecular weight, metal-free, SOD mimic in "HBOC" solutions. The detection of electron spin resonance spectrum of the nitroxide (in FIG. 1D) is consistent with the reaction of superoxide anion with the hydroxylamine (R N—OH) resulting in the formation of nitroxide (R N—O) and hydrogen peroxide ($H_2O_2$). Recently, oxoammonium cation has been proposed to be involved as one intermediate in the nitroxide catalyzed dismutation of superoxide. (Krishna et al., Proc. Nat. Acad. Sci. USA 89 5537–5541 (1992)).

The HRCS formulations described herein will alleviate the oxidative stress originating from the generation of the superoxide anion in the existing HBOC solutions, and upon transfusion, will diminish the destruction of nitric oxide, the endothelium-derived relaxing factor (EDRF). If the destruction of EDRF is prevented, the problem of vasoconstriction and systemic hypertension that are observed when the existing HBOC solutions are infused into a patient will be substantially alleviated.

The number of nitroxide molecules per hemoglobin molecule may be in the range of approximately 1–40 or any integral value or range of values therebetween and for specific labelling is most preferably about 2. When used as a component of a multi-component system, the molar ratio of nitroxide to hemoglobin may be approximately 3 to 60 or any integral value or range of values therebetween. For example, a nitroxide such as 3-maleimido-PROXYL is covalently bound to hemoglobin in solution by first preparing a 100 mM solution of the nitroxide in ethanol as the carrier solvent. Two (2) molar equivalents of the nitroxide to hemoglobin was added directly with mixing to a DCL-Hb (8 g/dl) in Lactated Ringers. The reaction mixture was allowed to react at 22° C. with agitation until greater than 90% of the nitroxide was covalently linked to the DCL-Hb, usually within one hour. The unreacted nitroxide was then removed with a cross-flow membrane filtration system having a molecular-weight cut-off of 30,000 daltons by washing three (3) times with 10 volumes of Lactated Ringers. The retantate hemoglobin concentration is adjusted to between 7–14 g/dl, sterile filtered, and stored at 4° C. After transfusion, when the HRCS is fully oxygenated, the nitroxide is expected to function as a SOD-mimic and secondly as a catalase-mimic. As an SOD-mimic it dismutates the superoxide anion to hydrogen peroxide (See Equation [2]) and consequently protect against the destruction of nitric oxide in the endothelium to prevent vasoconstriction. As a catalase-mimic it prevents hydrogen peroxide toxicity by converting the latter to harmless water (See Equation [3]).

As noted above, nitroxides have been covalently bound to hemoglobin to study the cooperative oxygen binding properties of the hemoglobin molecule itself. However, nitroxides have not been used with stabilized, i.e., cross-linked, or polymerized, encapsulated, or conjugated hemoglobin solution that are physiologically compatible. Nor have synthetic nitroxide-containing polymers been used to label native hemoglobin. The known chemistry of hemoglobin and nitroxides suggests that it is possible to perform similar nitroxide-labelling of hemoglobin that has been chemically cross-linked or cross-linked through recombinant techniques by selecting an available site on the hemoglobin molecule that is not blocked by the particular compound used to stabilize, polymerize, or conjugate the hemoglobin molecule (s). Because certain of the stabilized and polymerized forms of hemoglobin described below are currently involved in clinical trials, the attachment of nitroxides to these stabilized and polymerized hemoglobin-based oxygen carriers is described below to demonstrate that the oxygen detoxification function of this invention is applicable to the existing hemoglobin solutions.

The nitroxide-labelling technology demonstrated here in the example of nitroxide-HBOC is readily applied to the production of other nitroxide-labelled macromolecules with useful antioxidant and enzyme-mimetic activities, for example nitroxide-labelled serum albumin and nitroxide-labelled immunoglobulin. Forms of serum albumin which can readily be labelled by nitroxide by this technology are monomeric (normal) albumin, and albumin homodimers, oligomers, and aggregates (microspheres and microbubbles) and polypeptide fragments of each. As described herein, the named protein or macromolecule includes fragment, i.e., polypeptide fragments of a protein.

Due to the differences in application, the formulations described herein may be used together or in isolation. For example, in the therapy and diagnoses of cardiac reperfusion injury or ischemic injury in the cerebrovascular system, it may be desirable to take advantage of several aspects of this invention, i.e., oxygen delivery, systemic protection from oxidative stress, localized protection from reperfusion injury, and enhanced imaging. In such a case, a combination of the formulations described herein could be used such as an existing HBOC, nitroxide-labelled albumin and a low molecular weight nitroxide which could be administered simultaneously or in sequence, depending on the therapeutic or diagnostic goal.

With respect to selecting a particular formulation and method of administration pursuant to this invention, the formulation and method of administration are dictated by the particular application. The selection of a nitroxide-based compound capable of accepting an electron from a low molecular weight membrane permeable species for a particular application may be made to complement, several available methods of administration and preferred formulations may be selected based on the site specific protection desired for the particular application. The avoidance of oxidative stress from infusion of a hemoglobin-based oxygen carrier as described above is a prime example of selecting formulations and methods of administration pursuant to this invention to provide specific protection from free radical toxicity to avoid the toxic side effects of HBOC infusion. Where site specific protection or activity is desired in the skin or dermal layers a preferred compound is TOPS because it is relatively small and membrane permeable. Where specific protection or activity is desired in the gastrointestinal tract, a polynitroxide dextran is preferred because such a compound is less susceptible to enzymatic digestion while in the gastrointestinal tract. In such an application, oral or rectal administration is preferred. Where specific protection or activity is sought for the intravenous or intravascular regions, such as the cerebrovascular or cardiovascular system, a polynitroxide albumin is preferred because albumin is a major plasma protein, is well-tolerated, easy to administer, and exhibits an extended plasma half-life. Such applications may also include a hemoglobin-based oxygen carrier or polynitroxide derivative thereof. The same rationale applies for intraperitoneal or intradermal administration.

As shown by the several examples, the administration of the compounds of the invention may be localized in the body or may be directed to a single group of cells or an organ. In particular, the preservation of an organ for transplantation may be achieved by infusion of polynitroxide albumin, either before or after the removal of the organ from the body. For example, in a heart transplant, PNA is used to selectively perfuse the heart, i.e., by concentrated intravenous administration followed by removal of the organ from the body. The organ may also be transplanted and stored in a PNA bath to prevent deterioration by processes such as lipid peroxidation, oxidative stress, etc. Furthermore, following surgical transplantation, when the organ is reperfused with oxygenated blood, the organ will be protected in the same way as is demonstrated herein ischemic reperfusion injury of the heart and brain. If specific protection in the lungs is desired, an aerosol form of polynitroxide albumin is preferred to enable coating of the pulmonary airways. As will be apparent to those skilled in the art, these preferred formulations may be altered depending on the particular application.

As noted, the above formulations are preferred embodiments of the electron accepting compound. With respect to the membrane permeable electron donating compound, the selection of a preferred compound also depends on the application and method of administration. The formulation and method of administration should achieve a systemic or tissue specific distribution commensurate in scope with the extent of the free radical species generated by, or coincident with, the physiologic condition of interest or the region to be imaged or treated. For example, in sepsis, a large scale collapse of the circulatory system is observed which accompanies a systemic increase in free radical generation. Similarly, whole body irradiation results in free radical generation throughout the body. In such situations, a small molecular weight, membrane permeable, electron-donating nitroxide such as TEMPOL may be administered orally or intravenously in a quantity to insure systemic distribution. Accordingly, such administration should be accompanied by administration of an electron acceptor which is also widely distributed such as an intravenous administration of polynitroxide albumin. Where the free radical generation is more localized, it is preferred to provide the localized protection or activity by selective application of the electron accepting species because the membrane permeable species tends to become systemically distributed upon administration, although a topical administration of the membrane permeable species to the skin may yield a more localized effect.

Based on the disclosure herein, those skilled in the art can select formulations and methods of administration to most effectively meet the demands of the particular application where this invention is to be used. For example, to achieve image enhancement of the gastrointestinal system, one may select an oral administration of polynitroxide dextran as the electron acceptor and an oral and/or intravenous administration of membrane permeable TEMPOL. As a further example, to treat psoriasis, a localized skin condition where free radical generation is manifested, one may select a topical application of TOPS as the electron acceptor and a topic application of membrane permeable TEMPOL. By any similar rationale, site specific protection or activity can be provided using the formulation of this invention for other disease states, or diagnostic or therapeutic state where free radical species are present. Therefore, the following examples disclose a detailed description of several formulations which can be used in any combination depending on the application to which this invention is applied.

EXAMPLE ONE

Containers and Filters Containing Nitroxides and Nitroxide-Labelled Compounds It is possible to provide the oxygen-detoxification function of this invention to existing intravenous solutions, such as the HBOC solutions, without chemically modifying the existing formulations. By including a polynitroxide macromolecule, which may be used in connection with a free nitroxide, or by covalently attaching nitroxides to a surface inside the vessel in which the HBOC is stored, the adverse physiological effects caused by oxygen toxicity that are observed with the existing formulations will be alleviated.

The container used with the hemoglobin-containing solutions that are the subject of this invention should be physiologically compatible having similar characteristics as any container to be used with intravenous fluids. Typically, glass or a biocompatible plastic is suitable. For the embodiments of the invention where an intravenous solution is placed in a container for any length of time, the container should be oxygen free and capable of being sealed to exclude oxygen. With a glass container, a traditional stopper and closure means is sufficient. However, some of the flexible plastic containers currently available are oxygen permeable. In this case, a foil overwrap or other sealing mechanism may be used to prevent oxygen from contacting the solution.

To apply a nitroxide to an inner surface of a container, a non-leaching layer of a nitroxide polymer or a nitroxide-doped copolymer is coated directly on the inner surface. Nitroxide-containing polymers can be created by a number of techniques based on generally known principles of polymerization as long as the stability of the free radical is maintained in the polymerization process.

Also, the interior surface of an HBOC container may be modified to contain a coating layer of a substance that can bind a nitroxide, such as hydrophilic hydrazide groups which will react with the ketone or the aldehyde group of a nitroxide to form stable hydrazone derivatives. The coating reaction is straight forward. For example, the nitroxide (100 mM) in acetate buffer at pH 5.0 is added to a hydrazide activated plastic container to facilitate the formation of a hydrazone linkage.

Once the container is prepared, a physiologically compatible solution is added. This solution may be a stabilized and purified HBOC or the HRCS disclosed herein, and could also include any intravenous colloid or crystalloid solution that is desirable to co-infuse with hemoglobin. The solution is then maintained in an essentially oxygen-free environment.

In addition to treating a surface inside a container, a filter-type cartridge, with a luer lock inlet and outlet, containing a gel or solid matrix upon which a nitroxide is immobilized may be used to remove reactive oxygen-derived species while the hemoglobin solution passes through the cartridge. For such an administration technique, a polynitroxide macromolecule may be added into the housing of the filter through which a solution passes for direct infusion into a patient to react with the solution before infusion. A low molecular weight nitroxide may also be included. In these applications, nitroxide may also be bound to a soft- or hard-gel matrix, thereby functioning essentially as a sterile in-line filter, prior to infusion. A variety of methods to attach small ligands, such as nitroxide, to a solid matrix are well known in the art of affinity chromatography, as are the techniques to chemically modify glass and plastic surfaces. Several types of matrices that are compatible with sterile solutions are known including agarose gel, polysulfone-based material, latex, and others.

Figure 12:
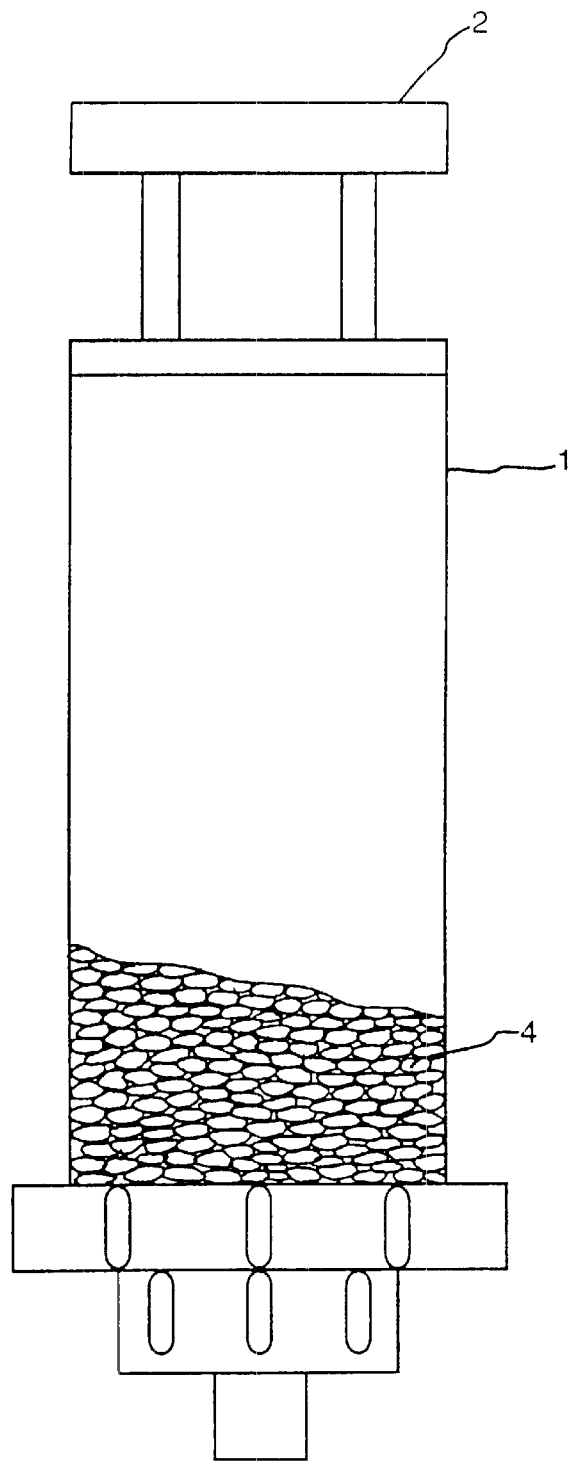
FIG. 12 is an embodiment of a filter cartridge that contains a solid matrix to which a nitroxide is bound and through which a hemoglobin-containing solution may be passed.

In the filter cartridge approach, the solid matrix is covalently linked with a nitroxide and contained in a filter housing or other such apparatus such that a solution, such as hemoglobin can flow through the apparatus and be brought into contact with a nitroxide while being infused into a patient. A practical approach is to use a commonly available activated agarose gel as the matrix and contain the gel in a sterile luer lock cartridge. The cartridge is then simply inserted in the fluid administration line during the transfusion of a solution containing hemoglobin. In practice, the structure that comprises the filter housing in which the nitroxide and through which hemoglobin is passed can be provided by a variety of known structures. See e.g., U.S. Pat. No. 5,149,425. Referring now to FIG. 12, housing 1 contains a nitroxide-labelled agarose gel. For example, a 4-bromoacetamido-TEMPO labelled ω-aminohexyl-agarose (See FIG. 2A) a 1,4-bis(2,3-epoxypropoxy)butane agarose coupled with 4-amino-TEMPO (See FIG. 2B). Other compounds (not shown) may be included with the filter housing.

Figure 2A:
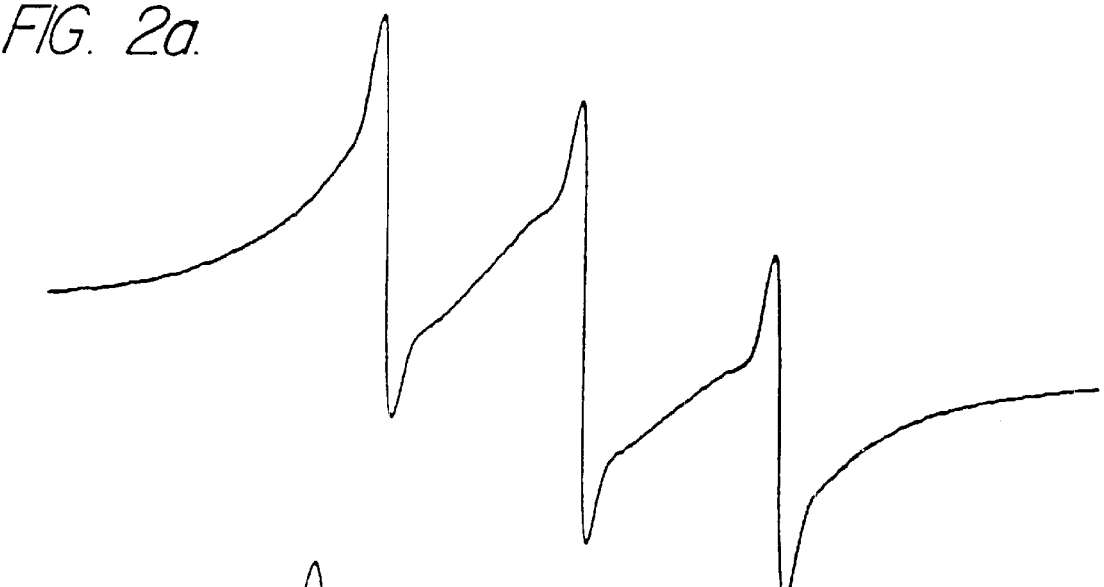
FIGS. 2A and 2B are, respectively, the electron spin resonance spectra demonstrating covalent attachment of 4-(2-bromoacetamido)-TEMPO to ω-aminohexyl-agarose and 4-amino-TEMPO to 1,4-bis(2:3-Epoxypropoxy) butane-activated agarose.
Figure 2B:

During the transfusion, the intravenous transfusion line containing the solution would be connected to the luer inlet 2 allowed to enter the housing 1 wherein the hemoglobin solution would encounter the nitroxide-containing compounds contained within the housing or bound to the matrix 4, in this process, the nitroxide-containing compositions will be infused and may react to remove the toxic oxygen-related species from solution. The hemoglobin solution would then pass out of the cartridge through the luer outlet 3 and would be directly transfused into a patient. The electron resonance spectrum of 4-amino-TEMPO labelled epoxy-agarose is shown in FIG. 2A. Alternatively, an ω-aminohexyl-agarose may be reacted with 4-(2-bromoacetamido)-TEMPO to form TEMPO labelled agarose. The electron spin resonance spectrum is shown in FIG. 2B. An alternative would be to couple the 4-carboxyl-TEMPO to the amino-agarose with carbodiimide via a carboamide linkage. Conversely, the 4-amino-TEMPO is readily coupled to the carboxyl group on an agarose gel using carbodiimide, for example, 1-ethyl-3-(3-dimethylamino-propyl)carbodiimide.

The cartridge labelled with 4-amino-TEMPO is prepared by circulating a 100 mM 4-amino-TEMPO (Sigma Chem. Co.) in a Lactated Ringers solution through an aldehyde AvidChrom Cartridge (Unisyn Tech. Inc.) at room temperature for one hour followed by the reduction with sodium cyanoborohydride for six (6) hours. The interior of the cartridge housing is thoroughly washed with Lactated Ringers.

The cartridge labelled with 3-amino-PROXYL may be similarly prepared by substituting 4-amino-TEMPO with 3-amino-PROXYL according to the procedure described above.

EXAMPLE TWO

Nitroxide-Labelled Stabilized Hemoglobin

To prevent dissociation of hemoglobin into its constituent subunits, hemoglobin is intramolecularly stabilized by chemical or recombinant cross-linking of its subunits. "Stabilized" hemoglobin is referred herein to describe hemoglobin monomers that are stabilized by chemical or recombinant cross-linking and also to describe dimers, trimers, and larger oligomers whose constituent hemoglobin molecules are stabilized by cross-linking with cyclodextrans and their sulfated derivatives.

A preferred technique for attaching nitroxide to stabilized hemoglobin is by the covalent attachment of the nitroxide to the β-93 sulfhydryl groups of the two β-chains of stabilized hemoglobin. Although specific labelling at the β-93 site has been demonstrated on native human hemoglobin for conformational studies (See review by McConnell et. al., Quart. Rev. Biophys. 3:91 (1970)), such a specific labelling of cross-linked hemoglobin has not been reported. As noted above, several types of hemoglobin-based oxygen carriers have been developed that are stabilized through chemical cross-linking, for example, DBBF-cross-linked hemoglobin and hemoglobin that is stabilized and oligomerized with o-raffinose.

The ring-opened sugars described in my U.S. Pat. No. 4,857,636 yield polyvalent aldehydes derived from disaccharides, oligosaccharides, or, preferably, trisaccharides such as o-raffinose. These compounds function both to provide intramolecular stabilization (cross-linking) and intermolecular polymerization. By controlling the reaction disclosed in my earlier patent, the polyvalent aldehydes may be used to produce "stabilized" hemoglobin as defined above without polymerization. In another case, a nitroxide may be covalently bound to the stabilized hemoglobin or the polymerized hemoglobin. Therefore, the hemoglobin-based solutions that are stabilized using the polyvalent aldehydes are considered in the present embodiment as a "stabilized" hemoglobin and in the subsequent embodiment as a polymerized hemoglobin.

To demonstrate, that the β-93 site of the chemically modified hemoglobin has not been rendered sterically inaccessible for nitroxide attachment, results are presented to confirm that a nitroxide may be covalently bound to the β-93 site of DBBF-Hb.

In this embodiment, DBBF-Hb is reacted with two types of nitroxides (TEMPO and PROXYL) which contain two types of sulfhydro group specific functional groups and have the following structural formula:

(I)
4-(2-Bromoacetamido)-TEMPO

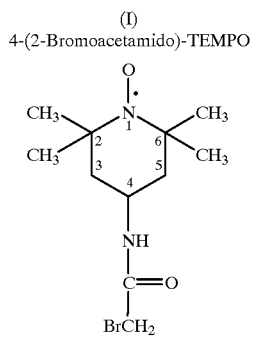

-continued (II)
3-Maleimido-PROXYL

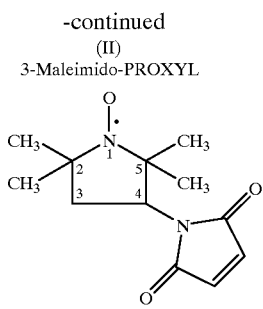

Figure 3A:
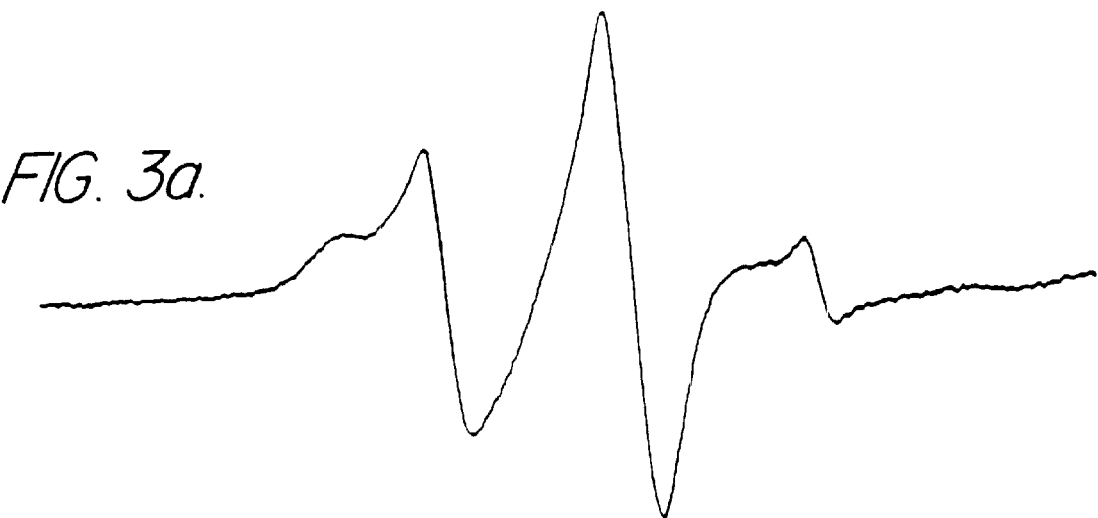
FIGS. 3A and 3B, respectively, are electron spin resonance spectra demonstrating successful covalent attachment of 4-(2-Bromoacetamido)-TEMPO and 3-maleimido-PROXYL to 3,5-bis-bromosilicyl-bisfumarate (DBBF) cross-linked or diaspirin cross-linked human hemoglobin (HBOC).
Figure 3B:
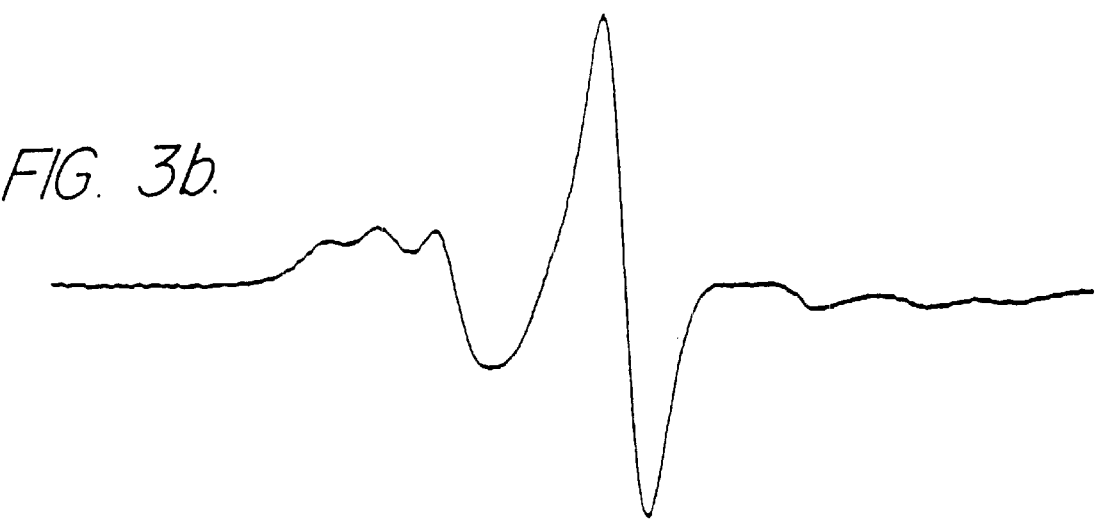

DBBF-Hb is prepared by cross-linking purified deoxygenated hemoglobin in solution with bis(3,5 dibromosalicyl) fumarate by known techniques, and the resulting product is purified by column chromatography. The covalent attachment of 3-maleimido (2,2,5,5-tetramethyl pyrrolidine-N-Oxyl) [3-maleimido-PROXYL] is accomplished by adding 2 molar equivalents of this nitroxide using methanol as the carrier solvent at a concentration of approximately 100 mM of 3-maleimido-PROXYL to 1 ml of DBBF-Hb at a concentration of approximately 8 g/dl in Lactate Ringers. The DBBF-Hb is allowed to react at 22–23° C. for approximately 30 minutes with mixing. The extent of cross-linking is estimated from the percent disappearance of the electron spin resonance signal intensity of the unreacted nitroxide. To remove the unreacted nitroxide, the reaction mixture was washed three (3) times with a 10 volume excess of Lactated Ringers using a Filtron stire cell with a 30 kilodalton cut-off nominal molecular weight limits (NMWL) polyethylene sulfone (PES) membrane (Filtron Technology Co.). The electron spin resonance measurements of the nitroxide-labelled hemoglobin was recorded with a Bruker ESR spectrometer. FIG. 3A shows the electron spin resonance spectra of 4-(2-bromoacetamido)-TEMPO labelled DBBF-Hb. The electron spin resonance spectrum of DBBF-Hb that is similarly labelled with 3-maleimido-PROXYL is shown in FIG. 3B.

In this embodiment, the nitroxide is covalently linked to the lone sulfhydro group on the two β-globin chains of hemoglobin. Thus, the nitroxide to hemoglobin-bound oxygen ratio is approximately 200 to 1 at 99.00% deoxyhemoglobin because there are two nitroxides attached to the two β-globin chains of the hemoglobin. After transfusion, however, the deoxygenated HRCS picks up oxygen in the lung and the nitroxide to hemoglobin-bound oxygen ratio becomes approximately 1 to 2 at 100% oxygenation because there are four oxygen molecules bound to the four globin chains of the hemoglobin with the two nitroxides remaining on the β-globin chains.

Using a hemoglobin-to-nitroxide ratio of 1:2, greater than 90% of the nitroxide is covalently attached to the DBBF-Hb. DBBF-Hb may also be covalently labelled with a spacer group (e.c., an extra methyl group) between the maleimido and PROXYL moieties (i.e., 3-maleimidomethyl-PROXYL) which would exhibit a resonance spectrum similar to that of FIG. 3B. It is noteworthy that other nitroxides may be covalently attached to specific amino-groups in the DPG binding site (e.g., β-Val-1 β-Lys-82 and α-Lys-99) or may be attached to the remaining 40-plus surface lysine ε-amino groups on hemoglobin. Isothiocyanate derivatives of the TEMPO and PROXYL nitroxides are also reactive with the amino group. For example, 4-isothiocyanate-TEMPO may be added to hemoglobin at a molar ratio of approximately 10:1. Resonance spectrum (not shown) of hemoglobin labelled with this nitroxide at other sites is similar to that shown in FIG. 3A.

The ability to attach nitroxides at several sites of DBBF-Hb suggests that recombinant hemoglobin that is stabilized with alphaglobin dimers (D. Looker et.al. NATURE 356:258 (1992)) may be similarly labelled with a nitroxide. It is also possible to prepare a DBBF analogue of a nitroxide-labelled cross-linking agent such as a TEMPO labelled succinate (See U.S. Pat. No. 4,240,797).

Figure 4A:
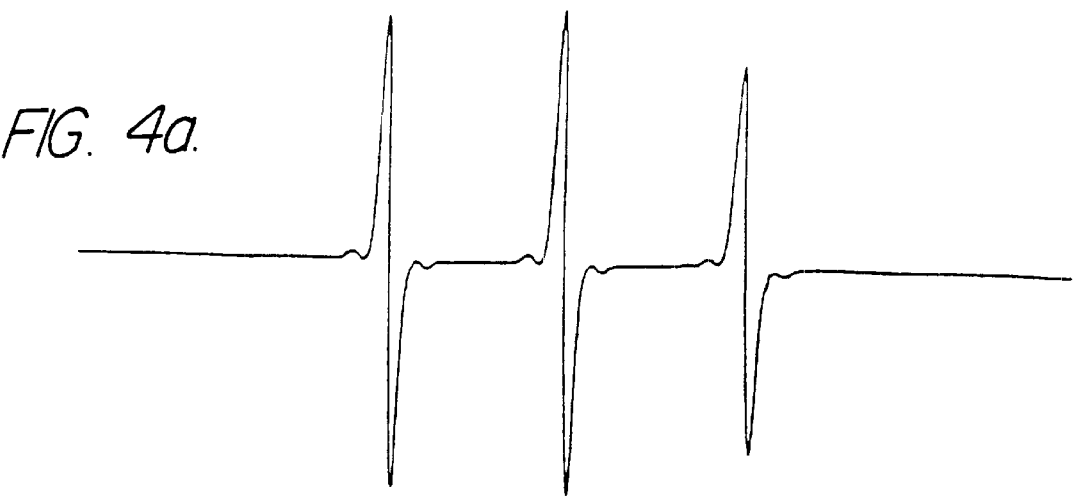
FIG. 4A is an ESR spectra of 4-(2-bromoacetamido)-TEMPO.
Figure 4B:
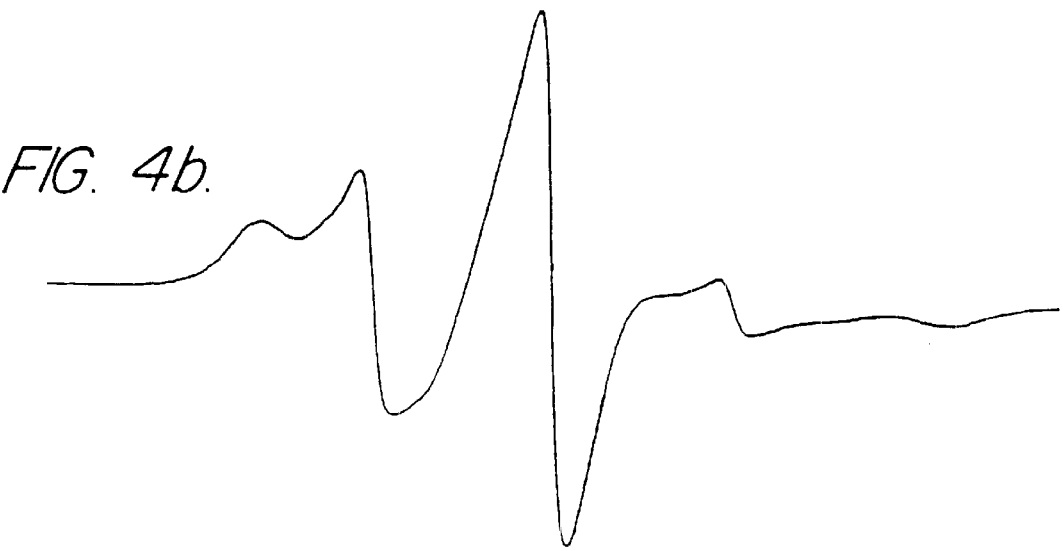
FIG. 4B is an ESR spectra of 4-(2-bromoacetamido)-TEMPO-labelled HBOC.
Figure 4C:
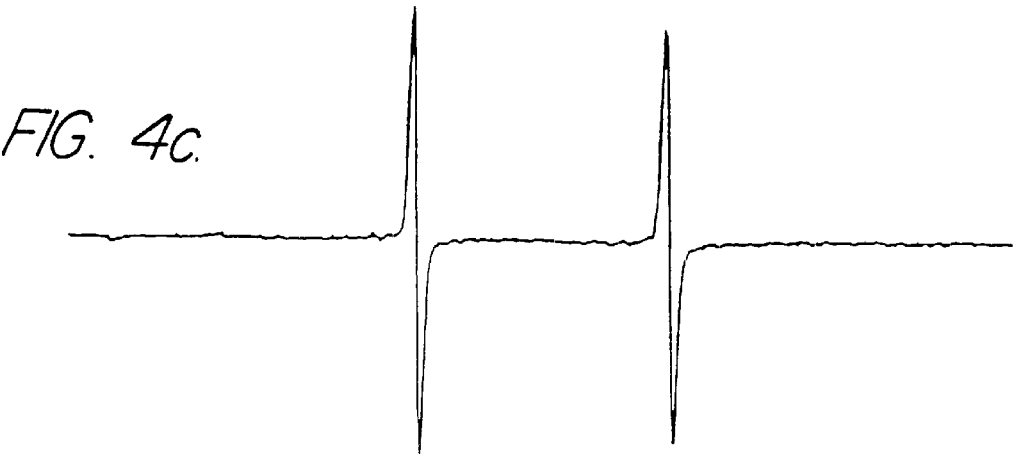
FIG. 4C is an ESR spectra of $^{15}ND_{17}$ TEMPOL in Lactated Ringer's solution recorded at room temperature.

FIG. 4 is ESR spectra of (A) 2-(bromoacetamido)-TEMPO, (B) 2-(bromoacetamido)-TEMPO-labelled HBOC and (C) $^{15}ND_{17}$ TEMPOL (TEMPOL: 4-hydroxy-2,2,6,6-tetramethylpiperidine-1-oxyl) in Lactated Ringer's solution recorded at room temperature. The difference in FIGS. 4A and 4B represents the difference in the mobility of a small molecular weight nitroxide to that of a nitroxide covalently attached to a macromolecule such as hemoglobin. FIG. 4C shows that a stable isotope nitrogen $^{15}N$ with a nuclear spin of ½ yields two resonance peaks and that natural-isotopic $^{14}N$ with a nuclear spin of 1 yields three resonance peaks (compare (4A to 4C). In the set of experiments described here the separation of these resonance peaks is used to demonstrate the enzyme-mimic and in vivo and in vitro oxidation/reduction reactions of small and macromolecular weight nitroxides.

Nitroxide-labelled HBOC with different molar ratios of nitroxide to hemoglobin are prepared as follows. 2, 4, and 8 molar equivalents of 4-(2-bromoacetamido)-TEMPO, were added as solid powder directly into three separate 15 ml Vacutainers in a clean hood. After replacing the rubber septum, 4-(2-bromoacetamido)-TEMPO was subsequently dissolved in 200 ul chloroform. The Vacutainers were then connected to high vacuum (5 mm Hg) via a 27 gauge needle through the rubber septum and the chloroform was removed leaving a thin film of 4-(2-bromoacetamido)-TEMPO coating the lower half of the Vacutainer. After introducing the appropriate amount of HBOC via sterile transfer through the rubber septum, the solutions were allowed to react at room temperature with intermittent vortex mixing at approximately 5 minute intervals for ½ hour (not all solids were dissolved in the 4 and 8 molar ratios of nitroxide to hemoglobin), the Vacutainers were then left at 4 degrees C. in a refrigerator over night. Vortex mixing at room temperature was resumed the next morning for another ½ hour until all solids of 4-(2-bromoacetamido)-TEMPO had visually disappeared from the surface of the Vacutainer.

Figure 5A:
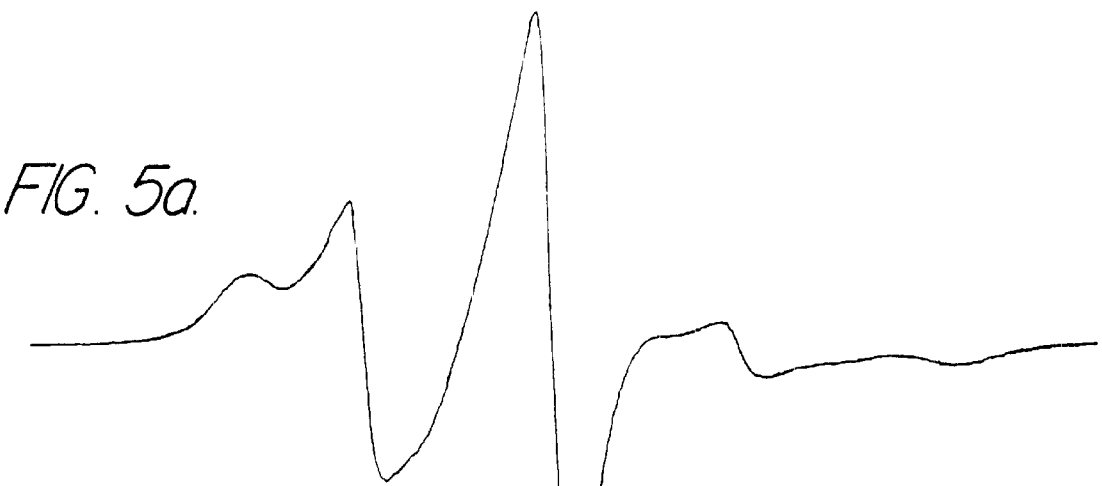
Figure 5B:
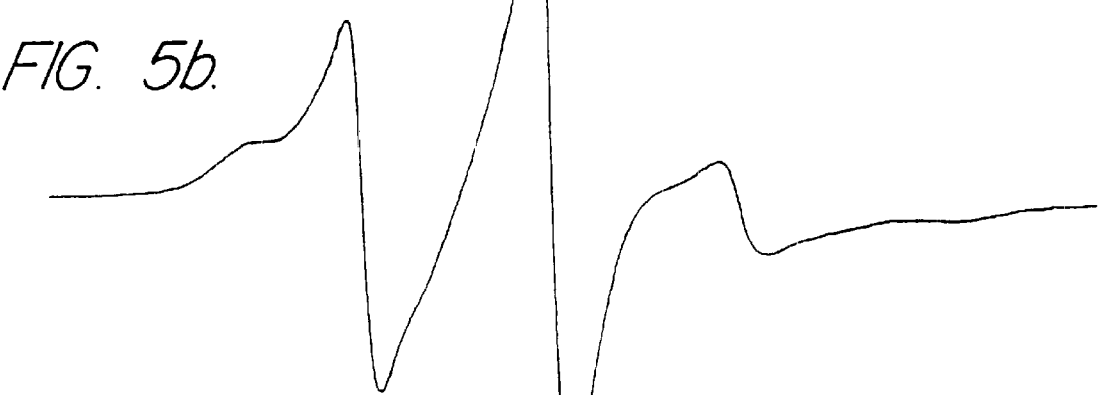
Figure 5C:
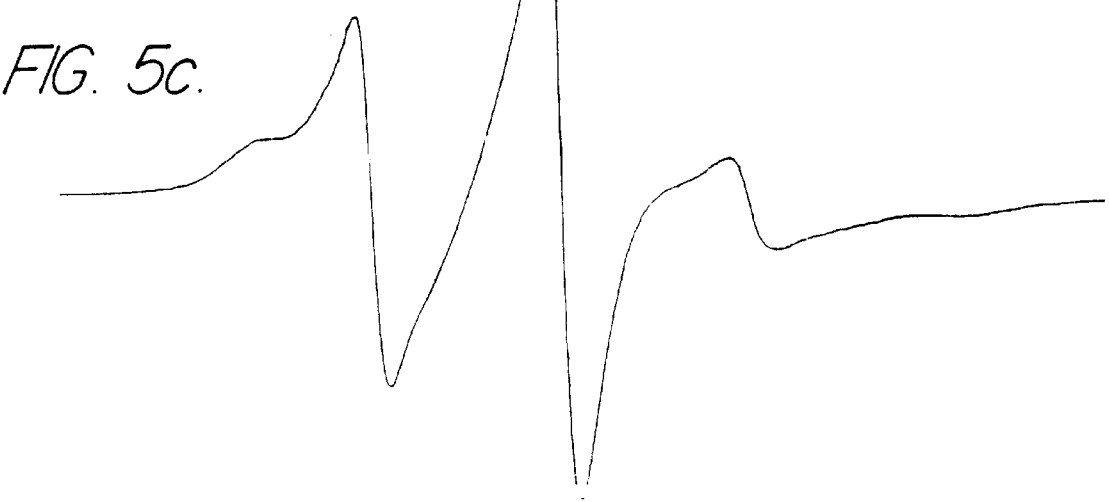

The reaction mixtures and the control, were then transferred to a sterile dialyzing tube and dialyzed against Lactated Ringers until no unlabelled free 4-(2-bromoacetamido)-TEMPO electron spin resonance (ESR) signals could be detected. The ESR spectra of 4-(2-bromoacetamido)-TEMPO-labelled HBOC at 2, 4, and 8 molar equivalents 4-(2-bromoacetamido)-TEMPO to Hb are shown in FIGS. 5A–5C respectively. At 2 molar equivalents of 4-(2-bromoacetamido)-TEMPO to hemoglobin, the ESR spectra are essentially the same with or without dialysis indicating the covalent labeling is quantitative. The two SH— groups on the beta globulin chains appear to be the site of covalent attachment in the case of HBOC (this can be confirmed by selective blocking of 4-(2-bromoacetamido)-TEMPO labeling with N-ethyl-maleimide or globulin chain analysis by reverse phase HPLC). It is noteworthy that the ESR signal intensity (peak Mo) ratios for 2, 4, and 8 are in approximately the same ratio as the spectra were recorded at proportionately decreasing instrument sensitivity.

Furthermore, it is expected that more 4-(2-bromoacetamido)-TEMPO could be attached to Hb at even higher molar ratios, for example as radiation-protective agents in vivo.

A preferred molar ratio of nitroxide to hemoglobin in the blood substitute formulations is 8:1 and a particularly preferred molar ratio is approximately 18, prepared as described below to yield a polynitroxide hemoglobin (PNH). A preferred formulation of PNH is the carbonmonoxyl derivative, CO—PNH. CO binding to PNH heme groups stabilized PNH: its has been shown that CO—PNH is stable to heating at 60° C. Therefore, CO—PNH requires no refrigeration and can be stored at room temperature for a prolonged period of time. Furthermore, when infused into the body, the presence of CO enhances the vasodilatory activity of PNH, a CO is known to act as a vasodilator in vivo. After the CO has been off-loaded from PNH, PNH continues to function as a therapeutic agent, both by delivering oxygen to tissue and through its nitroxide-mediated vasodilation.

Figure 6:
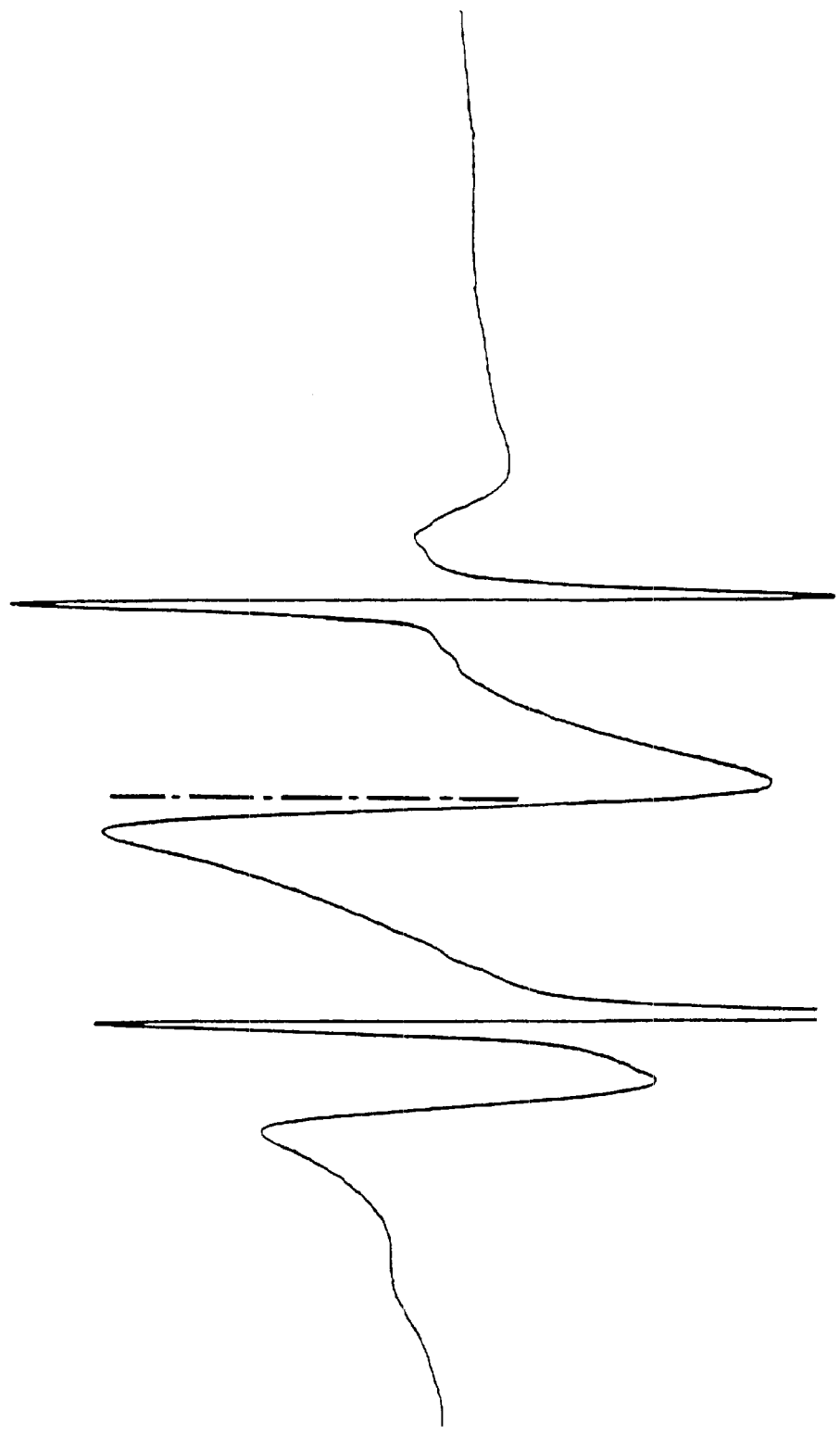
FIG. 6 is an ESR spectrum of a mixture of 4-(2-bromoacetamido)-TEMPO labelled HBOC and $^{15}ND_{17}$-TEMPOL wherein the center peak (see down arrow) of the former and the high field peak (see up-arrow) of the latter were adjusted to similar intensity. This is a superimposition of ESR spectrum from FIG. 4B and FIG. 4C.

Referring to FIG. 6, an ESR spectrum of a mixture of 4-(2-bromoacetamide)-TEMPO-labelled HBOC and $^{15}ND_{17}$-TEMPOL wherein the center peak of the 4-(2-bromoacetamido)-TEMPO (indicated by down arrow) and the high field peak of $^{15}ND_{17}$-TEMPOL (indicated by the up-arrow) were adjusted to similar intensity.

The separation of the resonance peaks permits the simultaneous monitoring of free radical or enzyme mimic activities involving the small molecular weight nitroxide (TEMPOL) and its macromolecular conjugate in both in vitro and in vivo (murine) reactions. For example, the in vivo plasma half-life of the two nitroxides was compared by referring to the unique spectral characteristics of the different nitroxides. Specifically, the in vivo ESR studies of hemoglobin-based solutions, on the mouse were performed using a nitroxide to hemoglobin ratio of 8:1 (see FIG. 5C) to take advantage of its high ESR signal intensity. First, the approximate plasma half-life of a small molecular weight nitroxide ($^{15}ND_{17}$-TEMPOL see FIG. 4C) and a large molecular weight 4-(2-bromoacetamido)-TEMPOL-labelled HBOC (see FIG. 4B) are determined by preparing a mixture of the two and adjusting the ESR signal intensity to be approximately the same (see FIG. 6). 0.5 ml of the mixture was injected under anesthesia into a distended mouse tail vein under a heat lamp. The mouse tail was inserted into an ESR cavity and the spectrum was recorded within 10 minutes after injection (see FIG. 7A).

Figure 8A:
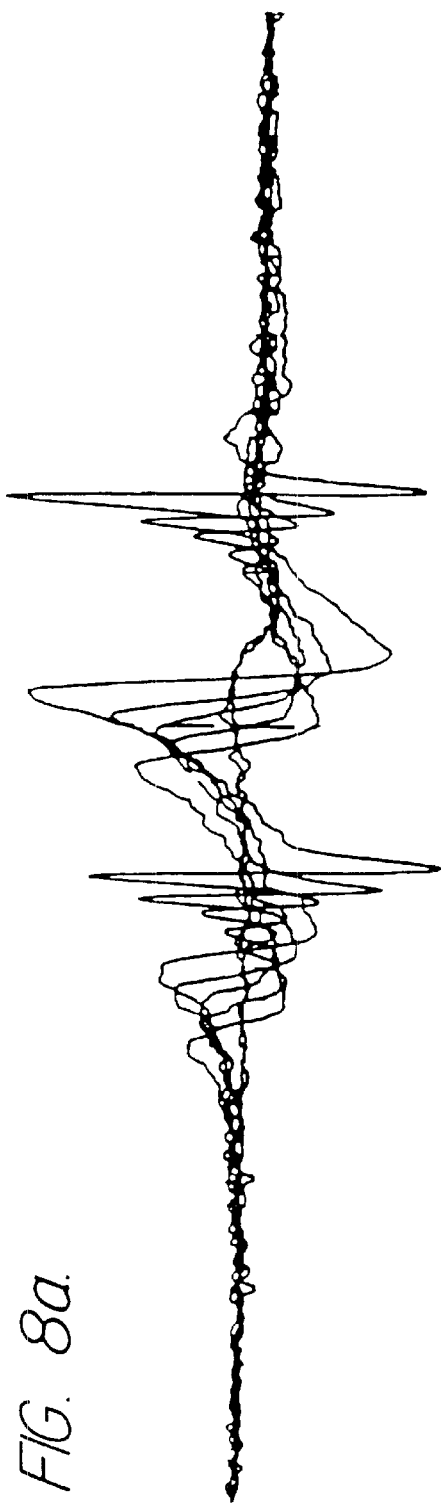
FIG. 8A is a series of 5 ESR spectrum recorded at 0.5 minute intervals, the magnetic field strength was increased by 2 Gauss in between each scan to display the decrease in signal intensity as a function of time.

Referring to FIGS. 7A, 7B, and 7C the $^{15}ND_{17}$-TEMPOL signal could not be detected, however, the 4-(2-bromoacetamido)-TEMPO-labelled HBOC was clearly resolved (see FIGS. 7B and 7C for plasma half-life studies where 7C is a continuation of 7B). Since the vasoconstrictive effect of HEOC is reported to be fully developed during the first 5–15 minutes of bolus injection of an HBOC in rats, the participation of the nitroxide-labelled HBOC in free radical redox-reactions immediately after transfusion in a mouse was measured. The tail vein of female CH3 mouse was cannulated under anesthesia with 80% nitrous oxide, 20% oxygen, and 3% isofluorane. Under a heat lamp the mouse tail vein became visibly distended, a cannula consisting of a 30 gauge hypodermic needle attached to a one foot length of polyethylene tubing was inserted into the tail vein and held in place by cyanoacrylate glue. For in vivo ESR measurements, the cannulated mouse was transferred under anesthesia to a 50 ml conical centrifuge tube modified to allow the tail to protrude from the conical end and to allow a continuous flow of anesthetic gas from the opening end of the tube. The tail was inserted into a plastic tube which was then fitted into a TE 102 cavity. The cannula was flushed periodically with heparin (100 unit/ml) to ensure patency. The cannula was near the root of the tail and was kept outside of the ESR cavity so that a pure signal from the tail could be measured immediately after bolus injection. 0.5 ml of samples (see FIG. 8) were injected via the cannula and the spectrometer was set for a repeat scanning mode at ½ min. intervals (see FIGS. 8A and 8B). In FIG. 8A the magnetic field was increased by two Gauss, and in FIG. 8B the magnetic field was decreased by two Gauss, to superimpose the resonance spectra. The $^{15}ND_{17}$-TEMPOL signal disappeared within 2.5 minutes after injection. During the same time period the 4-(2-bromoacetamido)-TEMPOL-labelled HBOC also decreased at a similar rate.

Figure 8B:
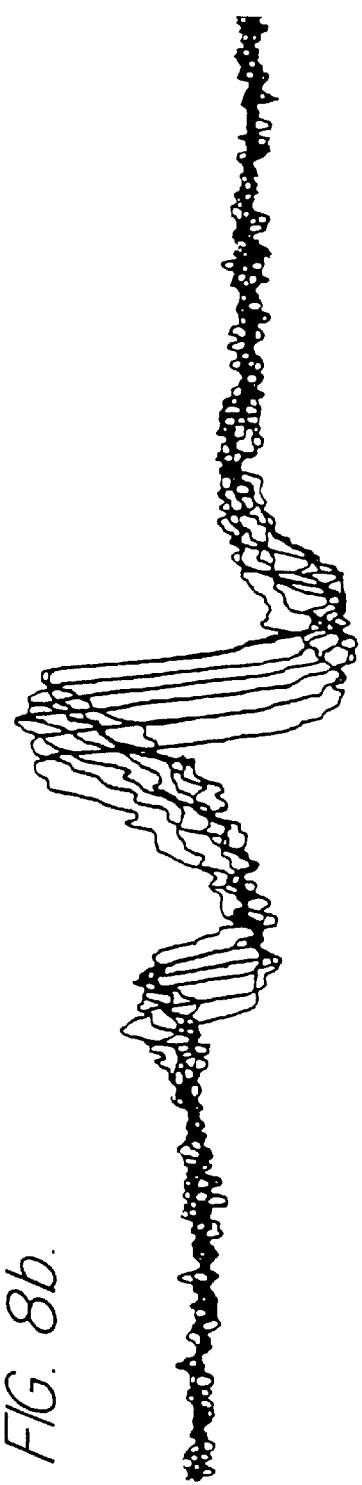
FIG. 8B is the continuation from FIG. 8A of repeated recording of a series of 6 ESR spectrum at the same time intervals except that the magnetic field strength was decreased by 2 Gauss in between each scan.

However, the nitroxide-HBOC signal were shown to be stable in plasma (FIG. 8B). Therefore, FIG. 8B together with results from FIG. 7 show that the nitroxide-labelled to macromolecules such as HBOC has considerably longer plasma half-life as compared to small molecular weight nitroxide (e.g., $^{15}ND_{17}$-TEMPOL).

The observed nature of the free radical reaction involves two pathways:

1. the rapid phase appears to involve the free radical (e.g. superoxide) oxidation of the nitroxide to its oxoammonium cation intermediate followed by the reduction of the oxoammonium cation to its stable hydroxylamine derivative of the nitroxide. Such reduction involves the participation of either one or two reducing equivalents (e.g. NADH) present in the vascular compartment. The reduction of nitroxide to its hydroxylamine would lead to a rapid reduction in ESR signal intensity, in the case of 8:1 molar ratio of 4-(2-bromoacetamido)-TEMPO-labelled HBOC represents approximately 25% of the 4-(2-bromoacetamido)-TEMPO on the HBOC. This phase involves both small molecule and macromolecular nitroxide.

2. the slow phase appears (see FIG. 8B) to represent the antioxidant enzyme-mimic activities of the remaining 75% of 4-(2-bromoacetamido)-TEMPO on the HBOC in accordance with the reaction mechanism wherein the nitroxide is involved in the cyclic-free radical reactions for example the SOD-mimic reaction. Where the nitroxide free radical is essentially unconsumed as a SOD-mimic, the slow rate of decrease of the ESR signal intensity can be attributable primarily to the reaction mechanism described above and secondarily to the decrease in HBOC concentration as it is slowly eliminated from the vascular compartment as a function of its plasma half-life.

This result demonstrates the utility of polynitroxide macromolecule, in this example TEMPO-labelled HBOC, in detoxifying free radicals in vivo. This utility is defined in terms of providing short term (in minutes) scavenging of free radicals and persistent (in hours) protection against oxidant reactions by nitroxides acting as enzyme mimics in vivo. In this and each of the examples related to hemoglobin-containing solution should be understood that unbound, low molecular weight nitroxide may be added to the formulation to increase the concentration of active nitroxide across the vascular membrane, into the interstitial space, and the surrounding cellular environment. The results presented here thereby distinguish the effect of a simple addition of a low molecular weight nitroxide to a pharmaceutical composition from the polynitroxide macromolecules of this invention. The particular advantages of a multi-component system of this invention utilizing a polynitroxide macromolecule together with molecular weight nitroxides is highlighted below.

Based on the analysis of the spectra in FIG. 8, the oxidation/reduction (redox) cycling reactions involve approximately 73% of 4-(2-bromoacetamido)-TEMPOlabelled HBOC remaining in its free radical state. This indicates that TEMPOL participates in in vivo redox-reactions within the confines of the vascular space.

To study the vasoconstrictive effects of hemoglobin-based solutions, solutions of modified human hemoglobin are tested for their effects in the intact rat. Humane procedures are always used where any research animals are used.

At 7 days prior to the study, male Sprague-Dawley rats are anesthetized with ketamine (40 mg/kg i.m.) and acetylpromazine (0.75 mg), or with pentobarbital sodium (20 mg/kg i.p.). Medical grade Tygon microbore (0.05 in ID, 0.03 in OD) is inserted into the femoral artery and veins. Cannulas are exteriorized and filled with heparinized dextrose, and sealed with stainless steel pins. After a 2–3 day recovery period, conscious animals will are in plastic restraining cages. Seven (7) days recovery from surgical procedure are needed to ensure healing of incisions before exchange transfusion. Because the surgery may cause minor bleeding, it is important to permit recovery so that minor bleeding related to surgery is not confused with a side effect of blood replacement. 50% exchange transfusions are carried out using an infusion pump to simultaneously infuse and withdraw the test solution and blood, respectively, from two syringes. The volume of blood removed (12–15 ml based on total blood volume) is replaced with test solution over approximately 20–30 minutes. The end point is the reduction of the hematocrit to half its initial value. The arterial blood pressure is monitored and recorded continuously for 5 hours after the exchange transfusion using a pressure transducer connected to a chart recorder. Mean arterial pressure is calculated as $\frac{1}{3}$ of the pulse pressure. Heart rate is determined from the blood pressure trace.

EXAMPLE THREE

Nitroxide-Labelled Polymers of Stabilized Hemoglobin

While it is possible to produce dimers of stabilized hemoglobin from cross-linked monomers, it is also possible to produce hemoglobin polymers from stabilized or native hemoglobin. Solutions of hemoglobin polymers contain a mixture of monomers, dimers, trimers, tetramers, and other oligomers. Solutions containing polymerized hemoglobins used as an HBOC generally have longer plasma circulation times and higher oxygen carrying capacities as compared to stabilized monomeric hemoglobin. Such polymerized hemoglobin may be prepared by a number of pathways using several different polymerizing agents. (See, U.S. Pat. Nos. 4,001,200, 4,857,636, and 4,826,811). The preferred method of introducing a nitroxide to a solution of polymerized hemoglobin is again by covalently attaching a nitroxide to the β-93 sulfhydryl groups of the two β-globin chains of hemoglobin. These sulfhydryl groups are not known to be involved in the stabilization or polymerization processes. Consequently, the nitroxide is preferably covalently attached to hemoglobin before the stabilization and polymerization of the hemoglobin monomers.

For example, nitroxide is covalently attached to DBBF-Hb according to the procedure described in the second embodiment above, followed by polymerization with glutaldehyde according to the procedure described in Sehgal et. al. U.S. Pat. No. 4,826,811. FIG. 4B is an electron spin resonance spectra of the DBBF-Hb labelled with 3-maleimido-PROXYL and polymerized with glutaldehyde. Similarly, DBBF-Hb that is polymerized with glutaldehyde may be labelled with 4-(2-bromoacetamido)-TEMPO by the same method.

Figures 9A, 9B:
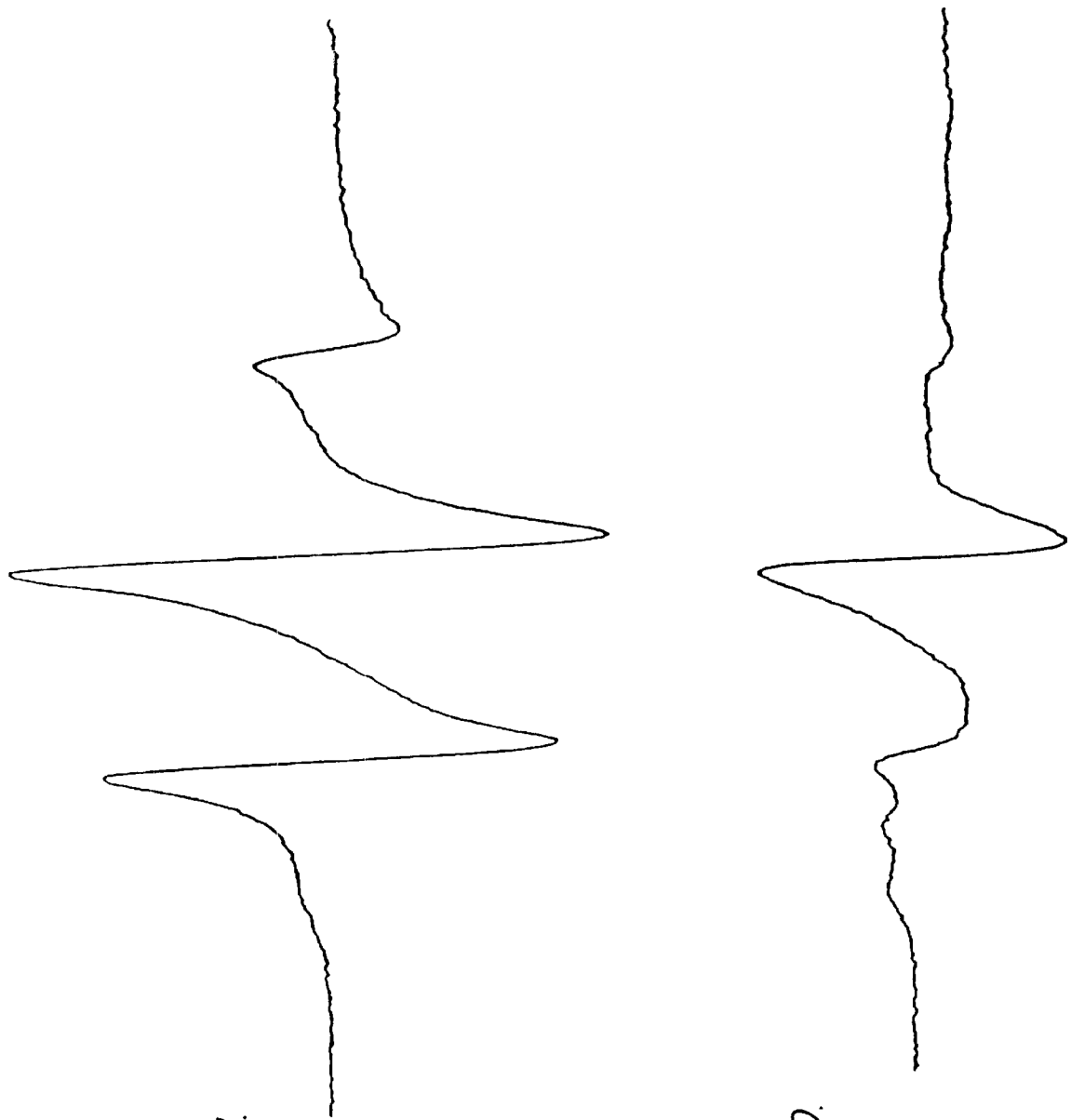
FIGS. 9A and 9B, respectively, are electron spin resonance spectra demonstrating 4-amino-TEMPO labelled and o-raffinose cross-linked and polymerized human hemoglobin and 3-maleimido-PROXYL labelled DBBF-hemoglobin polymerized with glutaldehyde.

Using a similar approach, a polymerized hemoglobin intermediate, such as a glutaldehyde-polymerized, an o-raffinose-polymerized, or an o-cyclodextran-polymerized hemoglobin intermediate that contains unreacted aldehyde groups, may be used for covalent attachment of either 4-amino-TEMPO or 3-amino-PROXYL via reductive amination to yield a nitroxide-labelled hemoglobin polymer. With reductive amination, the sequence and timing of the reaction are important. The 4-amino-TEMPO is added to glutaldehyde-polymerized hemoglobin after completion of polymerization, but prior to the reduction reaction that results in covalent attachment of the nitroxide to the polymerized hemoglobin. Likewise, the nitroxide-labelling of a o-raffinose polymerized hemoglobin may be accomplished by the addition of either 4-amino-TEMPO or 3-amino-PROXYL prior to reductive amination. For example, 4-amino-TEMPO labelled o-raffinose polymerized hemoglobin is prepared according to the procedure described in my U.S. Pat. No. 4,857,636 except that 6 molar equivalents of 4-amino-TEMPO is added after the completion of the polymerization and prior to the reduction with 20 molar excess of borane dimethylamine complex. As described therein, hemoglobin may be cross-linked and polymerized using polyvalent aldehydes derived from disaccharides or ring-opened sugars including, oligosaccharides, or preferably, trisaccharides such as o-raffinose. Likewise, monosaccharides may be used to stabilize and polymerize hemoglobin although the higher molecular weight sugars are preferred. The resonance spectrum of a dialyzed and washed o-raffinose polymerized hemoglobin labelled with 4-amino-TEMPO was shown in FIG. 9A.

To increase the yield of hemoglobin oligomers ($Hb_n$ where n=2–4) of the polymerized hemoglobin, it is desirable to increase the valance of the polyaldehyde of the cross-linker, with the use of α-cyclodextran, β-cyclodextran, and γ-cyclodextran, as well as their sulfate derivatives which represents 6-, 7-, and 8-cyclized glucose molecules, the ring opened α-cyclodextran, β-cyclodextran, and γ-cyclodextran have 12, 14, and 16 reactive aldehyde groups respectively. These ring-opened cross-linkers can be used to cross-link and polymerize hemoglobin to produce polymerized hemoglobin which is rich in oligomers. The unreacted aldehyde, as described above, may be utilized to covalently attached to an amino-nitroxide, for example, 4-amino-TEMPO or 3-amino-PROXYL.

Furthermore, the ring-opened sulfate derivatives, for example, the sulfated α-cyclodextran will be an effective cross-linker for two additional reasons: (1) the sulfate groups will mimic the activity of DPG in lowering the oxygen affinity of the cross-linked hemoglobin, thus improving oxygen transport properties, and (2) the sulfate groups will serve as affinity labels which will complex multiple (e.g., n=2–4) hemoglobins to initially form a "cluster." Once the "cluster" complex is formed, the aldehyde groups on the cyclodextran will be brought to close proximity with the $NH_2$ groups within the DPG binding sites, thus promoting the covalent intra-subunit and intermolecular cross-linking of hemoglobin resulting in an increased yield of hemoglobin oligomers. In addition to antioxidant enzyme-mimic activities, the ring-opened cyclodextran polymerized and nitroxide-labelled hemoglobin will also have improved yield and composition as compared to o-raffinose and glutaldehyde polymerized hemoglobin.

EXAMPLE FOUR

Nitroxide-Labelled Lipsome-Encapsulated Hemoglobin

Liposomes are particles which are formed from the aggregation of amphophilic molecules to form a bilayer structure in a hollow spherical shape with the polar sides facing an internal water compartment and external bulk water. Several acceptable methods for forming liposomes are known in the art. Typically, molecules form liposomes in aqueous solution like dipalmitoyl phosphatidylcholine. Liposomes may be formulated with cholesterol for added stability and may include other materials such as neutral lipids, and surface modifiers such as positively or negatively charged compounds. The preferred liposomes are small unilamellar-bilayered spherical shells.

A method for encapsulating hemoglobin in a liposome is also known (See Farmer et. al., U.S. Pat. No. 4,911,921). For the purpose of this invention, a number of approaches may be used to introduce the nitroxide-based oxygen detoxification function to a solution of liposome-encapsulated hemoglobin. For example, it is possible to use nitroxide-labelled native hemoglobin, or a nitroxide-labelled stabilized hemoglobin as disclosed above, as the starting material and then performing the process of liposome encapsulation of the nitroxide-labelled hemoglobin by known techniques. In the present embodiment, purified hemoglobin may also be coencapsulated with a membrane impermeable nitroxide such as TEMPO-choline chloride disclosed for a spin membrane immunoassay in Hsia et. al. U.S. Pat. No. 4,235,792.

Figure 10A:
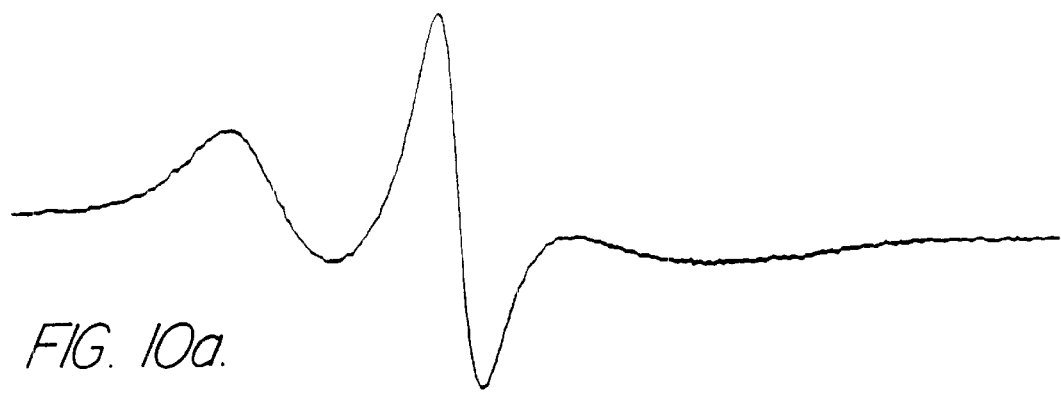
FIGS. 10A and 10B, respectively, are electron spin resonance spectra of liposome encapsulated human hemoglobin containing (A) 3-DOXYL-cholestane (B) 16-DOXYL-stearic acid.
Figure 10B:
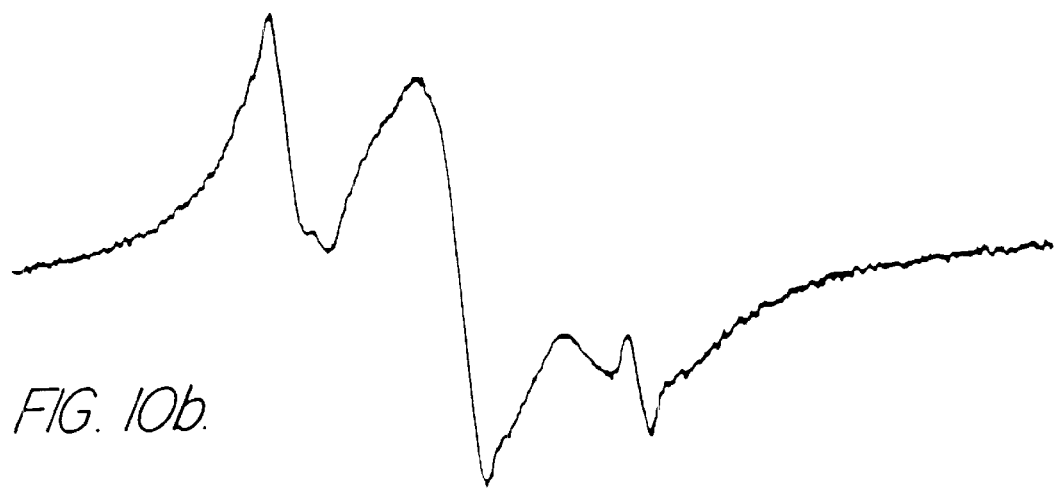
Figure 10C:
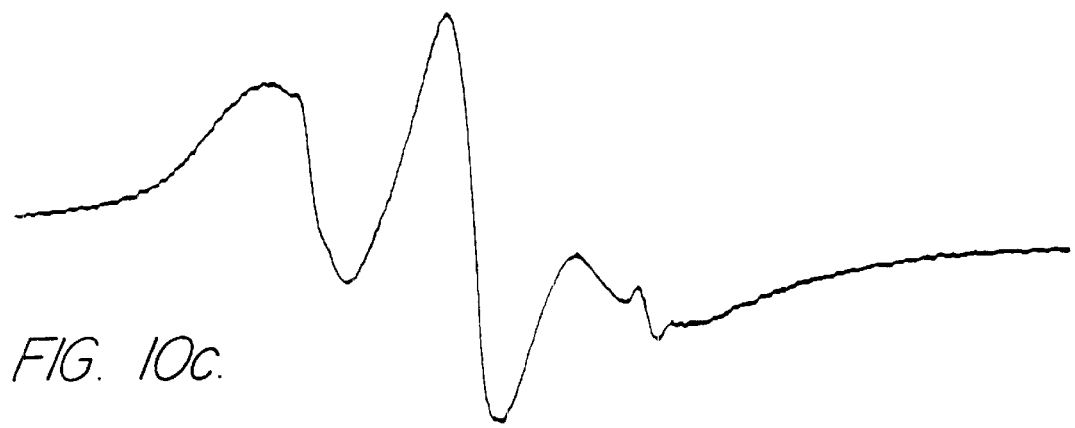
FIG. 10C is the electron spin resonance spectra of both 3-DOXYL-cholestane and 16-DOXYL-stearate.

Also, any purified hemoglobin may be encapsulated with a liposome comprised of nitroxide-labelled fatty acids (e.g., 7-DOXYL-stearate, 12-DOXYL-stearic acid, and 16-DOXYL-stearate), cholestane, an analogue of cholesterol (e.g., 3-DOXYL-cholestane), or phospholipid (e.g., 12-DOXYL-stearate-labelled phosphatidylcholine). The preparation of hemoglobin encapsulated in a liposome comprised of 3-DOXYL-cholestane labelled may be prepared by a method analogous to that described in Tabushi et. al., (J. Am. Chem. Soc. 106: 219 (1984)). A 5 ml chloroform solution containing lipid compositions, including DOXYL labelled stearic acid and/or cholestane, as specified below were first dried in a stream of nitrogen to remove the solvent. Next, the residues were dried in vacuo and the resulting film was suspended in 2 ml of hemoglobin (24 g/dl) in a Lactated Ringers solution. The lipid concentration in the dispersion is 100 mM. The liposome encapsulated hemoglobin is then rotated and incubated preferably at 37° C. until all lipids are dispersed to form multilamellar vesicles. The resulting solution containing multilamellar liposome encapsulated hemoglobin and free unencapsulated hemoglobin is then forced through a microfluidizer to form 0.2 micron liposomes according to the procedure of Cook et.al. (See U.S. Pat. No. 4,533,254). The molar ratio of dipalmitoyl phosphatidylcoline: cholesterol: dipalmitidyl phosphatidic acid: 3-DOXYL-cholestane in the liposome is 0.5:0.4:0.02:0.07. The resonance spectrum of the resulting 3-DOXYL-cholestane labelled liposome-encapsulated hemoglobin is shown in FIG. 10A. In this configuration, the nitroxide is intercalated into the liposome membrane and can be found at both the inner and outer surface of the lipid bilayer water interface. Substituting the 3-DOXYL-cholestane with 16-DOXYL-stearic acid in the lipid composition shown in FIG. 10A results in an electron resonance spectrum shown in FIG. 10B. The mobility of the nitroxide as reflected from the resonance spectrum is consistent with the interpretation that the DOXYL-moiety of the stearic acid is located predominately in the hydrophobic interior of the lipid bilayer. With the addition of both the 3-DOXYL-cholestane and 16-DOXYL-stearate to the lipid composition at the same molar ratio, the resonance spectrum of the double nitroxide-labelled liposome encapsulated hemoglobin is shown in FIG. 10C. The resonance spectrum of FIG. 10C is a composite of FIGS. 10A and 10B because the nitroxides in this embodiment are located at both the membrane-water interface and its hydrophobic lipid bilayer interior. By placing the nitroxide in both locations, this embodiment provides the oxygen detoxification function at both the lipid bilayer hydrophobic interior and the membrane-water interface thus providing the added benefit of an additional reserve of oxygen-detoxification capacity for the encapsulated hemoglobin.

EXAMPLE FIVE

Nitroxide-Labelled Conlugated Hemoglobin

A physiologically compatible solution of conjugated hemoglobin is produced by forming a conjugate of hemoglobin and a biocompatible macromolecule used as a plasma expander. Plasma expanders, such as dextran (Dx), polyoxyethylene (POE), hydroxylethyl starch (HES), are used to increase the circulation half life of hemoglobin in the body. In this state, the hemoglobin molecules together with the biocompatible macromolecule are collectively referred to as a hemoglobin conjugate. There are a number of convenient methods to incorporate a nitroxide into a hemoglobin conjugate. For example, one may simply substitute the hemoglobin to be conjugated with a nitroxide-labelled hemoglobin such as TEMPO labelled DBBF-Hb. This can be accomplished by substituting hemoglobin or pyridoxylated hemoglobin with 3-maleimido-PROXYL-DBBF-Hb or 4-(2-bromoacetamido)-TEMPO-DBBF-Hb in the preparation of conjugated hemoglobin.

Figure 11:
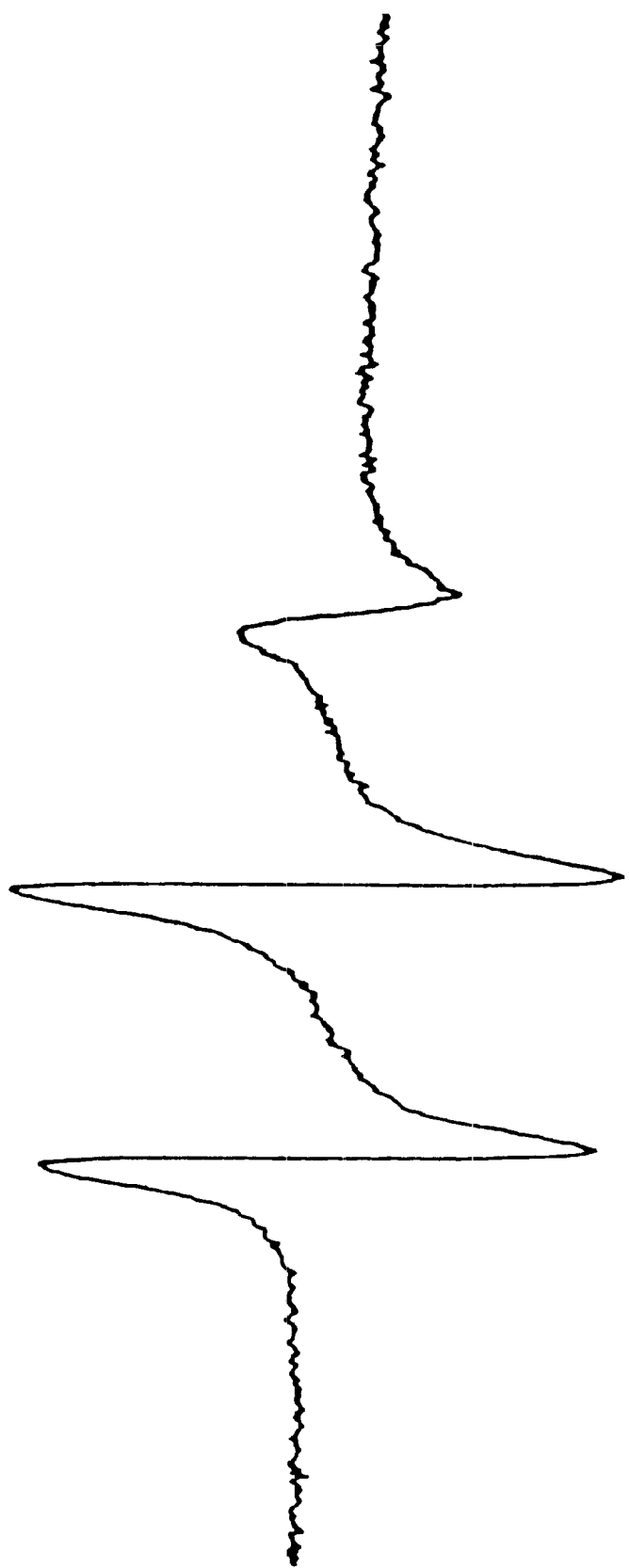
FIG. 11 is the electron spin resonance spectrum of nitroxide-labelled hemoglobin labelled with 4-amino-TEMPO and conjugated with dextran.

4-Amino-TEMPO labelled dextran conjugated hemoglobin is prepared in accord with the procedure described by Tam et. al. (Proc. Natl. Acad. Sci., 73:2128 (1976)). Initially, an 8% hemoglobin solution in 0.15 M NaCl and 5 mM phosphate buffer, pH 7.4 is conjugated to periodate-oxidized dextran to form a Schiff-base intermediate. Twenty molar equivalents of 4-amino-TEMPO is added to hemoglobin to form the Schiff-base between the nitroxide and the remaining reactive aldehyde groups on the dextran. After a 30 minute of incubation at 4° C., a 50 molar equivalent of dimethylamine borane in water is added. The solution is incubated for a further 2 hours at 4° C. Afterwards, the solution is dialyzed, reconstituted with Lactate Ringers buffer and sterile filtered with Filtron membrane filtration units (Filtron Technology Co.). The electron spin resonance spectrum of the 4-amino-TEMPO labelled dextran-conjugated hemoglobin is a sharp asymmetric triplet reflecting a high degree of motional freedom (See FIG. 11). The increased mobility of the TEMPO covalently attached to the Dextran is consistent with the nitroxide linked to a flexible polysaccharide dextran chain as compared to that of a tightly folded hemoglobin molecule (See FIGS. 3A and 3B). Thus, resonance spectrum in FIG. 11 demonstrates that a novel nitroxide-labelled dextran conjugated hemoglobin has been prepared.

EXAMPLE SIX

Nitroxide-Labelled Albumin

A preferred embodiment of this invention is the use of nitroxide-labelled biocompatible macromolecules in connection with low molecular weight, membrane permeable nitroxides to provide sustained antioxidant activity in vivo. Preferably, the nitroxide is labelled to a biocompatible protein, as used herein, the term "protein" includes fragments and derivatives thereof. The nitroxide-labelled protein is preferably provided by labelling at a large portion of the amino groups of the protein. An example of such a desirable biocompatible macromolecule is human serum albumin (HSA). Additionally, labelling at the disulfide bonds increases the molar ratio of nitroxide to protein. By so labelling the protein, an acidic microenvironment is created which enhances the interaction between the free nitroxide and the macromolecule-bound nitroxide, facilitating election spin transfer due to the differential stabilities of the species. Such covalently labelled nitroxides are attached as dinitroxide, trinitroxides or polynitroxide carboxyl copolymers with molecular weight of 5000 to 7000. Thus the molar ratio of nitroxide to albumin may be increased to approximately 400 and may be varied by the labelling strategies disclosed herein to reach an integral value or range of values up to 400. In the case of albumin, it is also possible to covalently bind a nitroxide to the primary bilirubin binding site of the albumin, using for example an activated derivative of a nitroxide with specific binding affinity for that site, e.g., TOPS. By selecting the binding site on the macromolecule, the reactivity of the nitroxide is modified and this modification can be used to alter the reactivity of the compound.

Serum albumin is a plasma protein with multiple ligand-binding sites and is the transport protein for many ligands in the blood. Nitroxides can bind specifically to human serum albumin at a number of specific ligand binding sites, or non-specifically. This binding can be non-covalent, or covalent through the use of activated nitroxides. Nitroxide-albumin may be used either alone or in combination with a low molecular weight nitroxide compound, e.g., TEMPOL, TOPS, and mono- and diesters of TOPS for oral, parenteral, and topical therapeutic applications. Nitroxide-labelled albumin is also available as an "improved" version of albumin (i.e., improved by having antioxidant activity) with utility in any application where albumin is now conventionally used, including as red cell preservative, a parenteral colloid solution, in biomaterials, in biocompatible surface coatings, etc. and additionally in antioxidant applications such as cellular preservation compound for use e.g., in preservation of organs for transplantation and red blood cells for transfusion.

The albumin may be obtained from plasma or may be produced by recombinant genetic means. HSA may be used in a variety of forms, including monomers (normal plasma form), homodimers, oligomers, and aggregates (microspheres and albumin microbubbles). Additionally, albumin may be treated with polyethyleneglycol to reduce its immunogenicity. Specific labelling of the albumin with a nitroxide may be achieved at several binding sites, including bilirubin, FFA, indole, or $Cu^{++}$ binding site by using activated derivatives of nitroxide compounds which have binding specificity for the relevant site on the protein. A preferred example is 2,2,6,6-tetramethyl-1-oxyl-4-piperidylidene succinate (TOPS) nitroxide covalently bound to the primary bilirubin-binding site of HSA. Non-specific labelling of albumin may be achieved at up to approximately 50 accessible amino groups. Temperature and chemical treatment of the albumin permits increasing the molar ratio of nitroxide to albumin. Using native albumin, molar ratios above 7 and up to 60 can be achieved. Using nitroxide-labelled albumin up to 60 moles, a molar ratio of nitroxide to albumin up to 95 may be achieved by labelling the 35 potential sulfhydrol groups of the albumin with additional nitroxides. Such covalently labelled nitroxides are attached as dinitroxide, trinitroxides or polynitroxide carboxyl copolymers with molecular weight 5000 to 7000. Thus the molar ratio of nitroxide to albumin may be increased to approximately 400 and may be varied by the labelling strategies disclosed herein to reach an integral value or range of values up to 400.

Figure 18A:
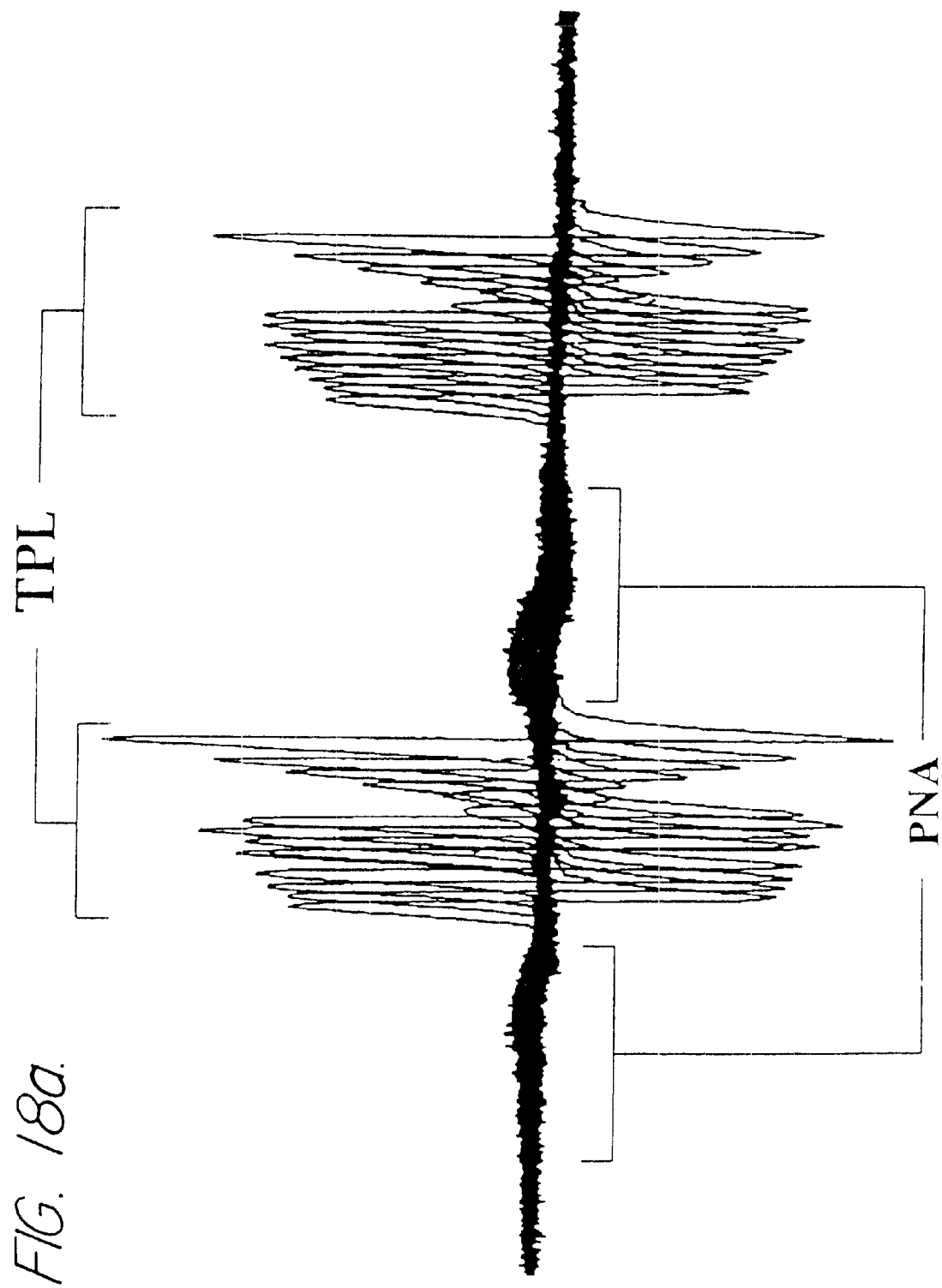
FIG. 18A is a continuous recording of fifteen (15) EPR spectra of the mouse tail recorded by manually increasing the field strength by approximately 1 G in between scans. The scan numbers were marked on the high field peak (M-½) of the $^{15}N$ TPL. The mouse was previously injected with 0.5 ml of 40 mM $^{15}N$ TPL, which was reduced to TPH with a half-life of 2 minutes (results not shown). The second injection of a mixture of PNA and $^{15}N$ TPL into the mouse tail vein showed a similar rate of disappearance of $^{15}N$-TPL (see peaks 1–5 recorded at 30 sec. intervals with a half-life of ~2 minutes) followed by a equally rapid recovery of the peak intensity (see peaks 5–7). The peak intensity of TPL decays with a half-life of 13 minutes (see peaks 7–15, recorded at 1 minute intervals) The center (Mo) broad resonance peak (A) of polynitroxide albumin (PNA) shown in between the two clusters (M+½ and M-½) of $^{15}N$-TPL peaks (TPL) also appeared to decay at a half-life of 13 minutes. Thus, the use of $^{15}N$-TPL clearly demonstrates the spin-transfer from TPH to the $^{14}N$ nitroxides on PNA in vivo.
Figure 19:
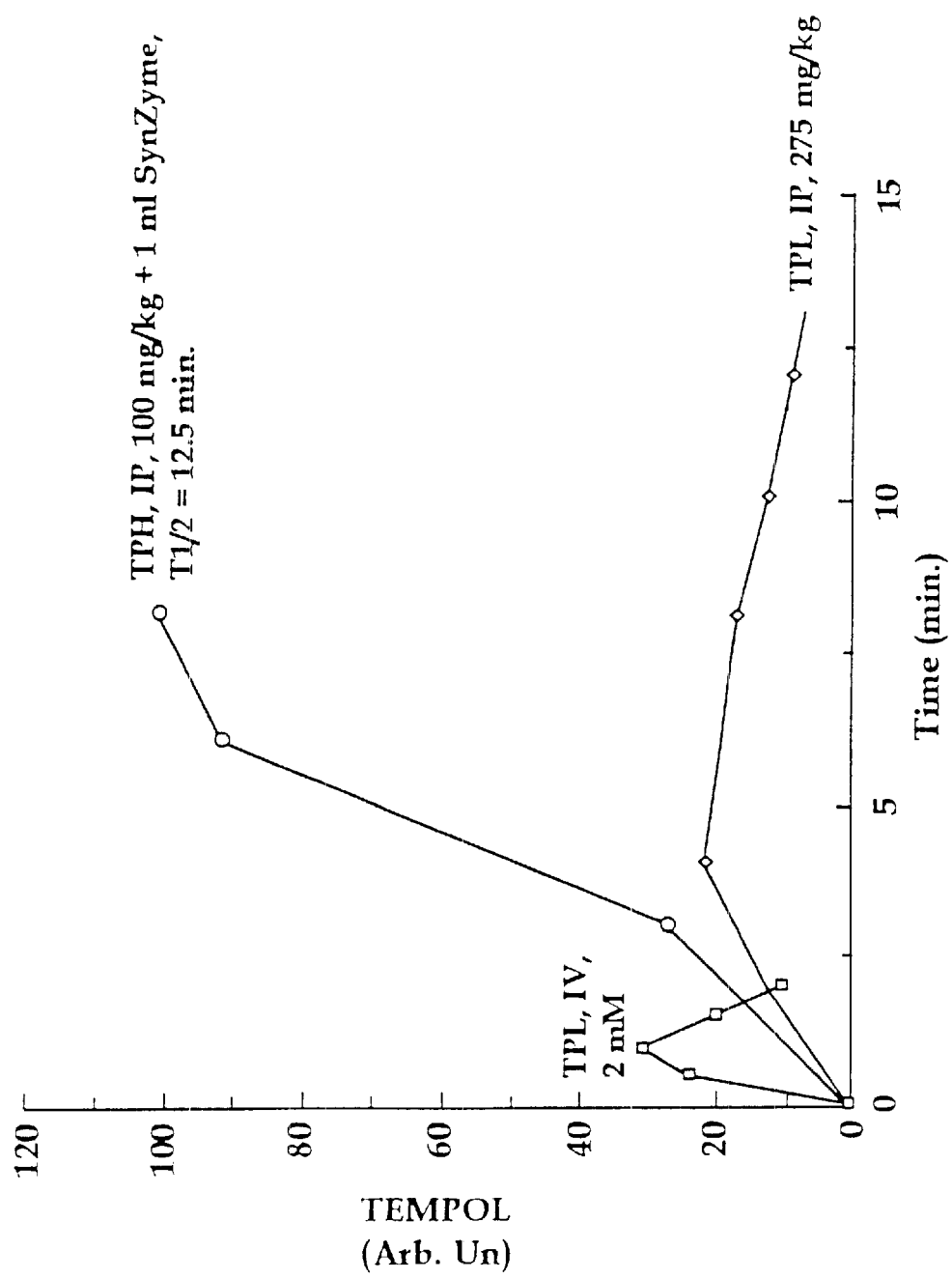
FIG. 19 shows pharmacokinetics of TPL and TPH in the presence or absence of PNA in C57 mice. Plasma levels of TPL in arbitrary units as determined by monitoring the EPR high field peak intensity were plotted as a function of time field (min.), (□) TPL (2 mM alone) by intravenous administration, (◇) TPL 275 mg/kg by intraperitoneal administration and (○) PNA by intravenous administration followed by TPH 100 mg/kg by intraperitoneal administration.

To demonstrate the regeneration of the active nitroxide in vivo, 4-hydroxyl-2,2,6,6-tetramethyl-piperdine-N-oxyl (N-TPL) in phosphate buffered saline was injected into the tail vein of an anesthetized mouse (body weight 40 g) as a control. The tip of the tail was inserted into the sample tube of an electron spin resonance (ESR) spectrometer. The mouse tail displayed no esr signal before the injection. After the injection of 0.5 ml of 6 mM TEMPOL, an esr signal was detected and observed to decay rapidly, as seen in three successive scans of the spectrum at 30 second intervals (see FIG. 18A). This result indicates that the TEMPOL was reduced to its esr-silent, and catalytically inactive, N-hydroxylamine (R-NOH) derivative (TEMPOL-H or TPH). To measure the plasma half-life of TEMPOL in the mouse tail, the intensity of the high-field peak was monitored continuously for 8 minutes (FIG. 19). After 8 minutes, a repeat injection of TEMPOL was made. The maximum peak intensity, which corresponds to TEMPOL (TPL) concentration, was attained in the mouse tail in approximately 10 seconds, followed by a rapid decay to base line, resulting in a half-life in vivo of TPL of approximately 50 seconds (FIG. 19). The half-life of TPL was confirmed by two recording methods: scanning the entire spectrum at intervals and continuous recording of the high-field peak intensity. The results from both methods were in agreement.

To prepare the polynitroxide albumin (PNA), human serum albumin (HSA, 5% solution, Baxter Healthcare Corp.) was allowed to react with 60 molar equivalents of Br-TEMPO (Sigma) at 60° C. for 10 hours with mixing. The resulting reaction mixture, containing 15 ml of HSA and 165 mg of Br-TEMPO in a Vacutainer tube, was filter-sterilized with a 0.22 micron filter and transferred into a 150 ml stirred cell (Stirred Cell Devices) equipped with a 10 kda-cutoff ultrafiltration membrane (Filtron Technology Corp.). The filtered reaction mixture was washed with Ringer's solution (McGaw Inc.) until the filtrate contained less than 1 $\mu$M of free Br-TEMPO as detected by esr spectroscopy. The bright orange retentate was concentrated to 25% HSA and again filter-sterilized with a 0.22 micron filter into a 10 ml sterile vial (Abbott Laboratories) and stored at 4° C. until use. The esr spectrum of the macromolecular polynitroxide is shown in FIG. 15C.

To increase the molar ratio of nitroxide in a polynitroxide albumin, the disulfide groups are reduced to sodium thioghycolate in the presence of urea and an excess of BR-TEMPO is added to label the broken disulfide bonds. An average increase in the molar ratio of approximately 10 is achieved by this procedure, which is analogous to the procedure described by Chan et al in "Potential of Albumin Labeled with Nitroxides as a Contrast Agent for Magnetic Resonance Imaging and Spectroscopy," Biconjugate Chemistry, 1990, Vol. 1, pages 32–36.

The concentration of a polynitroxide albumin solution is adjusted to 17.5 mg/ml in a flask. This solution is diluted with urea to 8M and stirred until dissolved. The pH is adjusted to 8.2 by addition of 2% sodium carbonate. The pH-adjusted solution is degassed completely for 15 minutes, then flashed with argon gas. In another flask, a 3M solution of thioglycolate is prepared, degassed, and flashed with argon gas. The thioglycolate solution is added to the polynitroxide albumin to a final concentration of 0.3M.

The resulting solution is degassed and flashed with argon gas to mixture and allowed to stand in the dark under argon gas for 20 hours at room temperature, followed by dialyzation against 3 L of degassed phosphate-buffer saline pH 8.4 (adjusted by 2% sodium carbonate) for 5 hours at room temperature under argon gas. An excess of Br-tempo is added and the mixture stirred for an additional 24 hours at room temperature under argon gas.

The final solution is dialyzed against PBS pH 7.4 for 5 hours to remove unreacted nitroxide. EPR spectroscopy may be used to determine spin density and protein concentration may be determined by Biuret method.

Typical results are set forth below for the average of three lots.:
1. Protein concentration:
    Amino group labelled polynitroxide albumin
        53.0 mg/ml=0.78 mM
    Amino plus disulfide
        13.9 mg/ml=0.20 mM
2. Spin density:
    Amino group labelled polynitroxide albumin (PNA)
        33 mM
    Amino plus disulfide
        10.5 mM
3. Calculation of molar ratio of nitroxides bound to protein.
    Amino group labelled polynitroxide albumin
        33 mM/0.78 mM=42 nitroxides/albumin
    Amino plus disulfide
        10.5 mM/0.20 mM=52 nitroxides/albumin Reduction of the disulfide groups increased by ten the molar ratio of nitroxide to albumin in this example.

The methods used to produce the examples of PNA described herein and used in the examples to demonstrate the therapeutic, diagnostic, and functional utility of the polynitroxylated biocompatible molecules of the invention can be readily applied to produce other compounds such as polynitroxylated HBOC (or PNH), polynitroxylated dextran (PND) and numerous additional PNA formulations as shown in the following chart showing the species of nitroxide, the structure, the protein concentration, the spin density and the binding percentage of the available groups on the albumin protein.

| mane | structure | Protein Conc. mM | Spin Density mM | Binding % |
|---|---|---|---|---|
| 3-Maleimido-PROXYL | 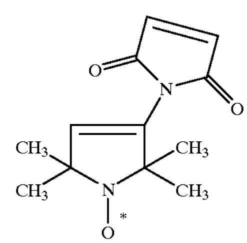 | 0.67 | 6.9 | 17.2 |
| 3-(Maleimidomethyl)-PROXYL | 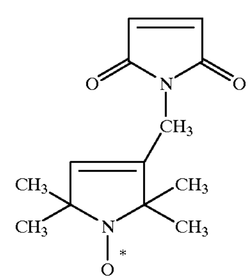 | 0.73 | 7.8 | 17.8 |
| 3-(2-Iodoacetamido)-PROXYL | 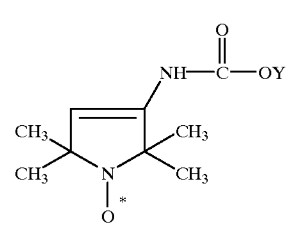 | 0.36 | 5.9 | 27.2 |

-continued

| mane | structure | Protein Conc. mM | Spin Density mM | Binding % |
|---|---|---|---|---|
| (B3T011996) | 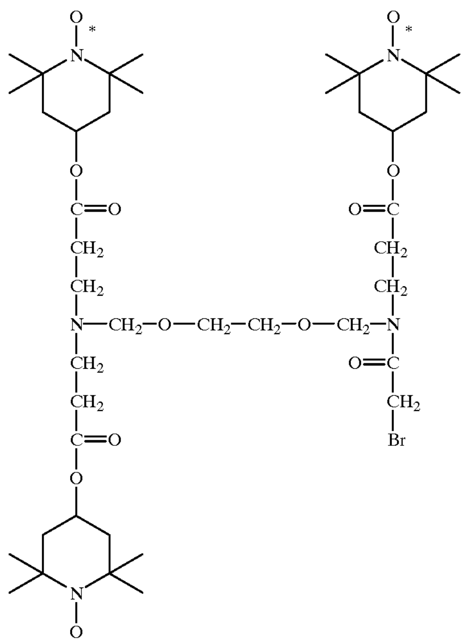 | 0.73 | 21.4 | 49 |
| Ester TEMPO | 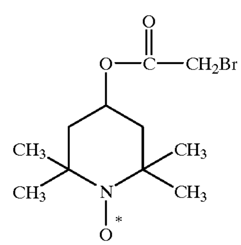 | 0.46 | 5.5 | 18.3 |
| A TEMPO | 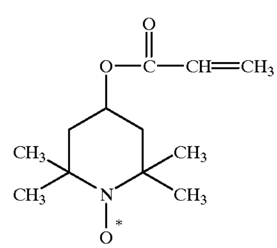 | 0.46 | 0 | 0 |
| 4-(2-Bromoacetamido)-TEMPO | 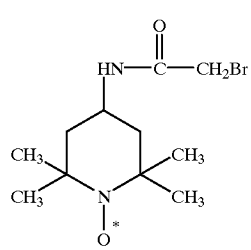 | 0.67 | 12.3 | 29.8 |

-continued

| name | structure | Protein Conc. mM | Spin Density mM | Binding % |
|---|---|---|---|---|
| 4-Isothiocyanato-TEMPO | 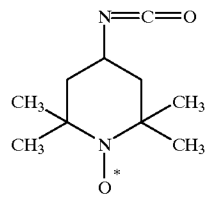 | 0.45 | 5.8 | 21.5 |
| B3T(020996) | 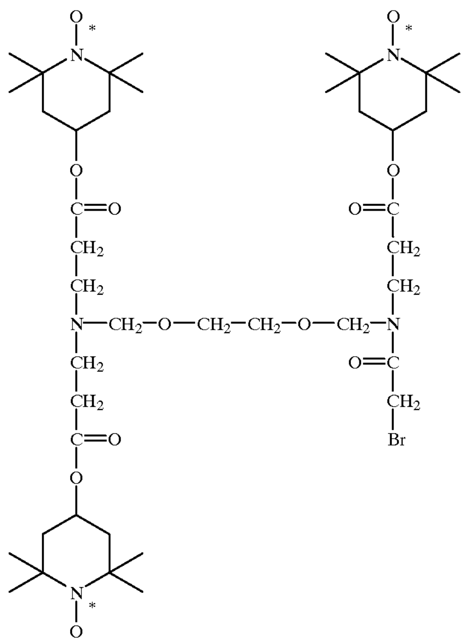 | 0.52 | 8.9 | 28.4 |
| 4-Maleimido-TEMPO | 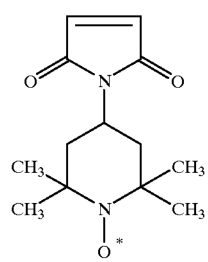 | 0.17 | 1.5 | 14.4 |
| 4-(2-Iodoacetamido)-TEMPO | 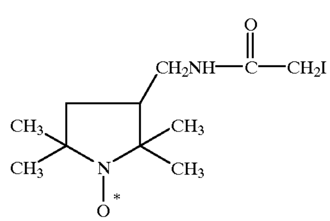 | 0.67 | 10.0 | 24.8 |

To demonstrate that the polynitroxide-labelled albumin formulations described above function to enhance the in vivo activity of the low molecular weight membrane-permeable nitroxide, human serum albumin was covalently labelled with 4-(2-bromoacetamido)-TEMPO (BR-TEMPO) and infused after a dose of TEMPOL had been administered and had been observed to have been converted to its reduced state.

Two hours after the injection of TEMPOL as in the above Example, the mouse tail showed no detectable esr signal. When 0.2 ml of the polynitroxide albumin was injected via the tail vein, the TEMPOL signal reappeared within 4 minutes. The TEMPOL signal intensity persisted for more than two hours, with a half-life of approximately 40 minutes (also see FIG. 18). The TEMPOL signal was distinguished from the polynitroxide albumin signal by their distinctive spectral profiles. The TEMPOL signal was measured as the intensity of its characteristic high-field peak. A nitroxide to albumin molar ratio of 27 displays the same reactivity.

The possibility that the esr signal detected after injection of the polynitroxide albumin was due solely to nitroxide on the macromolecule disassociated from the macromolecule, was ruled out by the following experiment. The experiment was performed as above, but using [$^{15}$N]-TEMPOL and albumin-[$^{14}$N]-TEMPOL. The different nitrogen species provide a method of discriminating the esr signals of the free and the macromolecular nitroxides. The results (FIG. 18A) confirm that the esr signal from the regenerated nitroxide is derived from the $^{15}$N isotope and, therefore, that the antioxidant activity of the low molecular weight membrane permeable [$^{15}$N]-TEMPOL has been regenerated following the addition of the macromolecular polynitroxide.

Figure 18B:
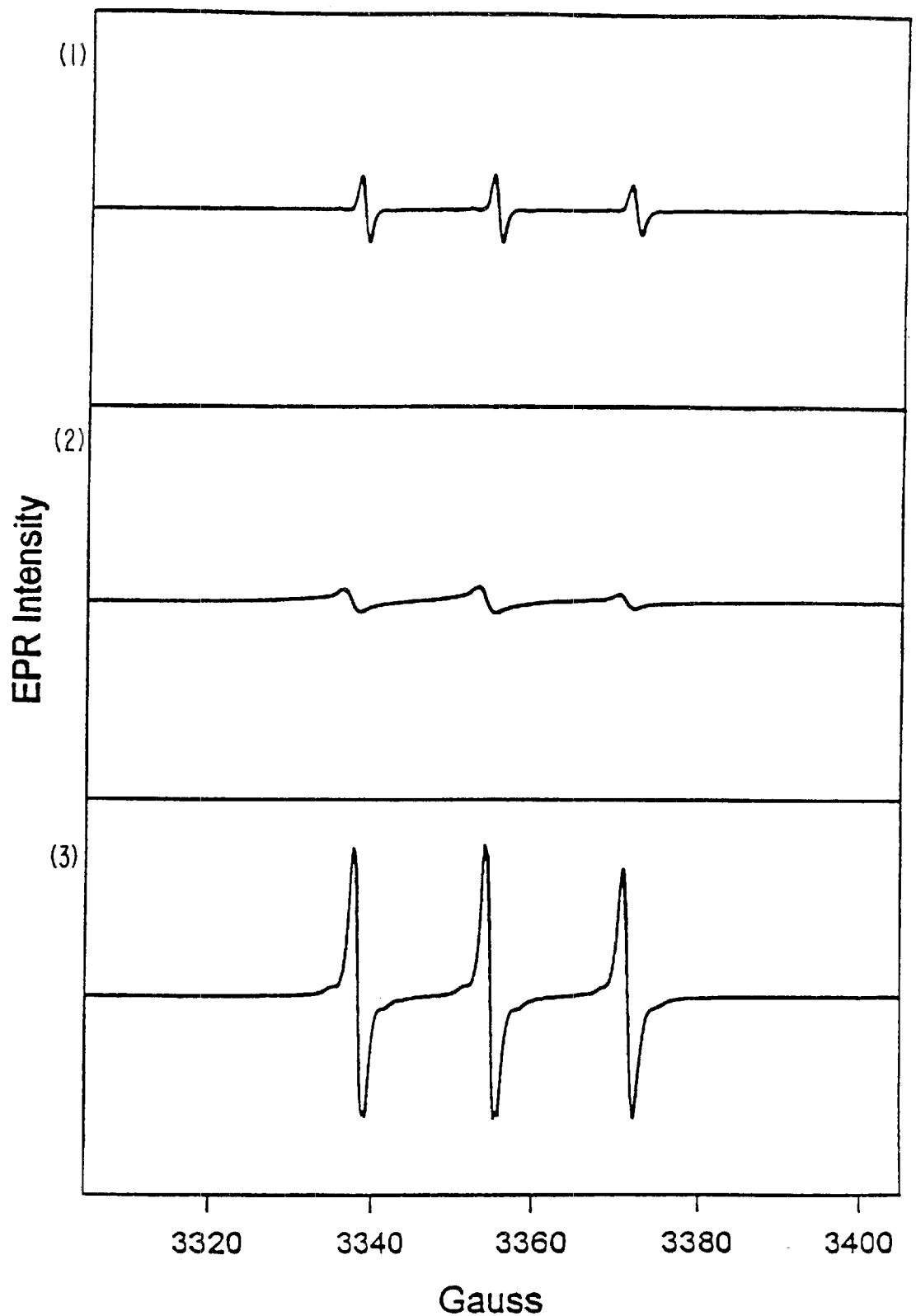
FIGS. 18B, 18C, and 18D are ESR spectra showing activation of TOPS by three different nitroxide-labelled human proteins.
Figure 18C:
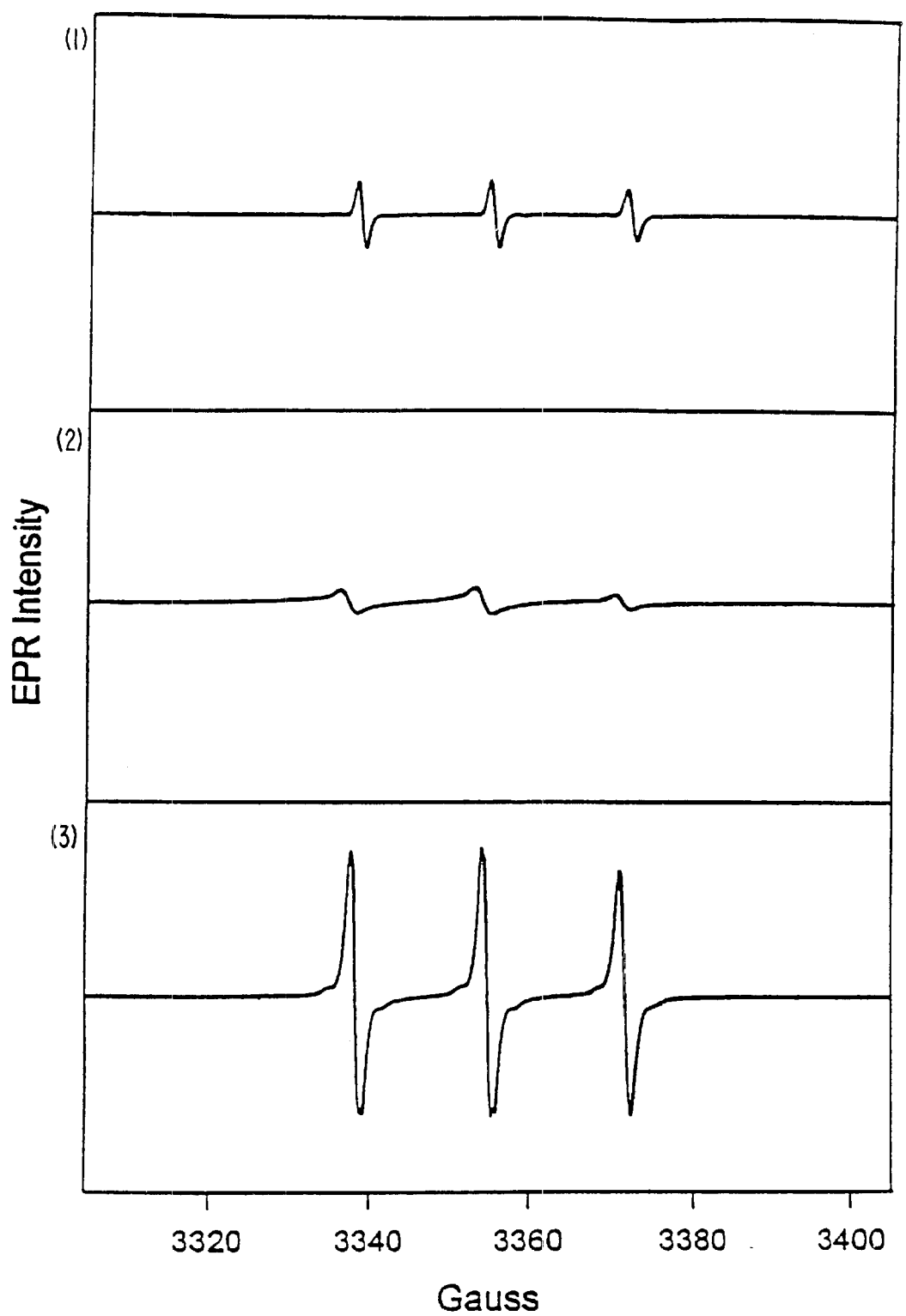
Figure 18D:
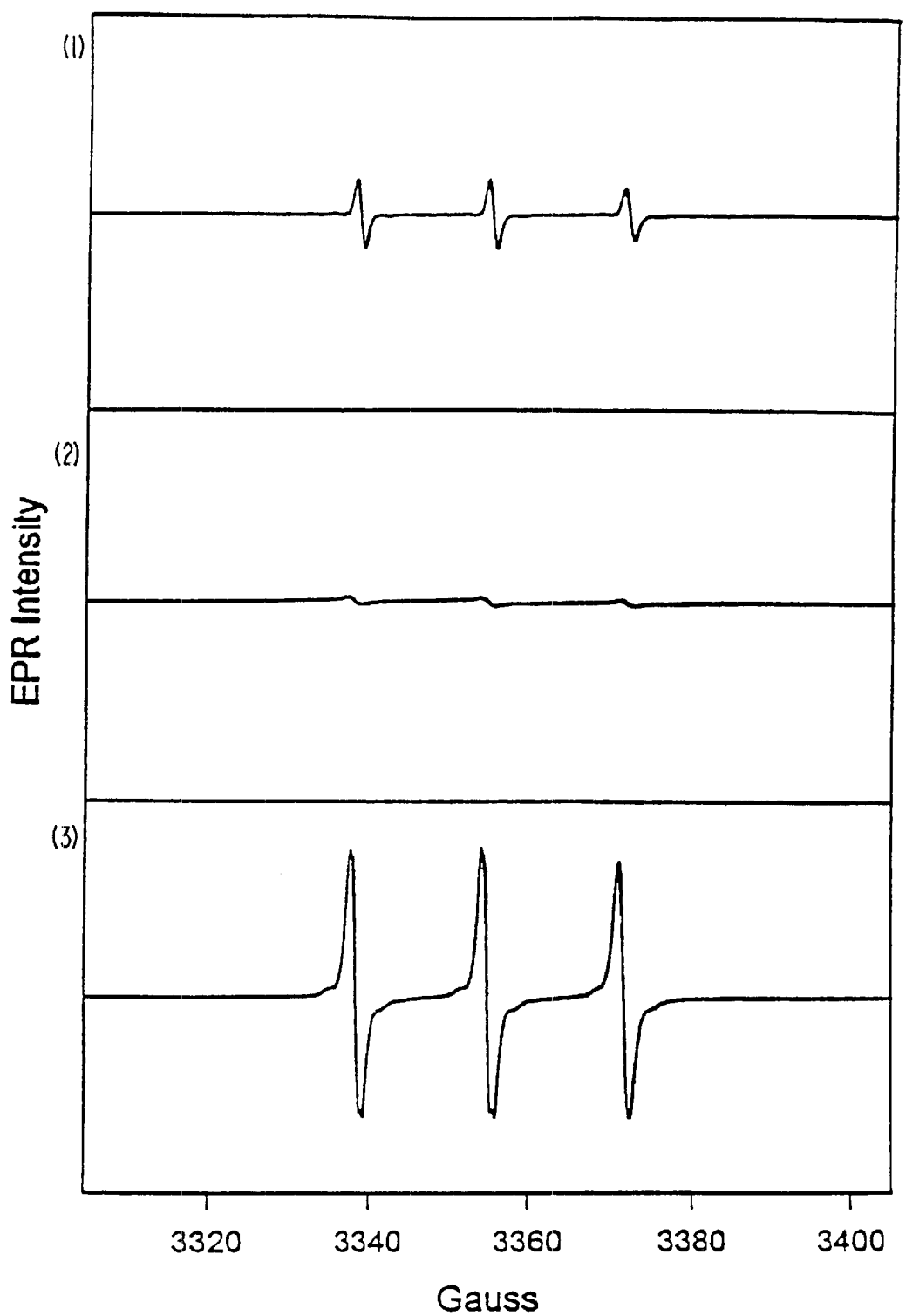

As noted herein, the donor/acceptor relationship between two nitroxide containing species provides the ability for sustained nitroxide protection in vivo. The interaction of PNA and TPL as described with several of the embodiments is only one example of additional combinations provided by the invention. Referring to FIGS. 18B(1), (2) and (3), polynitroxylated albumin (PNA) is shown to activate TOPS. ESR spectra of 50 mM TOPS alone (FIG. 18B(1)) and 43 mM PNA alone (FIG. 18B(2)) reflect a comparatively low peak intensity whereas the combination of TOPS with PNA, in a sodium phosphate buffer (pH 7.8), shows a substantially greater peak intensity (FIG. 18B(3)). Similarly, in FIG. 18C, polynitroxylated HBOC is shown to activate TOPS, and in FIG. 18D, B3T labelled albumin is shown to activate TOPS. Thus, as referred to elsewhere herein, the multiple component embodiments may be formulated with different nitroxides or nitroxide-based compounds with different free-electron stabilities.

EXAMPLE SEVEN

Nitroxide-Labelled Immunoglobulin

As in the above embodiments, certain nitroxides have been shown to have very short plasma half-life when injected intravenously. Due to the desire to have an antioxidant enzyme mimic with a long plasma half-life, a nitroxide compound may be attached to an immunoglobulin to provide long-lasting antioxidant enzyme mimic activity.

Immunoglobulins are a class of plasma proteins produced in the B-cells of the immune system and which are characterized by two specific ligand binding sites (the antigen-binding sites). Nitroxides have been used in the past as probes in research on hapten-binding specificity and affinity of immunoglobulins during the primary and secondary immune response.

As with the above-embodiment describing nitroxide-labelled albumin, the nitroxide-labelling technology demonstrated above in the example of nitroxide-HBOC is readily applied to the production of nitroxide-labelled immunoglobulins. Immunoglobulins after the advantage of specific binding and long circulatory half-life such that the enzyme-mimic activity of the compounds of this invention can be targeted to specific tissues and have prolonged activity.

Nitroxide-labelled immunoglobulins may be used in vivo to provide protection against cellular damage by reactive oxygen species. Nitroxide-labelled immunoglobulin may be used either alone or in combination with a low molecular weight nitroxide compound to provide extended antioxidant activity with an extended plasma half-life.

Nitroxide-labelled immunoglobulin may be prepared by specific labelling of the immunoglobulin itself or by covalently labelling at a hapten-binding site. To avoid clearance of the nitroxide-labelled immunoglobulin as part of the body's natural immune response, one may use immunoglobulin fragments, for example, (Fab)$_2$ produced by cleaving the immunoglobulin according to known techniques with non-specific-labelling, a preferred molar ratio of nitroxide-:immunoglobulin is up to 60:1.

Nitroxide-labelled immunoglobulins are a preferred species for use to target the enzyme-mimic effect of a particular location. For examples by selecting antibodies specific to an antigen implicated in inflammation or other such pathology. The image enhancing and therapeutic benefits of this invention can be targeted at a particular site.

EXAMPLE EIGHT

Imaging of Biological Structures and Free Radical Reactions by EPR

Under most circumstances, free radical reactions occur so rapidly that EPR imaging (ERI) is difficult. However, due to the presence of stable free radicals, nitroxides are detectable by electron paramagnetic resonance spectroscopy. With the development of advanced imaging instrumentation images of intact biological tissues and organs are available based on a measurement of free radical concentration. Biocompatible nitroxides are candidates for image-enhancing agents.

Because nitroxides are reduced in vivo to inactive derivatives within a few minutes of administration, their utility is limited. Pursuant to this invention, active nitroxide levels in the body may be maintained for a prolonged period of time allowing both improved image contrast and longer signal persistence than seen with low molecular weight membrane permeable nitroxides alone.

Electron paramagnetic resonance (EPR) spectroscopy is a technique for observing the behavior of free radicals by detecting changes in the energy state of unpaired electrons in the presence of a magnetic field. The technique is specific for free radicals because only unpaired electrons are detected. Using available apparatus that measure electron paramagnetic resonance, a real-time image of a macroscopic object, including living tissue can be obtained. EPR imaging (ERI) provides the capability to obtain multi-dimensional images (including spectral-spatial images) for diagnosis or research.

Electron paramagnetic resonance imaging (ERI) with nitroxide contrast agents is in principle a valuable method for medical imaging, particularly the imaging of ischemic tissue. However, the development of this technology has been limited by the fact that nitroxides are rapidly reduced in vivo to non-paramagnetic species.

The application for extrinsically introduced nitroxide has demonstrated utility as a relatively low resolution in vivo EPR imaging agent. (L. J. Berliner, "Applications of In Vivo EPR," pp. 292–304 in EPR IMAGING AND IN VIVO EPR, G. R. Eaton, S. S. Eaton, K. Ohno, editors; CRC Press (1991). Importantly, Subramanian and his collaborators constructed a radio frequency fourier transform EPR spectrometer for detecting free radical species and for in vivo imaging. J. Bourg et al., J. Mag. Res. B102, 112–115 (1993).

A polynitroxide albumin (PNA) prepared pursuant to this invention, is administered which distributes in the vascular and other extracellular spaces. Although the range of concentrations of the compositions of this invention may vary. A preferred range is 5–25 g labelled PNA per deciliter and 0.1 to 200 mM TEMPOL. The antioxidant activities and detectability by electron paramagnetic resonance (EPR) spectroscopy and are useful for this purpose alone. Additionally, when administered with modest doses of small molecular weight, membrane permeable nitroxides, the nitroxide is maintained in an active free radical state in the body for a prolonged period of time.

A preferred formulation for ERI imaging is human serum albumin (1.0 to 25.0 g/dl) covalently labelled with a high molar ratio of nitroxide (7 to 95 nitroxide to albumin). As noted elsewhere herein, the polynitroxide albumin (PNA) can accept an unpaired electron from the hydroxylamine form of the nitroxide (e.g., TPH) regenerating the activity of the nitroxide to its free radical state (e.g., TPL). A fundamental advantage of this multi-component system is that while the macromolecule or species remains in the extracellular space, the small, membrane-permeable nitroxide, and its reduced (hydroxylamine) derivative, distribute freely between the intracellular and extracellular spaces. This creates a cycle in which nitroxide free radical can be detected within the cell prior to being reduced, followed by regeneration by the macromolecular (extracellular) species. Thus, a desired concentration of a spectroscopically detectable nitroxide can be maintained in vivo for a prolonged period of time.

Figure 24:
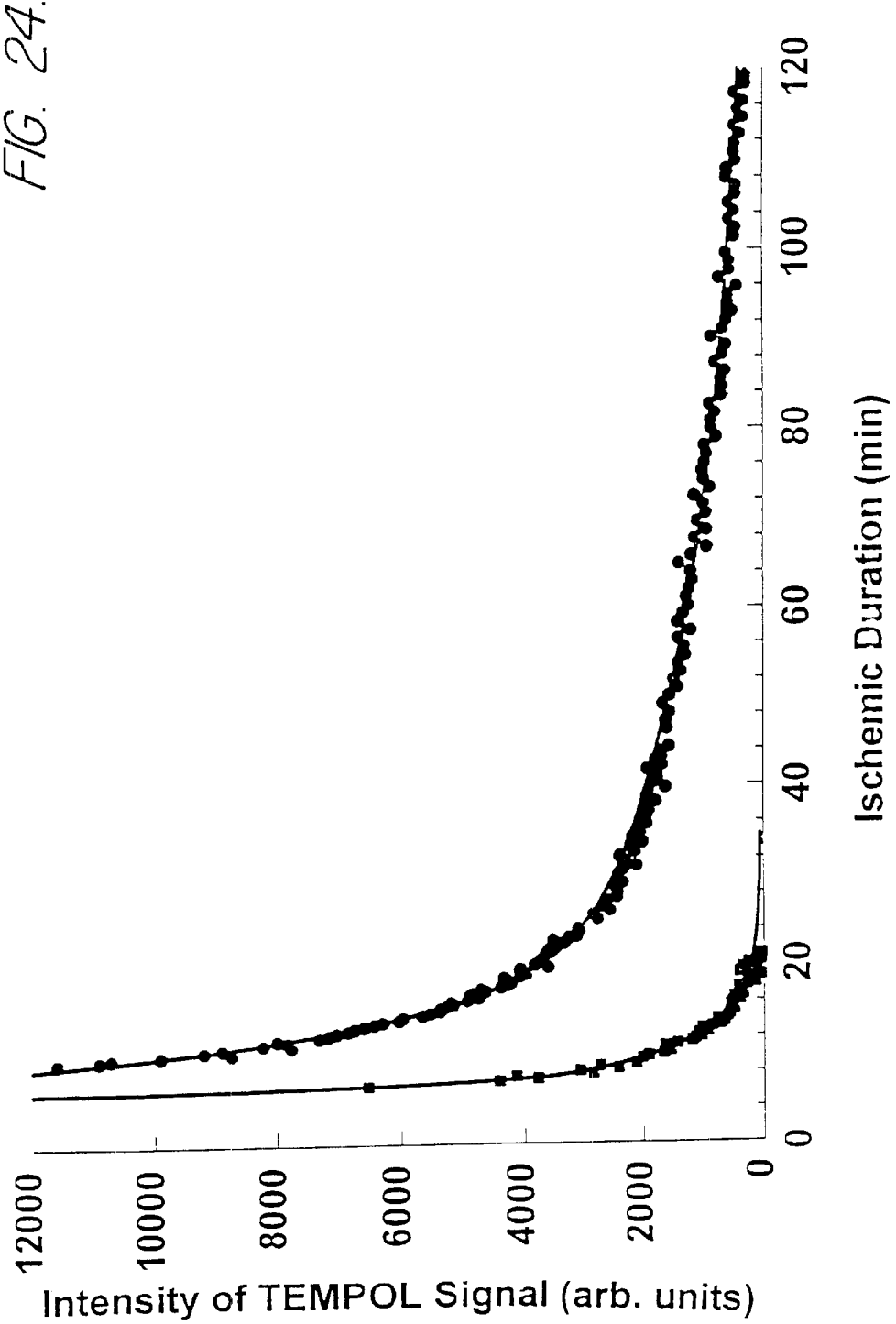
FIG. 24 shows the intensity of $^{15}N$-Tempol EPR signal in two ischemic hearts vs. time of duration of the ischemia. The upper line shows a heart treated with 2 mM TPL+PNA (●) and the lower line shows a heart treated 2 Mm TPL alone (■). The solid lines are double-exponential fittings to the observed intensity data. The half-lives are 0.4 minutes, 2.9 minutes (■), and 3.3 minutes, 30.1 minutes (●) respectively.

Extending the short half-life of nitroxides in vivo helps overcome a major obstacle in the development of a nitroxide-based imaging method and medical therapy. With regard to imaging, the EPR Laboratory at the Johns Hopkins University has been developing a continuous-wave ERI instrument utilizing nitroxide as contrast agent to study the course of cardiac ischemia and reperfusion. However, the limited half-life of nitroxide alone has meant that the reperfusion phase cannot be studied. In these studies, the three-dimensional spectral-spatial EPR imaging of nitroxide in the rat heart suffer from the rapid decay of free radical signal due to nitroxide reduction. Although a cross-sectional transverse 2-D spatial EPR image of the rat heart has been reconstructed from a 3-D spectral-spatial data, this was based on an EPR signal which was decaying continuously during the 12-minute acquisition period. The different rates of nitroxide reduction in the epicardium, myocardium, and endocardium, as a function of the duration of ischemia, further reduces the definition of the cross-sectional image of the heart. Pursuant to this invention, the ERI image may be improved. The extended active half-life of an in vivo nitroxide permits imaging of the reperfusion phase and provides additional information on the progress of ischemic injury to tissues and organs. The compositions of this invention provide a stable nitroxide signal suitable for imaging within 10 minutes after administration, and persists for at least approximately 2.0 hours. (See FIG. 25). For comparison, the signal from a free nitroxide alone effectively disappears within 20 minutes after administration (FIG. 24). With regard to therapeutic utility, the ability to safely maintain active nitroxide levels for prolonged periods of time represents the ability to provide an extended antioxidant effect aiding in the prevention of ischemia/reperfusion injury, pathological processes where toxic oxygen-derived free radicals are the agents of cell damage (see FIG. 26 and FIG. 27).

Using methods essentially as described in Kuppusamy et al. *Proc. Natl. Act. Sci., USA* Vol. 91, pgs. 3388–3392 (1994), the rat heart was imaged using polynitroxide albumin (PNA) at a concentration of 4 g albumin/dl and 2 mM $^{15}$N-TEMPOL.

Referring to FIG. 24, the signal intensity of $^{15}$N-TEMPOL in the presence of polynitroxide albumin, can be seen in the isolated rat heart. The EPR signal was stable with a bi-phasic and gradual decline in intensity. This contrasts with the bi-phasic rapid decline in signal intensity using a low molecular weight membrane permeable nitroxide (TPL) alone (FIG. 24).

Figures 22A, 22B:
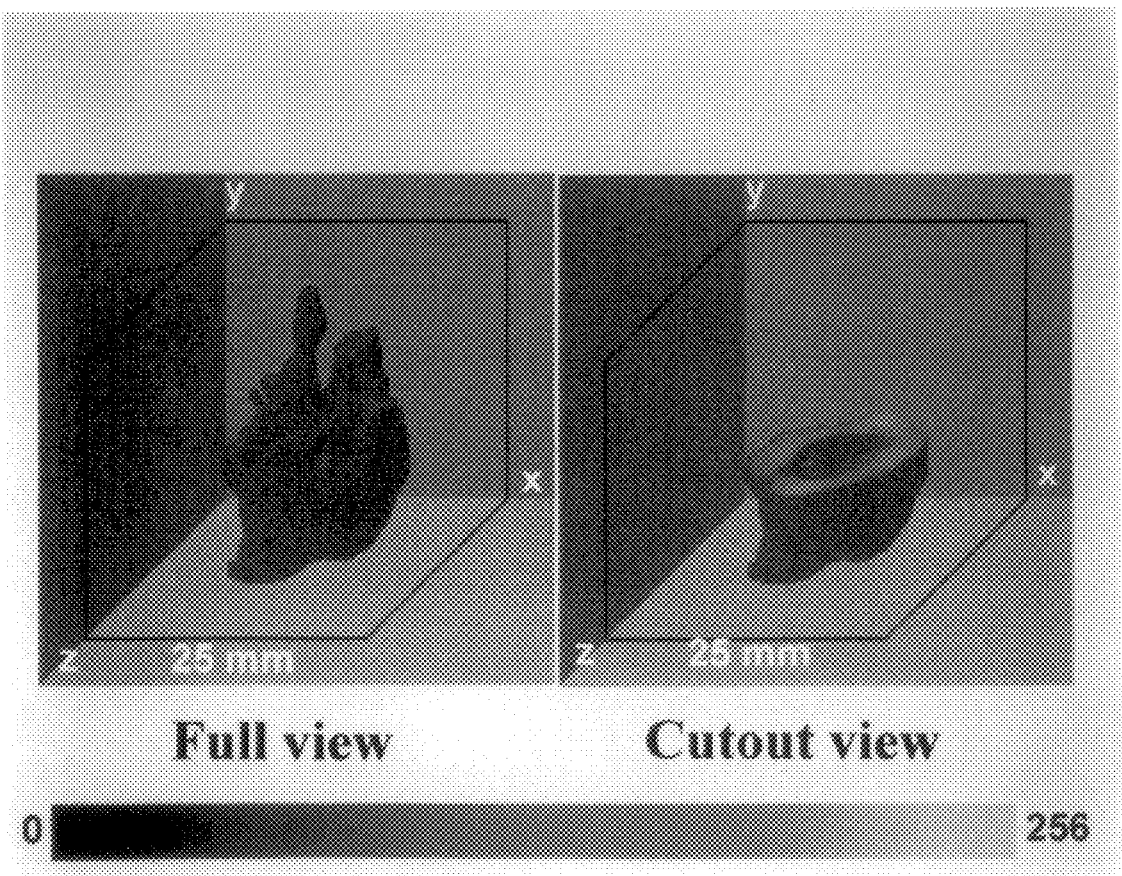
FIG. 22A is a 3-D spatial (25×25×25 mm³) EPR image (full view) of the rat heart loaded with TPL and polynitroxide albumin. The image was reconstructed using 144 projections acquired after 2.5 hours of ischemia.
FIG. 22B is a cutout view of the same image. Data acquisition parameters were as follows: spectral window: 7.0 G; spatial window: 25 mm; maximum gradient: 49.3 G/cm.
Figure 23:
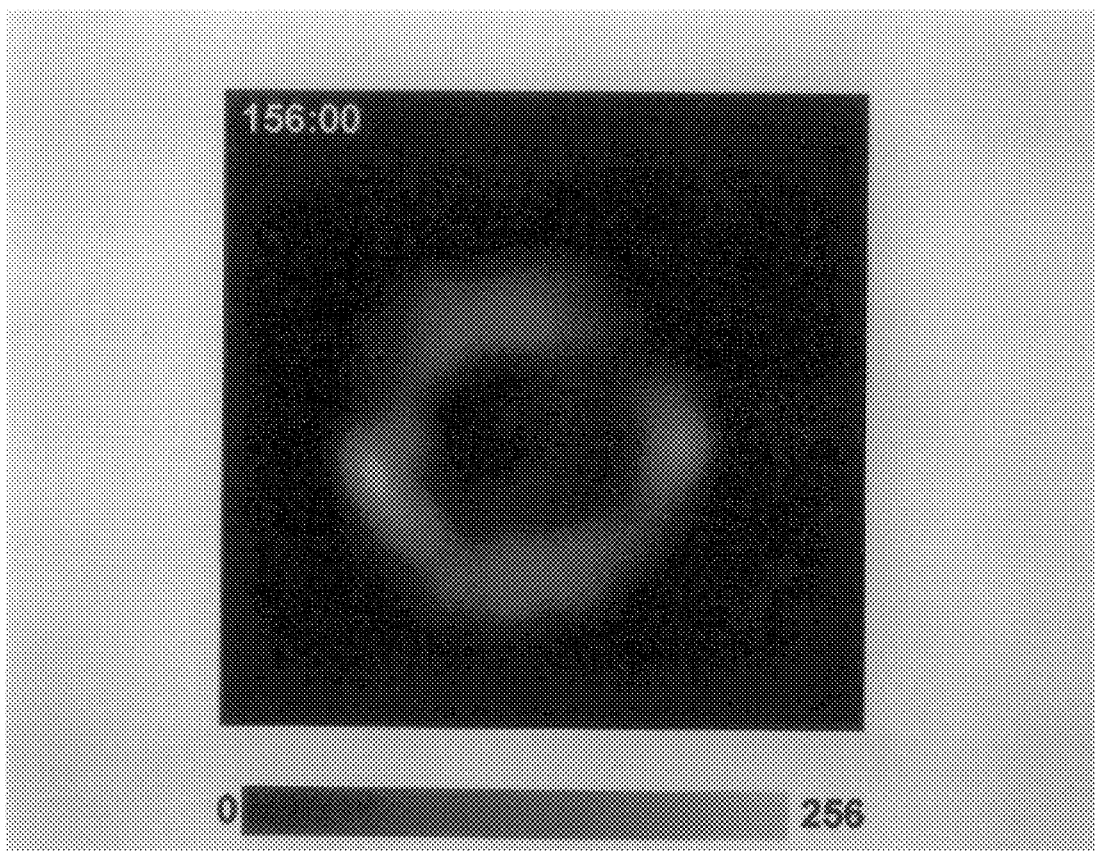
FIG. 23 is an EPR image (25×25 mm²) of the rat heart loaded with TPL and PNA indicating time as a measure of ischemic duration (156 min.), obtained from a 3-D spatial image. Data acquisition parameters were as follows: acquisition time: 10 min.; spectral window: 7.0 G; spatial window: 25 mm; maximum gradient: 49.3 G/cm.
Figure 25:
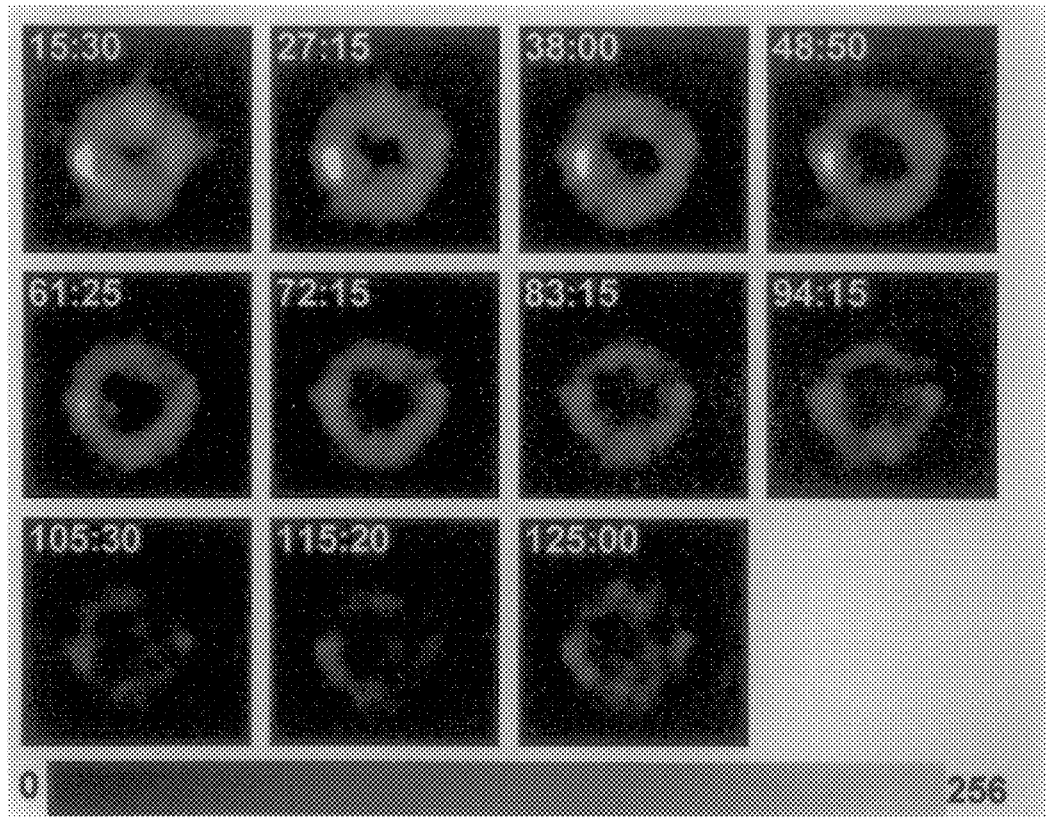
FIG. 25 is a 2-D cross-sectional (25×25 mm²) EPR image of transverse slices of the rat heart loaded with TPL+PNA as a function of ischemic duration with the time indicated digitally (min:sec.) on successive images. The images were obtained from 3-D spatial images. Data acquisition parameters were the same as for FIG. 23.

In an EPR imaging study, the rat heart was perfused with a solution containing nitroxide with or without polynitroxide albumin, followed by cessation of perfusate flow in order to create ischemia. FIG. 24 shows the total signal intensity of [$^{15}$N]-TEMPOL in the isolated rat heart during ischemia in the presence and absence of polynitroxide albumin. It can be seen the signal intensity undergoes a biphasic decay and that the presence of polynitroxide albumin greatly slows the decay. By thus stabilizing the TEMPOL signal, polynitroxide albumin allows high-quality EPR images to be obtained over a prolonged period of time. Referring to FIGS. 22–23, a three-dimensional EPR image of the ischemic heart can still be obtained after 156 minutes of global ischemia. FIG. 22A shows a cut-out view of the image. As illustrated in FIG. 23, the three-dimensional image can also be viewed in cross-section. This shows differential distribution of TEMPOL signal within the ischemic heart; this is quantitated in FIG. 28. FIG. 25 shows a series of images such as in FIG. 23, acquired at a series of successive time points during 125 minutes of global ischemia. This illustrates that the presence of PNA allows much better imaging than is possible with TEMPOL alone, in terms both of resolution and signal persistence.

A particular advantage of this invention is the ability to localize the image enhancement by selecting compositions which are selectively distributed in the structure of interest and/or by selecting a means of administration which facilitates image enhancement of a particular structure or system. For example, image enhancement of the cardiovascular system can be provided by intravenous infusion of a polynitroxide macromolecule having a lengthy plasma half-life and, preferably, an intravenous infusion of low molecular-weight membrane permeable nitroxide. Alternatively, to enhance an image of the gastrointestinal tract, one of these compounds may be administered orally. Similarly, an image enhancement of a discrete region of the skin may be obtained by a topical administration of a polynitroxide macromolecule suspended in a suitable carrier, combined with oral or intravenous administration of an additional nitroxide species. Alternatively, depending on the application, multiple nitroxide-based compositions pursuant to this invention could be dermally administered.

EXAMPLE NINE

Radiation Protection

Living organisms which are exposed to ionizing radiation suffer harmful effects which can be fatal with high doses of radiation. Recent evidence suggest that radiation causes cellular injury through damage to DNA. Of the total damage to DNA, as much as 80% may result from radiation-induced water-derived free radicals and secondary carbon-based radicals. The Department of Defense has had screened over 40,000 aminothiol compounds looking for an in vivo radiation protector. Although one agent (WR-2721) showed selective radioprotective effects, WR-2721 failed to exhibit radiation protection in human clinical trials. A nitroxide compound (e.g., TPL) was a non-thiol radiation protective agent, but as noted herein, (TPL) has a very short in vivo half-life. The other compounds were macromolecules of natural origin (Superoxide dismutase, IL-1, and GM-CSF). However, due to their molecular size, each of these has limited capability to provide intracellular free radical scavenging.

The National Cancer Institute attempted to use the nitroxide compound Tempol as a radioprotective agent to allow greater dosage levels of radiation treatment of cancer patients. The researchers quickly found the low molecular weight nitroxide was quickly reduced to an inactive form and safe dosages could not be administered.

Based on the invention disclosed herein, nitroxides bound to macromolecular compounds as enzyme mimics can be used together with low molecular-weight nitroxides to detoxify oxygen radicals in the vascular space by interacting with membrane-permeable nitroxide compounds to detoxify free radicals inside cells. Extending the duration of the radioprotective effects pursuant to this invention allows the use of nitroxide compounds to protect against the harmful effects of controlled radiation in medical applications such as cancer therapy, and in accidental exposure to harmful radioactive sources.

Figure 16:
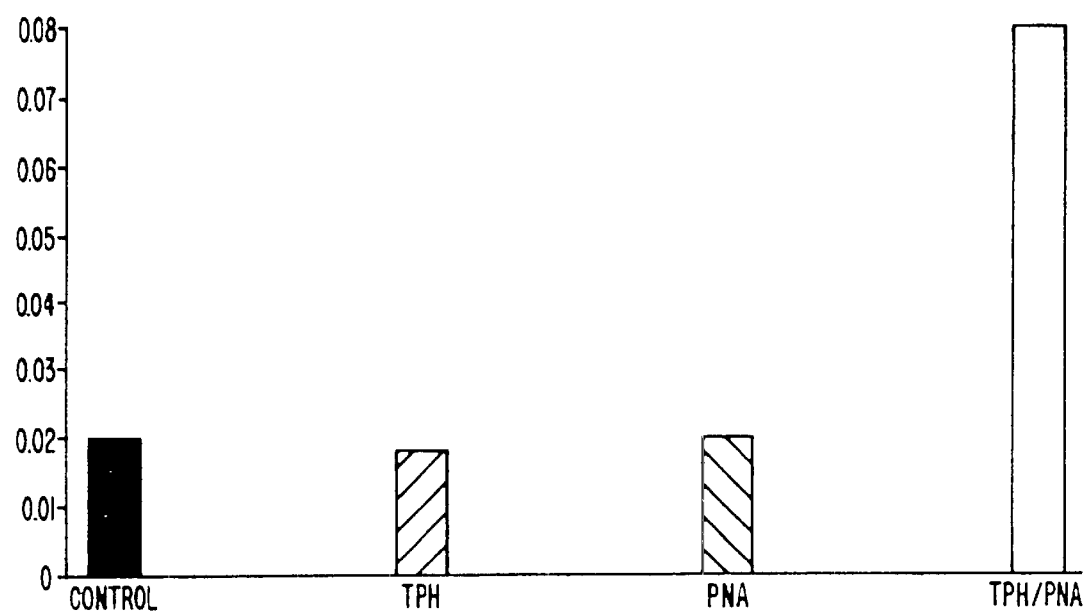
FIG. 16 is a bar graph showing the surviving fraction of Chinese Hamster V79 cells at 12 Gray radiation. The V79 cells were pretreated 10 minutes prior to x-ray irradiation. No radioprotection is observed with TPH or PNA alone (the bar showing 2% survival is same as the control without treatment). Increasing radioprotection is shown by the bar corresponding to the sample containing a combination of TPH and PNA (8% survival).

Based on a radiation dosage scale developed by the National Cancer Institute, chinese hamster cell cultures are exposed to ionizing radiation in the presence of radioprotective chemical agents. FIG. 16 shows the survival rate of Chinese hamster V79 Cells at 12 Gray of radiation. The control, macromolecular bound nitroxide (PNA), and reduced nitroxide (TPH) show similar survival rates. However, TPH premixed with PNA results in the conversion to a radioprotective TPL (see FIG. 17) which enhances the survival of the V79 cells (see FIG. 16).

Low molecular weight, membrane-permeable nitroxides e.g., TPL have been demonstrated to provide radiation protection in vivo in C3H mice. In these studies, the maximal tolerated dose of TPL administered intraperitoneally was found to be 275 mg/kg, which resulted in maximal TPL levels (~150 μg/ml) in whole blood 5–10 minutes after injection. Mice were exposed to whole body radiation in the absence or presence of TPL (275 mg/kg) 5–10 minutes after administration. The dose of radiation at which 50% of TPL treated mice die within 30 days was 9.97 Gray, versus 7.84 Gray for control mice.

Because the radioprotectant effect of TPL is derived from the reactivity of the unpaired electron, when TPL is reduced to hydroxylamine by losing its unpaired electron, it become inactive. The effective radioprotective agent, pursuant to this invention, maintains in vivo a therapeutic concentration of TPL in its active (free radical) state while overcoming the fact that when TPL is administered alone, the dosage required to maintain therapeutic levels is high and is toxic.

FIG. 19 shows that the maximum plasma level of TPL after intraperitoneal injection of 275 mg/kg of TPL (◇) 2 mM TPL alone by intravenous administration (□), and TPH 100 mg/kg+PNA 1 ml (○). The results show that the maximum plasma level of TPL is approximately one-fifth of that observed after the intraperitoneal injection of approximately 100 mg/kg of TEMPOL in the presence of PNA (0.5 ml/mouse at albumin concentration of 20 g/dl and 42 moles TPL per mole of albumin). Therefore, the plasma level of TPL is enhanced by greater than tenfold in the presence of PNA. This enhanced plasma level of TPL influences the intracellular levels of TPL which are responsible for radiation protection at the cellular and nuclear levels.

Figure 20:
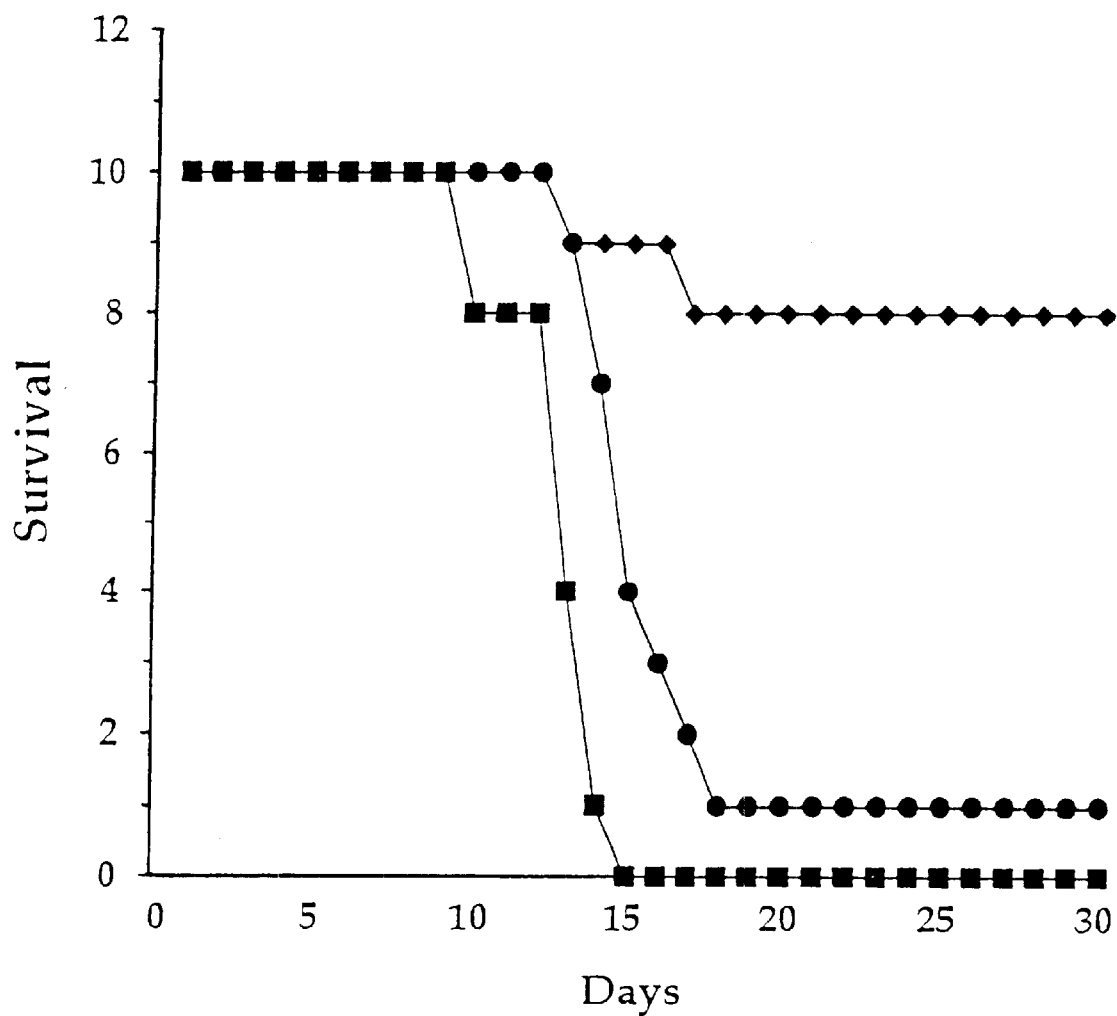
FIG. 20 shows the 30-day survival study of C57 mice (10 mice per group (N=10) exposed to 10 Gray irradiations after treatment with PNA 0.5 ml/mouse by intravenous administration followed by PBS buffer 10 minutes later (■), 0.5 ml PBS followed by 200 mg/kg of TPL 10 minutes later by intraperitoneal (ip) administration (●), polynitroxide albumin 0.5 ml/mouse by intravenous administration followed by 200 mg/kg TPL 10 minutes later (◆).

This enhance protection is demonstrated in full body irradiation based on a 30-day survival model in mice. FIG. 20 shows enhancement of radiation protection by the addition of PNA at a constant TPL concentration (200 mg/kg).

The results show that TPL in the presence of PNA has a profound radioprotective effect. Eight out of ten (80%) mice survived the 10 Gray lethal radiation as compared to one out of ten (10%) with TPL alone. In a control experiment, without TPL or with PNA alone, all mice die on or about day 15. Therefore, the membrane impermeable PNA shows no radiation protective effect and does not protect against radiation damage at the intracellular level.

Figure 21:
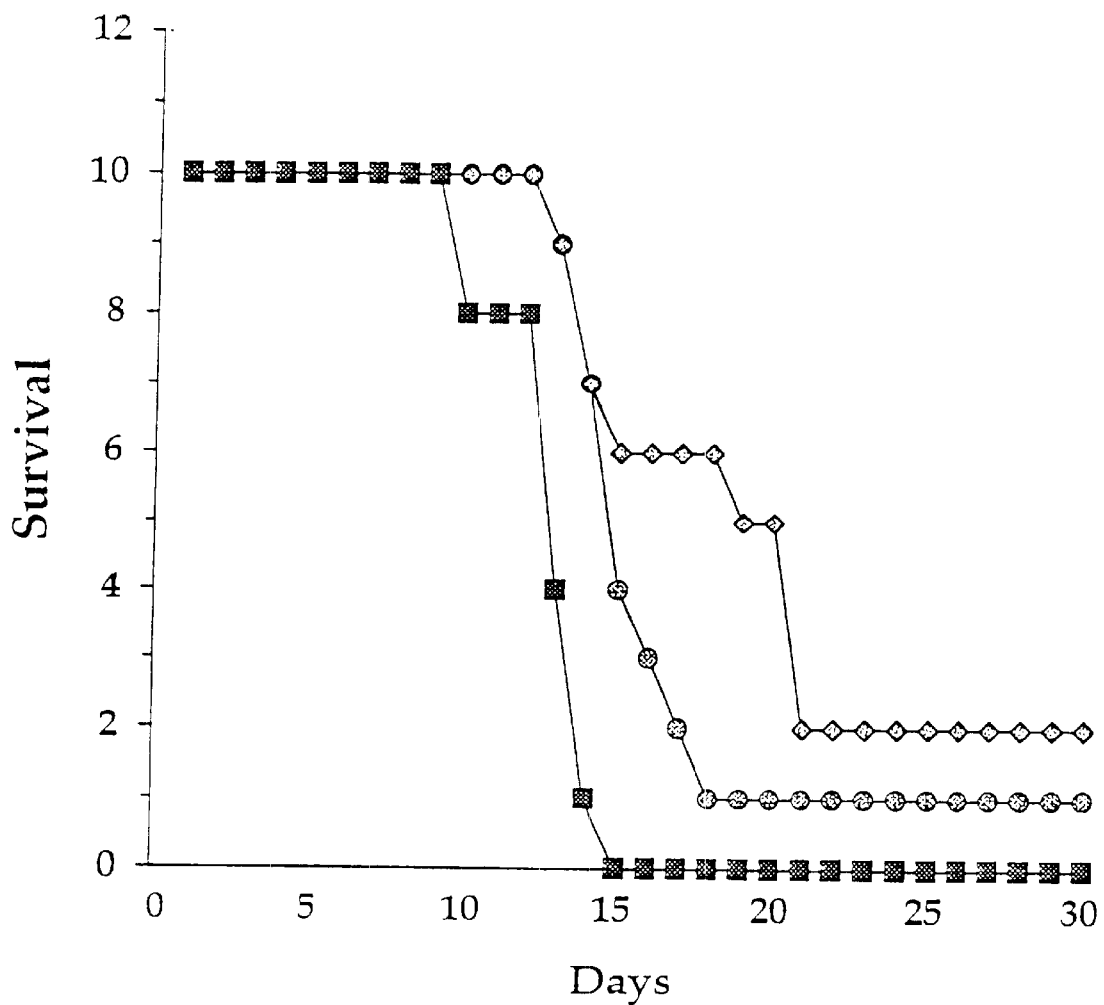
FIG. 21 shows the 30-day survival study of C57 mice exposed to 10 Gray irradiations after treatment with PNA 0.5 ml/mouse by intravenous administration followed by PBS buffer 10 minutes later (■), 0.5. ml PBS followed by 200 mg/kg of TPL 10 minutes later by intraperitoneal administration (●), polynitroxide albumin 0.5 ml/mouse by intravenous administration followed by 50 mg/kg TPL 10 minutes later (◇).

Referring to FIG. 21, the experimental data shows that PNA enables reduction in the TPL dose to achieve similar radiation protection. In this experiment, all ten mice died on day 15 when PNA (0.5 ml/mouse) was used alone. At one quarter the dose of TPL used in FIG. 20, the TPL concentration is reduced from 200 mg/kg to 50 mg/kg, the presence of PNA was able to protect two out of ten mice from lethal radiation (10 Gray). These results demonstrate that PNA can be used to reduce the dosage of TPL by a factor of four to achieve the same or better radiation protection.

Due to the ability to provide a systemic or physically localized radioprotectant effect, the use of the compositions of this invention is particularly advantageous in protecting a patient undergoing therapeutic radiation treatments. For example, a systemic or localized topical administration of a membrane permeable nitroxide can be combined with a topical administration of a polynitroxide albumin at the site where a radiation flux enters the body.

In one particular application, a topical ointment containing a polynitroxide albumin is applied to the scalp of a patient undergoing treatment for a tumor of the cranium. Concurrently therewith, a membrane permeable nitroxide is administered by an appropriate means, including for example suspension in the topical ointment. When the radiation dose is applied, the skin and hair follicles will be protected from the complete harmful effects of the radiation thereby lessening damage to the skin and reducing hair loss. An additional example involving brain tumors is particularly significant because of the high mortality rate and difficulty in successful surgical therapy. A whole body radiation protection can be provided by systemic administration of a membrane permeable nitroxide and topical and intravenous administration of a polynitroxide macromolecule with decreased permeability of the tumor. In such an example, an increased dose of radiation can be administered due to the whole body radioprotective effect of the invention. Due to selective permeability, the tumor region is more susceptible to radiation than the surrounding tissue and is thereby treated with greater efficacy. The selection of a number of variations and modifications of the above examples is well within the skill of those in the pertinent art as are other modifications which do not depart from the spirit of the invention.

EXAMPLE TEN

In Vivo Enzyme Mimic

As noted above, nitroxides (eog, TEMPOL) have been shown to have catalytic activity which mimics that of superoxide dismutase (SOD), the metalloenzyme which dismutates superoxide to hydrogen peroxide. Furthermore, in biological systems, nitroxides can interact with peroxidases and pseudoperoxidases to achieve an activity mimicking that of catalase, the enzyme which converts hydrogen peroxide to oxygen. Demonstrated herein is the use of nitroxides to mimic a superoxide oxidase to alleviate oxidative stress associated with metabolism of oxygen carriers. The biological effects of such activity derived from nitroxide-containing compounds include contributing to protection against cytotoxicity of reactive oxygen species by reducing oxidative stress. Nitroxides, when administered in vivo pursuant to this invention, display additional complex antioxidant enzyme-mimetic activities.

As noted above, when injected intravenously, TEMPOL has been shown to have very short plasma half-life. Due to its molecular size and charge characteristics, it readily leaves the vascular space. In many medical applications, it may be desirable to have an enzyme mimic which persists in the vascular space. This is achieved pursuant to this invention, by attaching a nitroxide compound to a macromolecule, such as hemoglobin and albumin, which is biologically safe and has a desirable plasma half-life.

A membrane-permeable nitroxide such as TPL, in its free radical state has been shown to have enzyme-mimic activity both in vitro and in vivo. However, in vivo, primarily in the intracellular space, it is rapidly reduced to its inactive hydroxylamine derivative (TPH) by bioreducing agents such as NADH. Previously, the reduction of the active TPL to the inactive TPH has been essentially irreversible on a stoichiometric basis. Thus, its effectiveness as a therapeutic and diagnostic tool is limited.

Pursuant to this invention, a multi-component nitroxide-containing composition has, as a first component, the membrane-permeable nitroxide which exists in a dynamic equilibrium between TPL (active) and TPH (inactive).

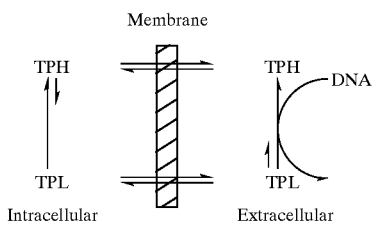

In vivo, the inactive TPH predominates (>90%). Both molecular species (TPL and TPH) readily cross the cell membrane and distribute into the intracellular and extracellular spaces.

A second component is a membrane-impermeable, macromolecular polynitroxide which distributes in the extracellular space, predominantly in the vascular space. The first and second components exhibit another enzyme mimetic function previously unknown in vivo, that of a synthetic reduced-nitroxide oxidase. For example, the polynitroxide albumin described herein as part of a multi-component system acts as a reduced-nitroxide oxidase by oxidizing TPH and TPL via a spin-transfer reaction. Thus, the macromolecular polynitroxide albumin acts as an enzyme mimic shifting the TPL/TPH equilibrium up to 90% TPL in both the intra- and extra-cellular spaces. This enzyme-mimic function is particularly useful where a high dose of TPL necessary to produce the requisite level of protection from radiation, ischemia, etc. would be toxic to the cells by overwhelming their cellular redox machinery.

For example, in the example of a dose of gamma radiation, when the dose becomes elevated, the quantity of low molecular weight, membrane permeable nitroxide necessary to provide meaningful radioprotective effects can become so large that the cells redox state is disrupted, thereby resulting in toxicity.

To overcome the toxicity hurdle, the multi-component system of this invention regenerates the reduced TPH to TPL. This system can be used in any application where an active nitroxide is desirable in vivo.

Figure 17:
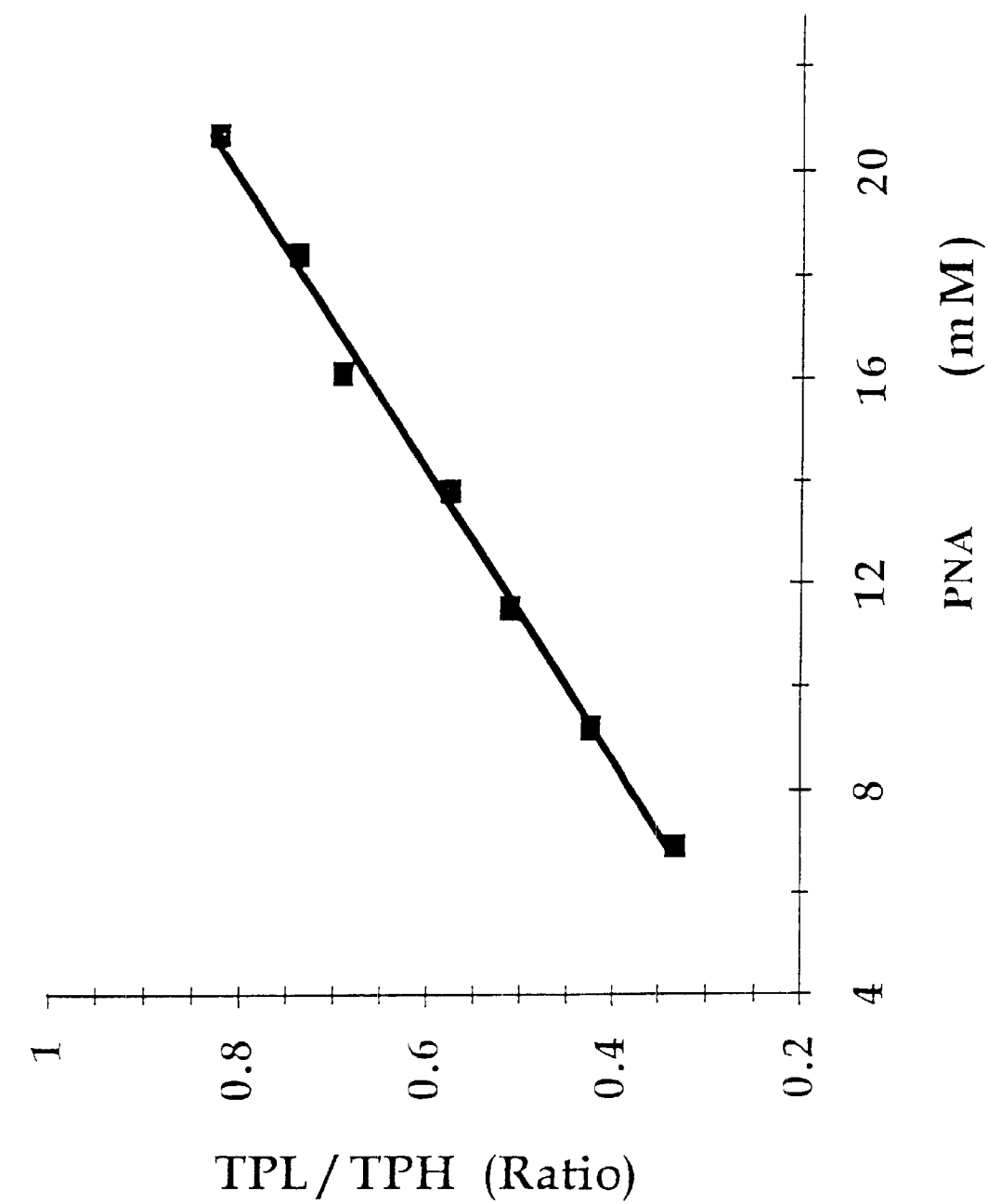
FIG. 17 shows the conversion of TPH to TPL by PNA TPH at fixed concentration of 25 mM was mixed with increasing concentrations of the PNA in sodium phosphate buffer 50 mM, Ph 7.6. The ratio of TPL/TPH was plotted against 25 mM PNA concentrations. This ratio represents conversion efficiency. TPL concentration was determined by incubating 25 Mm of TPH and seven different concentrations of PNA at room temperature for 30 minutes followed by 10 KD membrane centrocon separation for one hour at 5000 xg. The high field EPR peak intensities of TPL in the filtrate were calibrated with TPL standard curve and plotted as shown.

The EPR spectra of TPL TPH and a polynitroxide albumin is shown in FIGS. 15A, 15B, and 15C, respectively. Demonstration of a reduced nitroxide oxidase activity is shown by the reoxidation (spin-transfer) from TPH (EPR silent FIG. 15B) to the macromolecular polynitroxide (FIG. 15C) to and its conversion to TPL (EPR active) (FIG. 15A) is carried out as follows: (1) equimolar ratios of TPH to a macromolecular polynitroxide are incubated at room temperature for 30 minutes; (2) the reaction mixture is centrifuged through a 10 kd cut-off membrane; and (3) The EPR spectrum of the filtrate is recorded and shown in FIG. 15B. The quantitative conversion of TPH to TPL is shown in FIG. 17.

A synthetic reduced nitroxide oxidase (polynitroxide albumin) is prepared by allowing human serum albumin (HSA, 25% Baxter Healthcare) to react with 40 molar equivalents of 4-(2-bromoaceamido)-TEMPO or Br-TEMPO at 60° C. for ten hours with mixing. The resulting mixture, containing 15 ml of HSA and 165 mg or Br-TEMPO in a vacutainer tube, is sterilized with a 0.22 micron filter and transferred into a 150 ml stirred cell equipped with a 10 kd cutoff membrane (Filtron Technology Corp.). The filtered reaction mixture is washed with Ringers solution until the filtrate contains less than 1 uM of Free TEMPO as detected by ESR spectroscopy. The bright orange colored retenate is concentrated to 25% HSA and again sterile-filtered into a 10 ml vial and stored at 4° C. until used. Ŧdemonstrate the in vivo enzyme-like conversion of TPH to TPL, the $^{15}$N stable isotope analogue of TPL is injected into the tail vein of a cannulated mouse and the EPR signal is directly monitored in the tail. The direct intravenous injection of a 0.5 ml of TPL (40 mM) solution in the anesthetized mouse demonstrates that the plasma half-life of TPL is approximately 2 minutes. Referring to FIG. 18, with a follow-on injection (~30 minutes later) of a mixture comprising a macromolecule polynitroxide and a stable isotope $^{15}$N TPL, a biphasic change in the peak intensity of $^{15}$N TPL exists. Initially, a decrease in $^{15}$N TPL signal intensity is attributed to the diffusion of TPL out of the vascular space followed by its intra-cellular reduction. This rate of diffusion is initially faster than the rate of reoxidation of the TPH to TPL based on the slower re-appearance of the $^{15}$N TPL signal intensity in FIG. 18. Although the reoxidation of TPH to TPL is slower than the initial diffusion/reduction rate, it is faster than the steady state intracellular reduction rate of TPL. Thus, the reappearance of the TPL signal shown in FIG. 18 detects the reoxidation of TPH to TPL thereby demonstrating a synthetically produced reduced nitroxide oxidase activity in vivo in mice. See also FIGS. 18B–18D.

EXAMPLE ELEVEN

Ischemia and Reperfusion Injury—Cerebrovascular Ischemia in Stroke

As noted above, nitroxide-containing compounds can be used in medical imaging. A particularly useful application is in obtaining images of ischemic tissues in the heart and elsewhere, because valuable information regarding oxygen metabolism and reperfusion injury can be obtained.

However, the rapid reduction of free nitroxides in vivo limits the utility of free nitroxides in this application. However, pursuant to this invention, it is possible to enhance the imaging capability to spatially resolve ischemic tissue in the heart, to monitor the development of myocardial ischemia, to study the development of the myocardial reperfusion phase, and to observe in real time the hypoxic state of tissues or organs. Referring to FIGS. 22, 23, and 25, ERI images of an isolated rat heart infused with $^{15}$N-TEMPOL and a polynitroxide albumin are shown.

In FIG. 24, the intensity of the EPR signal is shown as a function of the duration of ischemia. In the lower curve, 2 mM of TEMPOL is infused into an ischemic heart. The upper curve traces the original intensity of 2 mM TEMPOL together with a polynitroxide albumin (4 g/dl of albumin at 42 moles of TEMPOL per mole of albumin). The data demonstrate that the signal intensity is substantially greater, and is maintained, when the composition of this invention is used. FIG. 25 shows the viability of imaging at ischemic tissue from 3-D spatial images. The progression of images traces the progress of ischemia over approximately 125 minutes.

Figure 26:
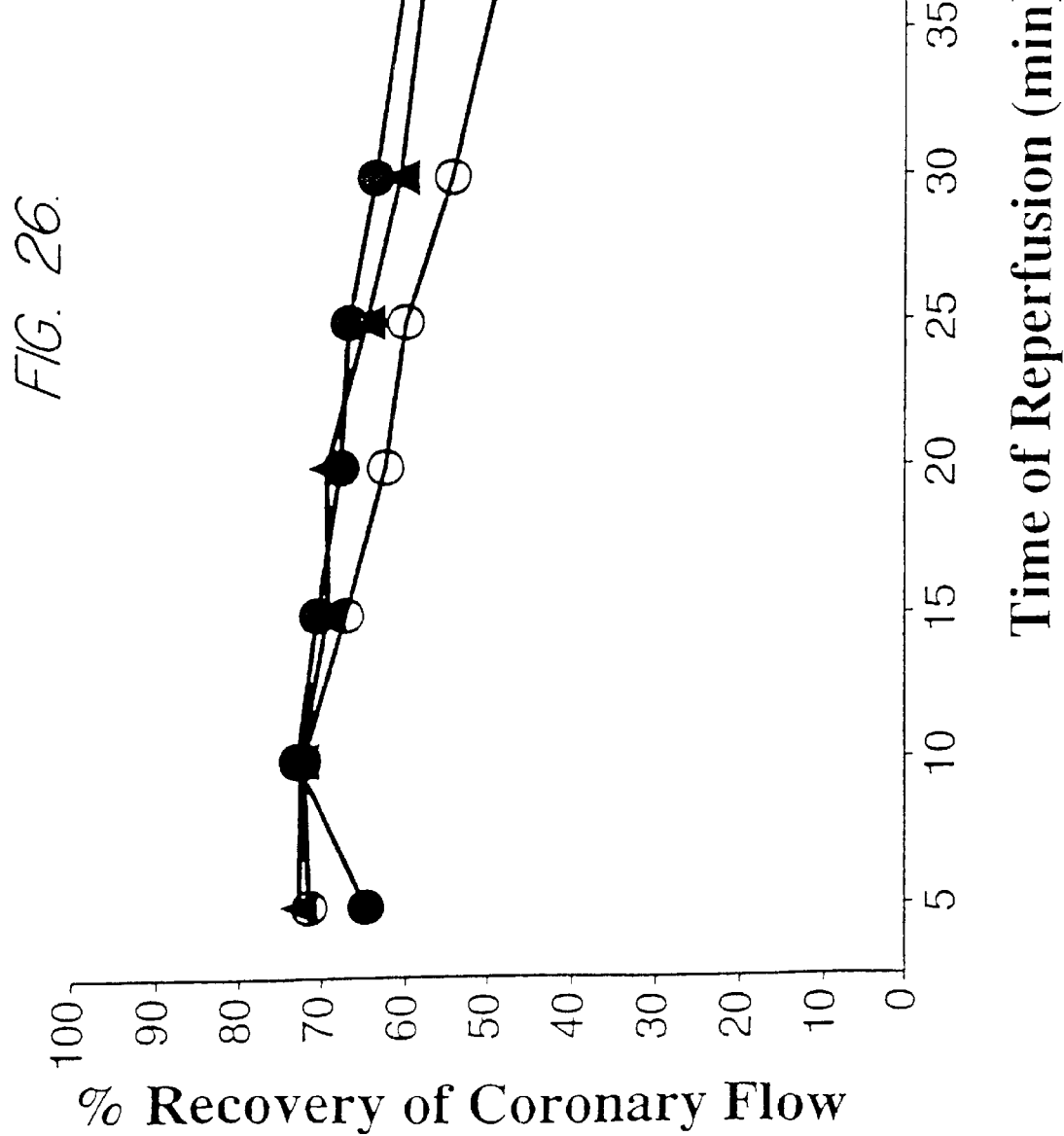
FIG. 26 shows a measurement of the recovery of coronary flow in untreated control hearts (○), treated with TPL 2 mM (●), and PNA (4 g/dl)+TPL 2 mM (▲) Hearts were subjected to 30 min. of global ischemia followed by 45 min. reflow.
Figure 27:
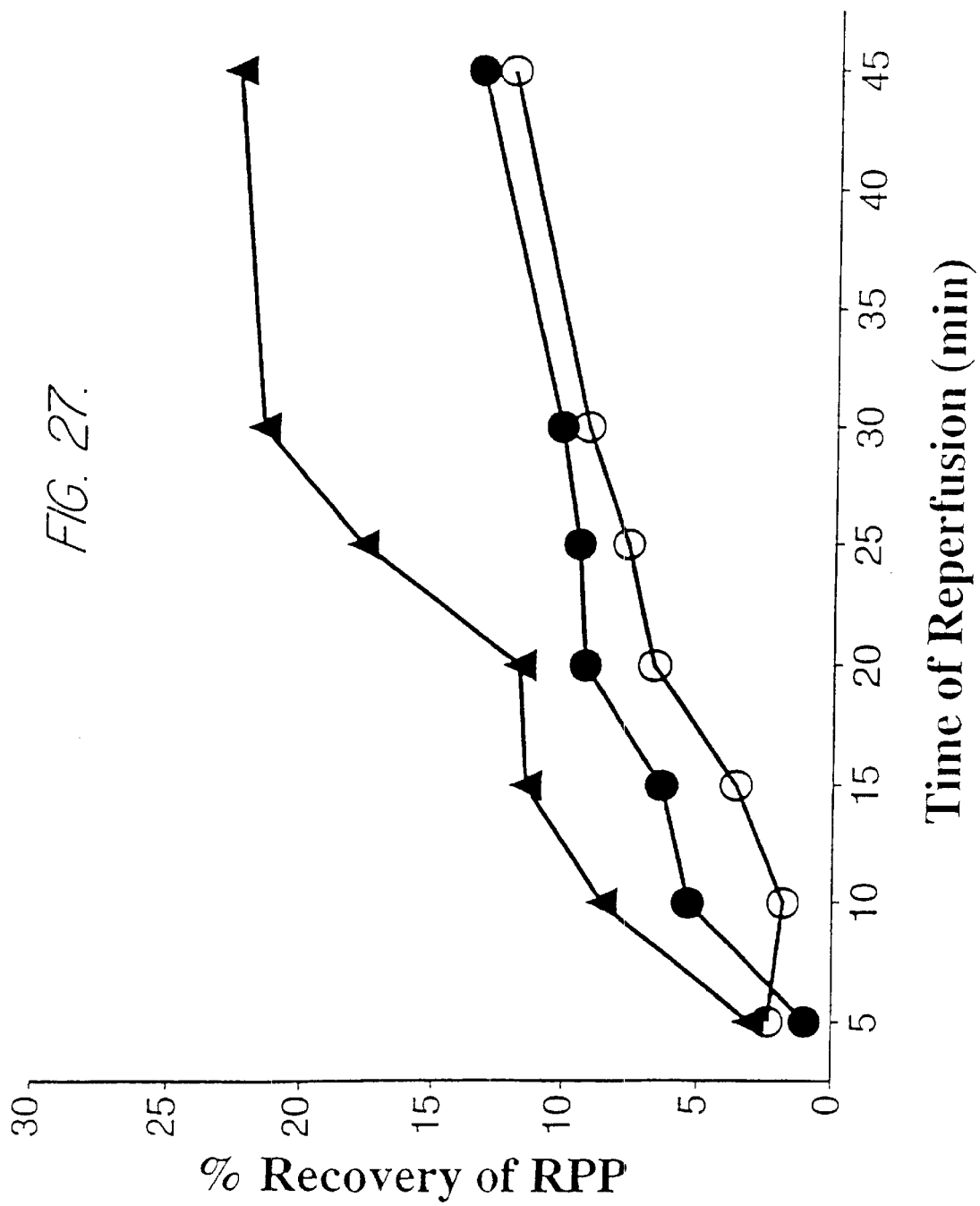
FIG. 27 shows the measurement of the recovery of rate pressure product (RPP) in untreated control hearts (○), treated with TPL 2 mM (●), and PNA 4 g/dl+TPL 2 mM (▲). Hearts were subjected to 30 min. of global ischemia followed by 45 min. reflow.

Apart from demonstrating diagnostic utility, the polynitroxide albumin and TEMPOL combination protects the heart from ischemic reperfusion injury. FIG. 26 shows that a nitroxide alone in combination with PNA does not affect the recovery of coronary flow. However, FIG. 27 shows the substantially improved recovery of RPP (rate pressure product) following 30 minutes of global ischemia followed by 45 minutes of blood flow is only observed in the presence of both. Furthermore, edema of the heart as a result of ischemic/reperfusion injury was prevented.

Figure 28:
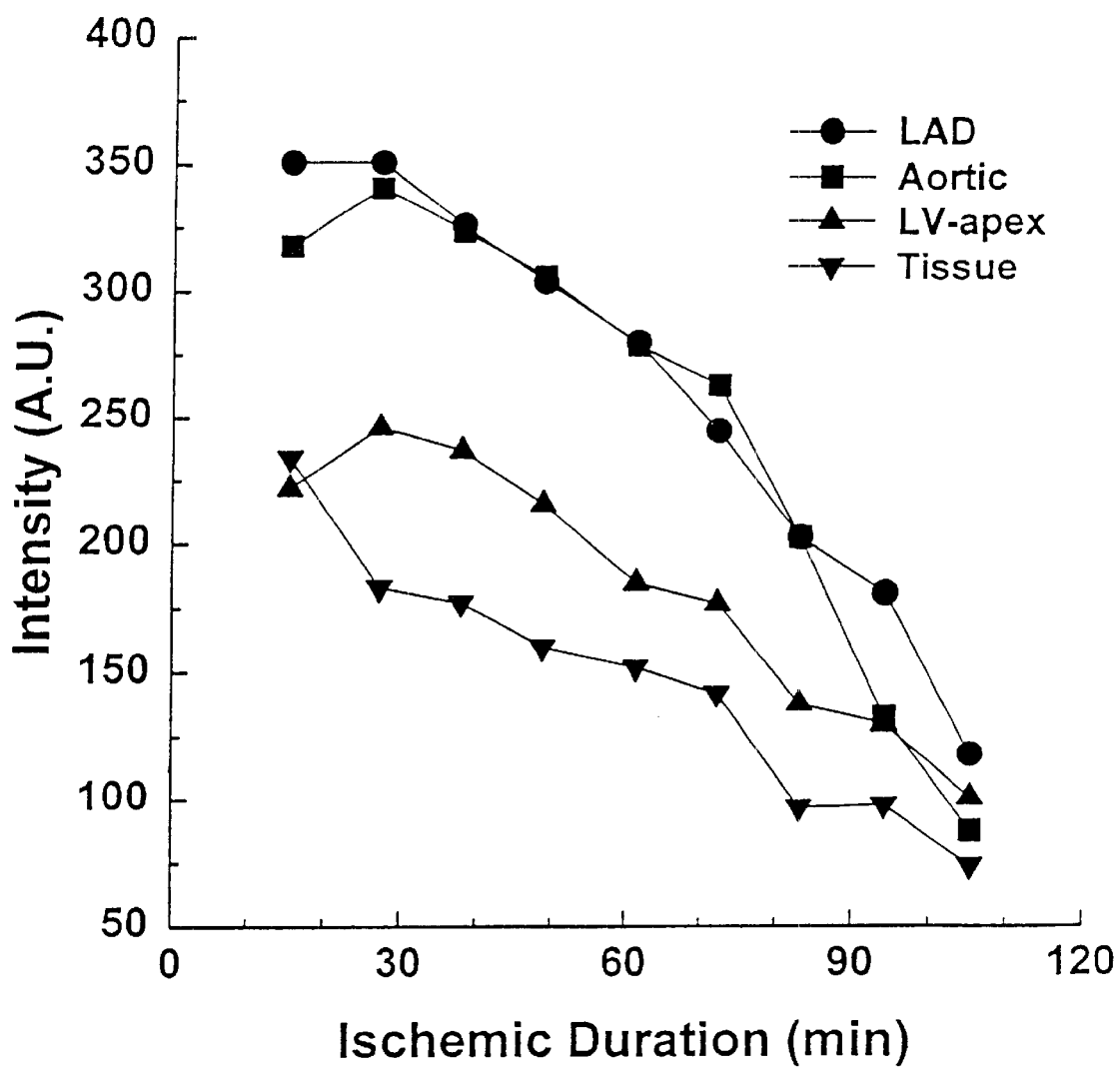
FIG. 28 is a graph of the EPR signal intensity of TEMPOL vs. durations of ischemia in the rat heart treated with $^{15}$N-TPL+PNA obtained from images shown in FIG. 25. The intensity values were obtained at specific locations of the corresponding 3-D spatial images as follows: LAD (●), Aortic (■), LV-apex (▼) and tissue (▲).

Referring to FIG. 28, the $^{15}$N-TPL concentrations in various anatomical regions of the ischemic heart are elevated during over 100 minutes of ischemia. Elevation of TPL tissue concentration may contribute to the protection of cardiac function (FIG. 27) by PNA.

To demonstrate that PNA provides protection from ischemia/reperfusion injury in the brain and central nervous system as well as in the heart and cardiovascular system (as described above), CD-1 mice at 3 months of age, body weight 35–40 g were anesthetized with 1.5% isoflurane in a continuous flow of 30% oxygen/70% nitrous oxide. The animals were subjected to middle cerebral artery (MCA) occlusion and reperfusion by the method of Yang et al. (*Stroke* 25: 165–170, 1994) with occlusion of the ipsilateral common carotid artery (CCA). PNA or a control solution of human serum albumin was injected intravenously just before one hour of MCA occlusion (pre-ischemia group) or just after reperfusion following one hour of ischemia (post-reperfusion group). The dose was 0.5% of body weight, v/w). Body temperature was maintained within the range 36.5–37.5° C. during the surgery. Mean arterial pressure and blood gasses were measured in four animals to insure a valid control group.

Twenty-four hours after reperfusion, animals were assessed for neurological deficit as described by Bederson et al. (*Stroke* 17: 472–476, 1986). Neurological deficits were scored on the following scale: 0+no observable deficit, 1+failure to extend right forepaw, 2+circling to the right, 3+falling to the right, 4+cannot walk spontaneously. Following the neurological assessment, the animals were decapitated and the brains rapidly removed and frozen for histological analysis. Coronal sections 20 Mm thick were made at intervals of 0.5 mm from the anterior tip of the brain and strained with cresyl violet in order to evaluate infarction (n+7 animals). Infarct volume was calculated by integrating infarct size (measured in mm$^2$ in the serial sections.

Figure 30:
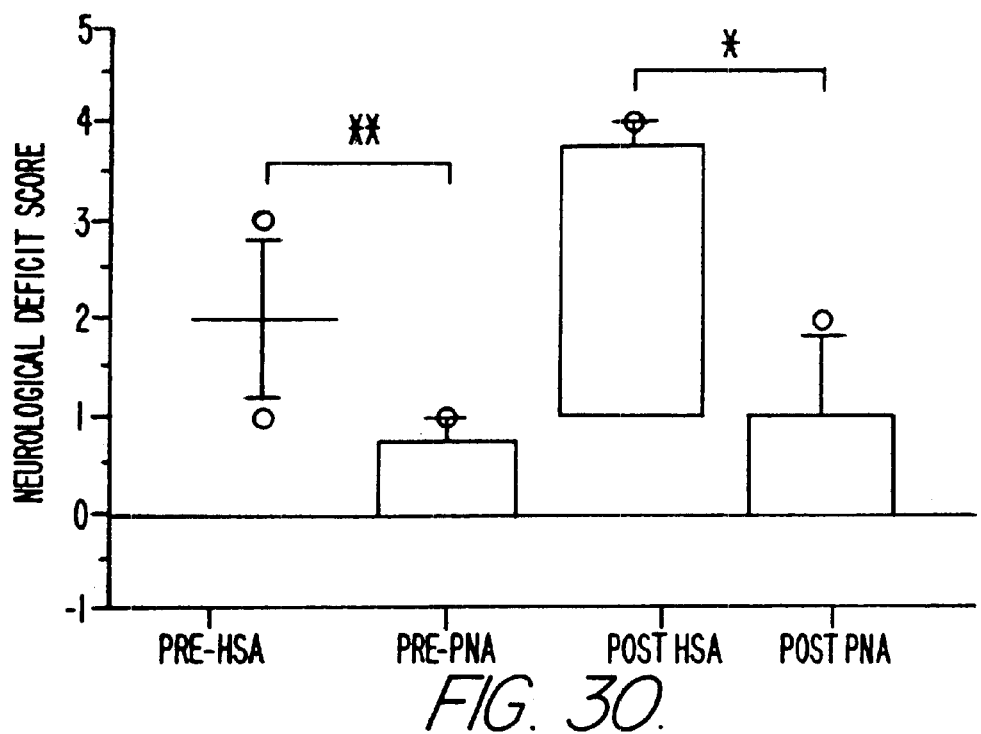
FIG. 30 shows the reduction in neurological deficit in mice treated with PNA. Animals were subjected to 1 hour of focal cerebral ischemia by MCA/CCA occlusion, followed by reperfusion. Animals were treated before the onset of ischemia with PNA (Pre PNA) or human serum albumin (HSA), or immediately after reperfusion (Post PNA, Post HSA), and assessed for neurological status after 24 hours of reperfusion. The dose of PNA or human serum albumin was 0.5% of body weight, v/w.
Figure 31:
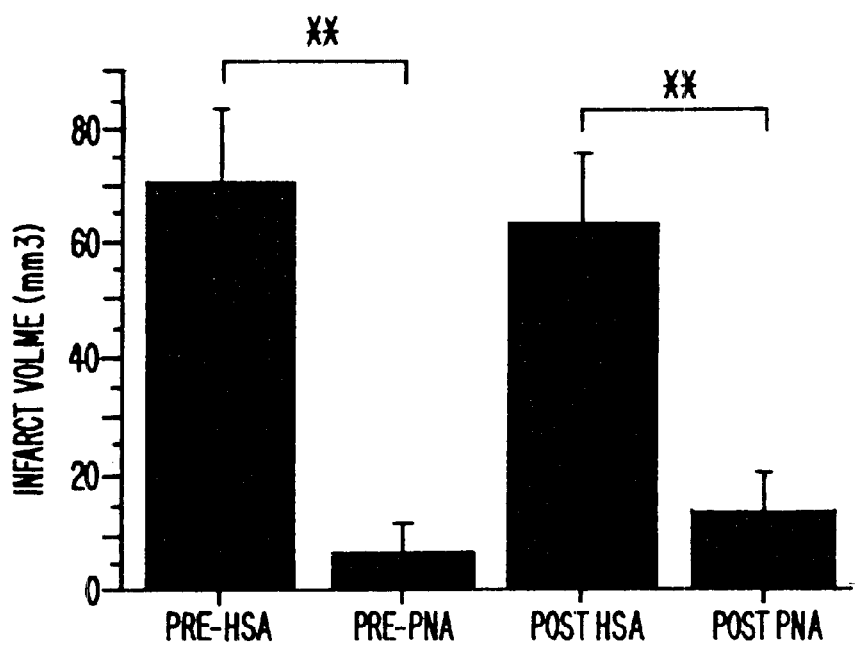
FIG. 31 shows the reduction in infarct volumes in mice treated with PNA. Animals were subjected to 1 hour of focal cerebral ischemia by MCA/CCA occlusion followed by reperfusion. Animals were treated before the onset of ischemia with PNA (Pre PNA) or human serum albumin (Pre HSA), or immediately after reperfusion (Post PNA, Post HSA), and sacrificed after 24 hrs of reperfusion for histological analysis. The dose of PNA or albumin was 0.5% of body weight, v/w. Infarct volumes were calculated by integrating infarct areas in serial coronal sections taken at 0.5 mm intervals from the anterior tip of the brain. Results are expressed as mean±SEM, n=7.

Referring to FIG. 30, PNA treatment either before the onset of ischemia or immediately after reperfusion significantly reduces neurological deficit as measured 24 hrs. post-reperfusion (n=7). Referring now to FIG. 31, PNA treatment either before cerebral ischemia or immediately after reperfusion significantly reduced infarct volumes as measured 24 hrs. post-reperfusion. In animals treated before the onset of ischemia, infarct volumes were 6.956 mm$^3$±4.910 in PNA-treated animals, vs. 70.378 mm$^3$±12.812 in control animals. In animals treated immediately after reperfusion, infarct volumes were 13.710 mm$^3$±6.644 in PNA-treated animals, vs. 62.636 mm3±12.372 in control animals.

Figure 32:
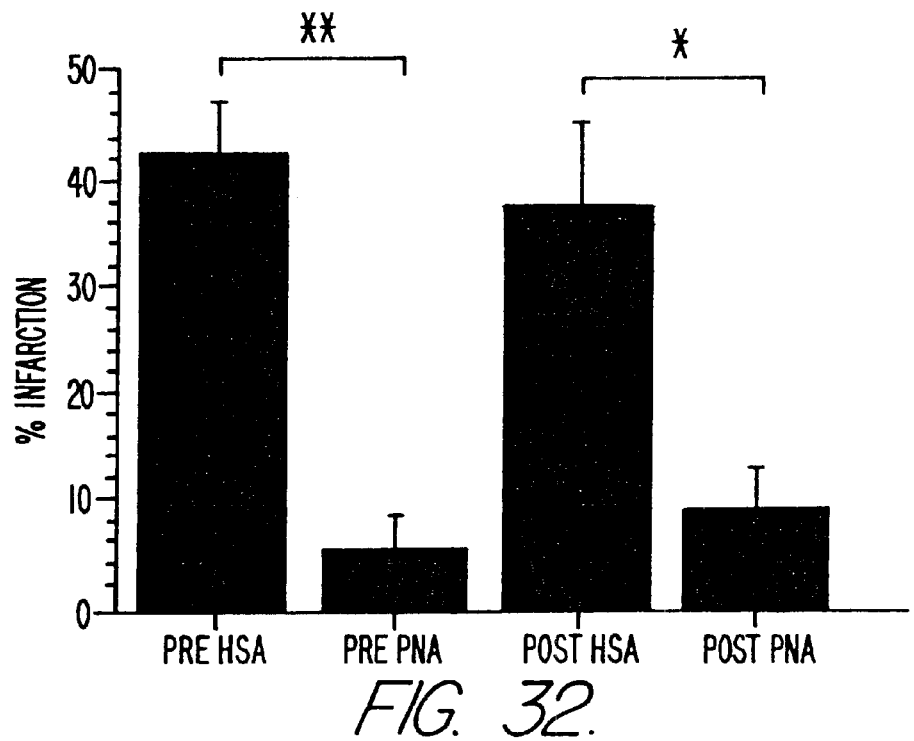
FIG. 32 shows the reduction in percentage of infarction in mice treated with PNA. Animals were subjected to 1 hour of focal cerebral ischemia by MCA/CCA occlusion, followed by reperfusion. Animals were treated before the onset of ischemia with PNA (Pre PNA) or human serum albumin (Pre HSA), or immediately after reperfusion (Post PNA, Post HSA), and sacrificed after 24 hrs of reperfusion for histological analysis. The dose of PNA or albumin was 0.5% of body weight, v/2. Percent infarction was calculated as (infarct volume/ipsilateral hemisphere volume)×100. Results are expressed as mean±SEM, n=7.
Figure 32A:
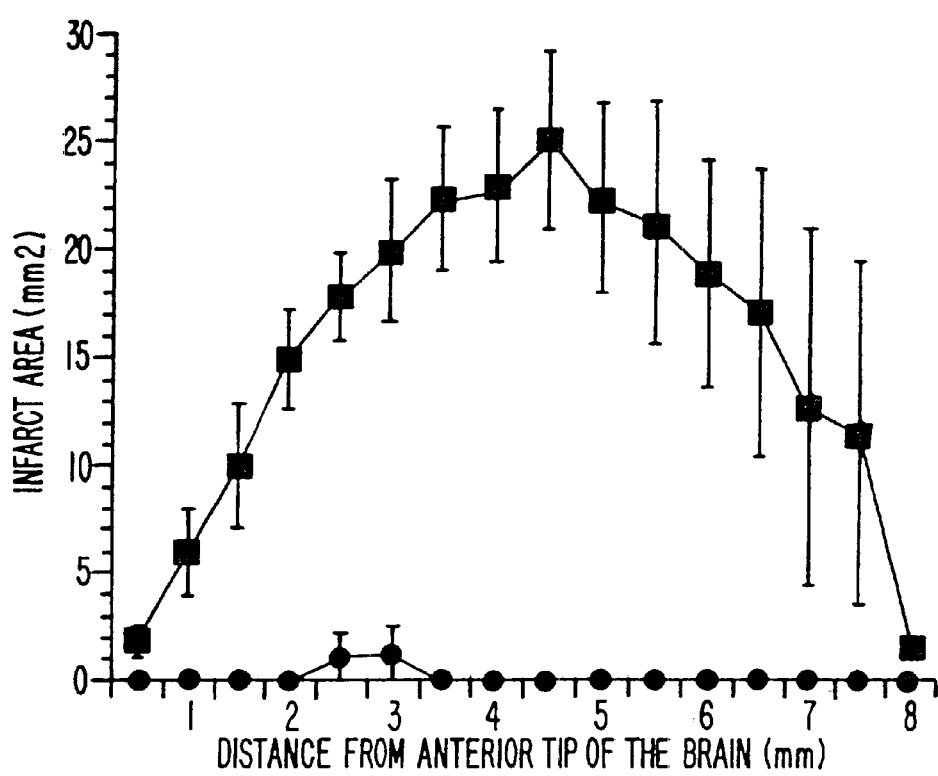
FIG. 32A shows quantitation of stroke injury in serial sections of the brains of control vs. PNA-treated mice. A series of 20 μm-thick coronal histologic sections was taken at 500 μm intervals from the anterior tip of the brain, and cerebral ischemia was quantitated as infarcted area (mm$^2$, mean±S.D.) per section. The difference in the area of the infarction in PNA-treated mice (●) compared with controls (■) is the area between the two lines (p<0.05 by Student's t-test).
Figure 33:
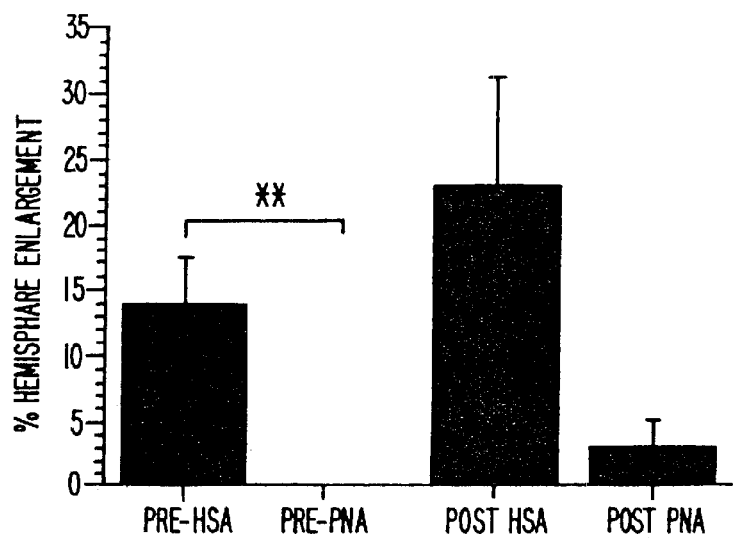
FIG. 33 shows reduction in hemisphere enlargement in mice treated with PNA. Animals were subjected to 1 hour of focal cerebral ischemia by MCA/CCA occlusion, followed by reperfusion. Animals were treated before the onset of ischemia with PNA (Pre PNA) or human serum albumin (Pre HSA), or immediately after reperfusion (Post PNA, Post HSA), and sacrificed after 24 hours of reperfusion for histological analysis. The dose of PNA or albumin was 0.5% of body weight, v/w. Percent hemisphere enlargement was calculated as (ipsilateral hemisphere volume−contralateral hemisphere volume contralateral hemisphere volume)×100. Results are expressed as mean±SEM, n=7.

FIGS. 32 and 32A show % infarction values and infarct area respectively, which were calculated from infarct volume and ipsilateral hemisphere volume. In animals treated with PNA pre-ischemia, the % infarction value was 5.148%±3.237, compared with 42.462%±5.001 in pre-ischemia controls. In animals treated immediately post-reperfusion, these values were 9.210%±4.080 in PNA-treated animals and 37.782%±8.030 in controls (mean±SEM, N+7). FIG. 33 shows that PNA treatment either before the onset of ischemia or immediately post-reperfusion significantly reduced hemisphere enlargement as measured 24 hrs. post-reperfusion. Animals treated with pre-ischemia showed essentially no enlargement (0.094%±0.094), while pre-ischemic controls showed 13.916%±3.491 enlargement. Animals treated with PNA at the onset of reperfusion showed 3.056%±2.053 enlargement, compared with the control value of 22.994%±8.562.

The data in FIGS. 30–33 shows that PNA treatment either before the onset of focal cerebral ischemia or immediately after reperfusion gave statistically significant protection against stroke injury as measured by neurological deficit, infarct volume, % infarction, and hemisphere enlargement. As can be seen, the neurological deficit scores correlated well with histological measures of cerebral edema and infarction.

Figures 34A, 34B:
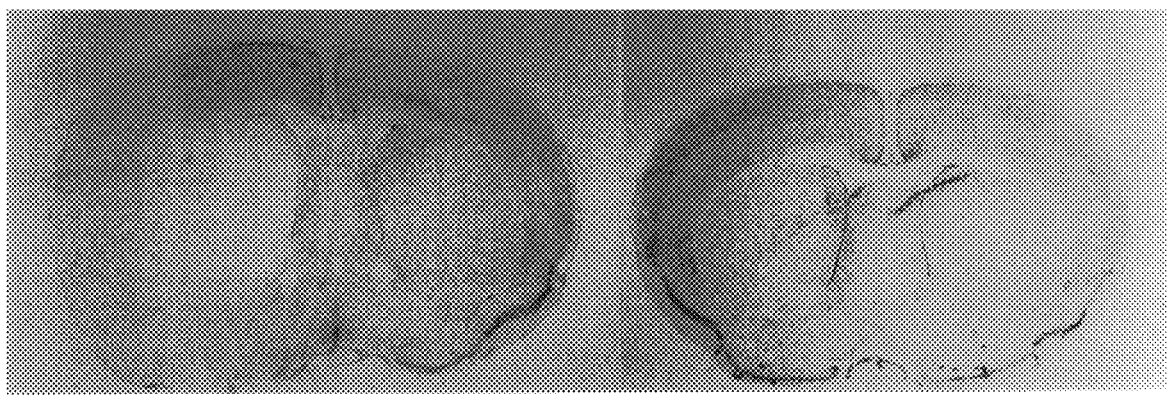
FIGS. 34A and 34B show representative coronal sections showing reduction in cerebral infarction in PNA-treated vs. control mice subjected to focal cerebral ischemia (1 hr) and reperfusion (24 hr). 20 μm-thick sections were stained with cresyl violet, which is poorly taken up by ischemic tissue.
Figure 34C:
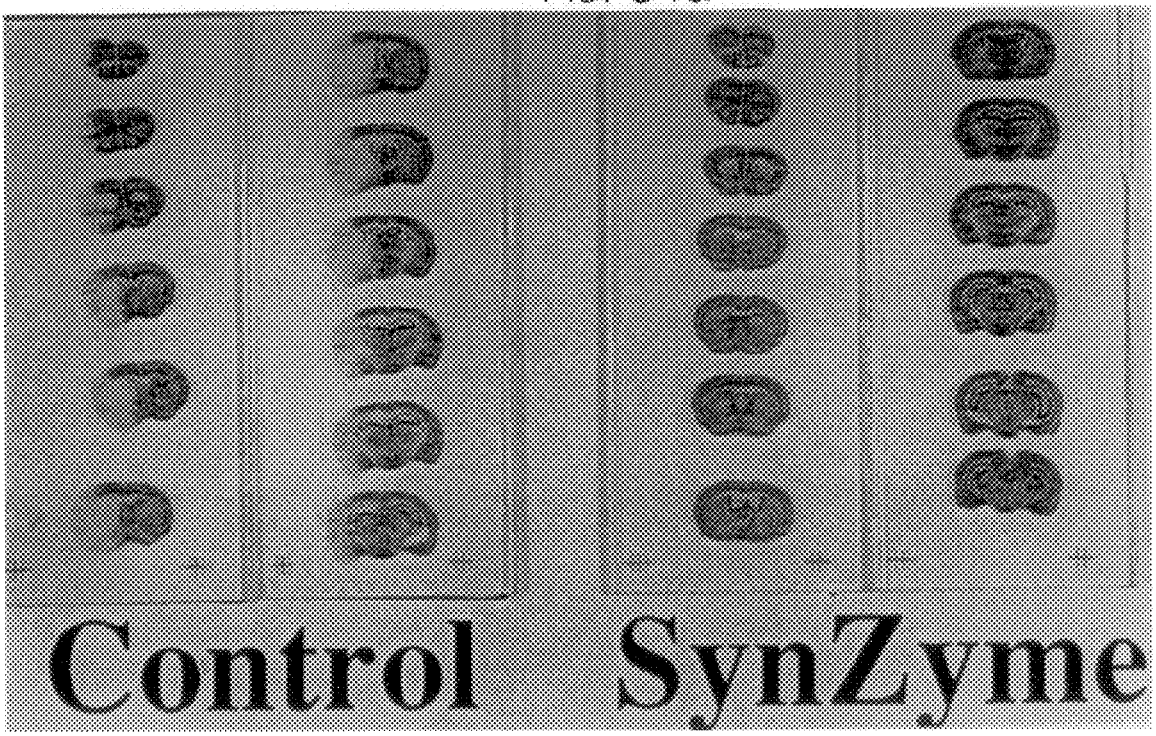
FIG. 34C is representative histologic sections showing reduction in stroke injury in PNA-treated vs. control mice. Animals were subjected to focal cerebral ischemia (1 hour) and reperfusion (24 hours). Treated mice received intravenous PNA before ischemia and at the onset of reperfusion. Each dose was equivalent to 1% of body weight (v/w). In order to demonstrate the anatomic extent of ischemia, coronal sections 20 μm thick were made at 500 μm intervals from the anterior tip of the brain, and stained with cresyl violet. Ischemic tissue appears unstained. The untreated animals (left-hand panel) show ischemic damage of essentially the entire hemisphere. In striking contrast, the PNA-treated animals (right-hand panel) show normal histology throughout the brain.

To determine the comparative level of protection provided by PNA in comparison with another compound which functions by alleviating a free radical cascade in the vascular space, a study was performed to compare the protection provided by PNA in the normal mouse with the comparatively high degree of protection provided by overexpressed SOD in the SOD-1 Tg mouse. Chan, P. H., C. J. Epstein, H. Kinouchi, H. Kamii, G. Yang, S. F. Chen, J. Gafni, and E. Carlson (1994). SOD-1 transgenic mice as a model for studies of neuroprotection in stroke and brain trauma. *Ann. N.Y. Acad. Sci.* 738:93–103. Chan, P. H., C. J. Epstein, H. Kinouchi, S. Imaizumi, E. Carlson, and S. F. Chen (1993). Role of superoxide dismutase in ischemic brain injury: Reduction of edema and infarction in transgenic mice following focal cerebral ischemia. In *Molecular Mechanisms of Ischemic Brain Damage*, K. Kogure and B. K. Siesjo, eds. Amsterdam: Elsevier. pp. 97–104. Kinouchi, H., C. J. Epstein, T. Mizui, E. Carlson, S. F. Chen and P. H. Chan (1991). Attenuation of focal cerebral ischemic injury in transgenic mice overexpressing CuZn superoxide dismutase. *Proc. Natl. Acad. Sci. USA* 88:11158–11162. Imaizumi, S., V. Woolworth, and R. A. Fishman (1990). Liposome-encapsulated superoxide dismutase reduces cerebral infarction in cerebral ischemia in rats. *Stroke* 21: 1312–1317. Liu, T. H., J. S. Beckman, B. A. Freeman, E. L. Hogan, and C. Y. Hsu (1989). Polyethylene glycol-conjugated superoxide dismutase and catalase reduce ischemic brain injury. *Am. J. Physiol.* 256: H586–H593. Chan, P. H., S. Longar, and R. A. Fishman (1987). Protective effects of liposome-entrapped superoxide dismutase on post-traumatic brain edema. *Ann. Neurol.* 21: 540–547. PNA at 1% of body weight v/w (200 μl in a 20 g mouse) was injected intravenously into an anesthetized animal. Ten minutes later, the middle coronary artery (MCA) was occluded by luminal blockade using a nylon suture. After one hour of ischemia, reperfusion, and after 24 hours of reperfusion, animals were assessed for neurological function and sacrificed for histological measurement of infarction and edema. Referring to FIGS. 34A and 34B, a representative coronal section from the brain of a control mouse treated mouse were stained with cresyl violet, which stains normal tissue such that areas of ischemic damage do not take up the stain. The control brain shows massive ischemic injury of the involved hemisphere and comparison of that hemisphere with the contralateral one in the same brain showing substantial edema. In contrast, in the brain of the treated mouse, the involved hemisphere is normal and symmetric with the contralateral one in terms of size, shape, and staining density. Serial sections as shown in FIG. 34C indicate the anatomic distribution of ischemic injury throughout the brain of a representative control animal, and the normal appearance of the brain of a representative treated animal. The areas of infarction in the control animal vs. the PNA treated animal are quantitated in FIG. 32A, showing that PNA treatment gives essentially complete protection against infarction in this model. The following table summarizes data on the reduction in neurological deficit, percent infarction (calculated from infarction areas in serial sections), and hemisphere enlargement in the treated animals. Thus, the infusion of PNA provides a greater degree of protection than does threefold-overexpressed transgenic SOD.

Protection against stroke injury in the mouse

|  | Control | PNA |
| --- | --- | --- |
| Neurological Deficit Score [1] | 5.5 | 2.0 |
| % Infarction [2] | 58.0 ± 9.4 | 1.9 ± 1.9 |
| % Hemisphere Enlargement [2] | 24.1 ± 6.2 | 1.7 ± 0.9 |

PNA (1% of body weight v/w, 200 μl per 20 g mouse) was administered both 10 minutes before the onset of 1 hour of ischemia and at the onset of reperfusion. Animals were assessed for neurological function and sacrificed for histology after 24 hours of reperfusion.
[1] Neurological deficit is expressed as mean rank of deficits divided into four groups; the PNA group showed significantly less deficit ($p < 0.05$ by Mann-Whitney U test).
[2] Percent infarction and hemisphere enlargement in animals that survived to 24 hours are expressed as mean ± S.E.M.; the PNA group showed reductions which were significant at $p < 0.05$ by Student's t-test.

There is also increasing evidence of significant incidence of ischemic injury in surgical patients undergoing cardiopulmonary bypass and other surgical procedures resulting from embolism and/or hypotension, with subsequent reperfusion injury. The principal target organs are the brain, the heart, and the kidney.

Figure 35:
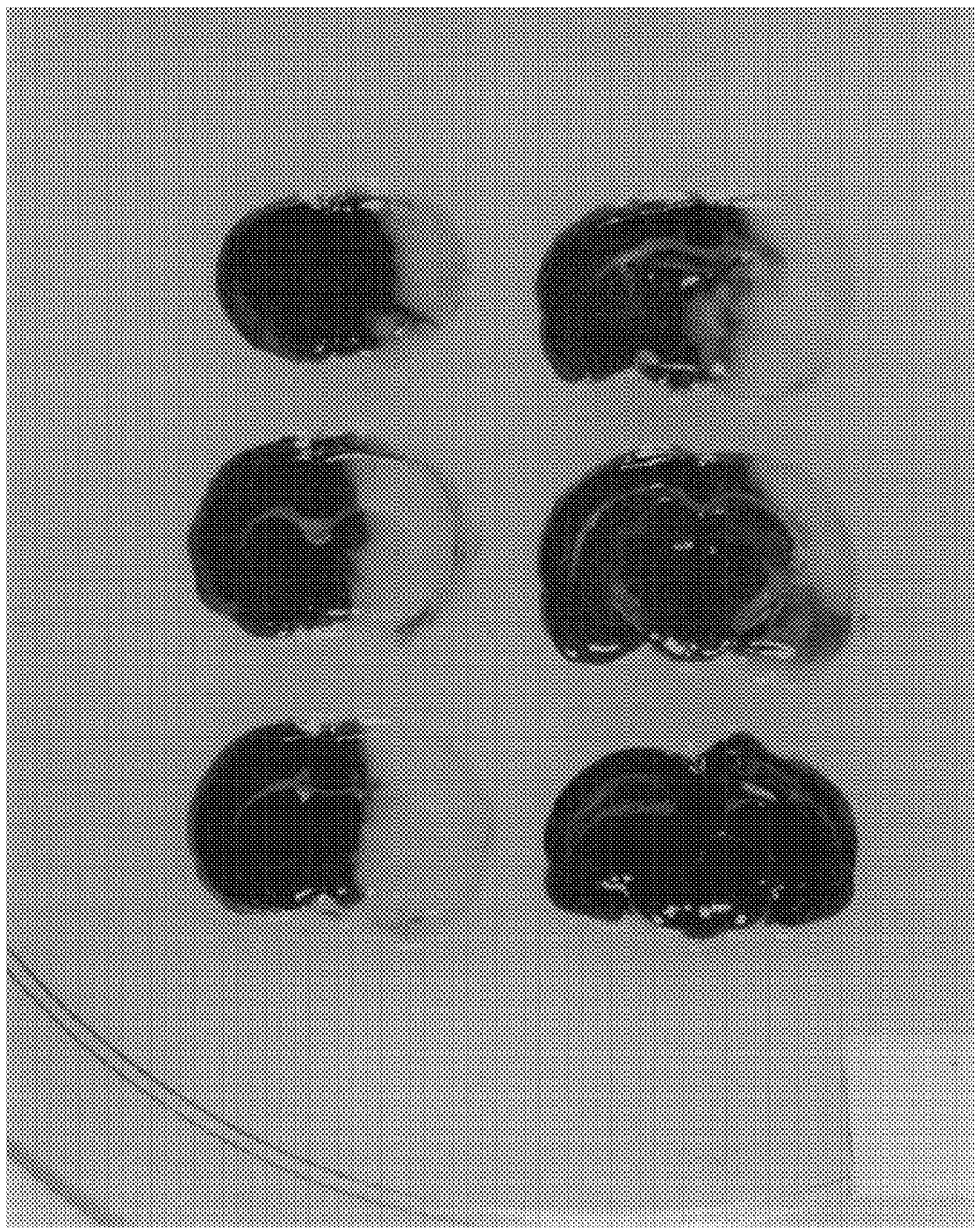
FIG. 35 is a series of stained coronal sections of the rat brain of an animal infused with PNA and stained after two hours of suture occlusion of the MCA.
Figure 36:
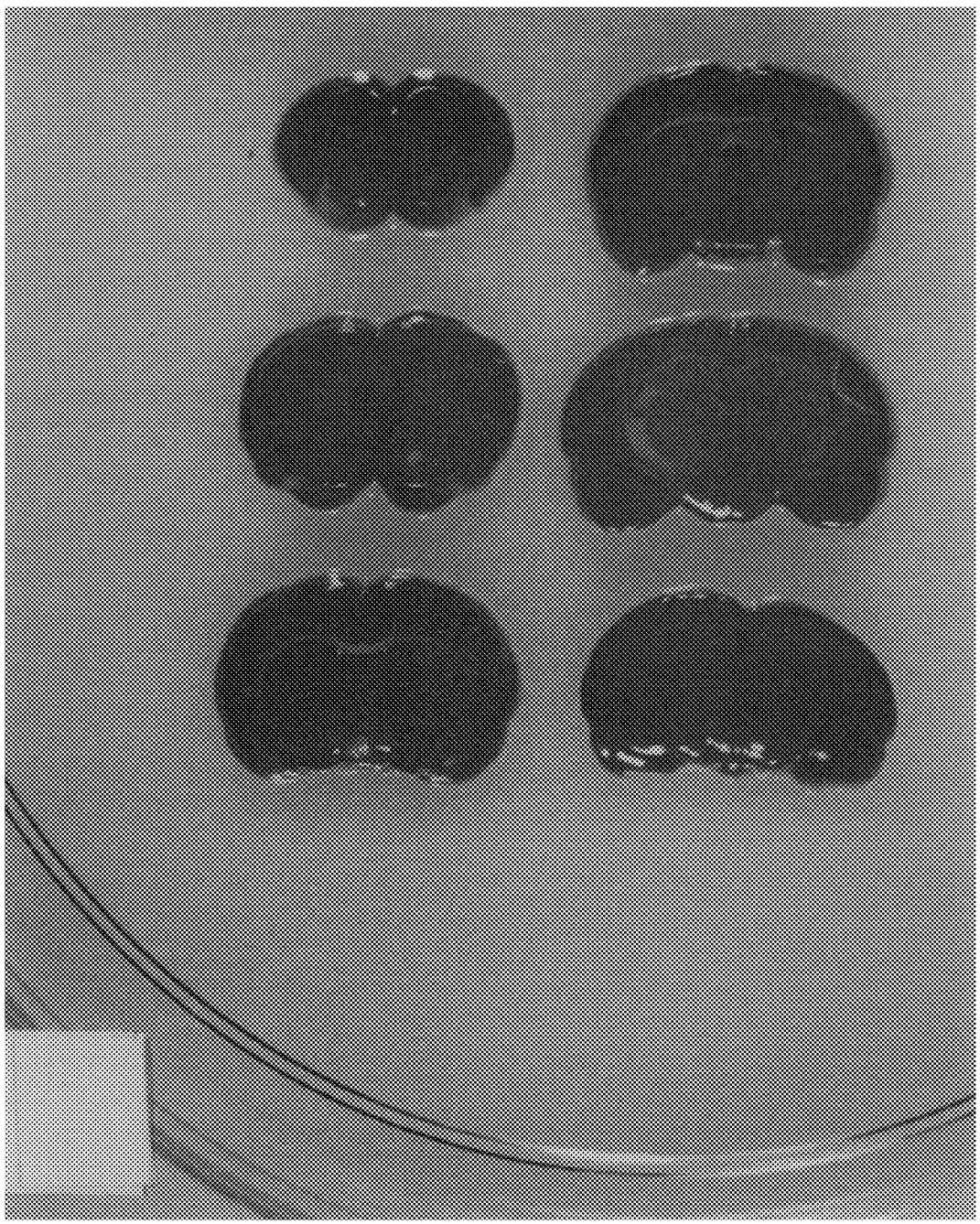
FIG. 36 is a series of stained coronal sections of the rat brain of an animal infused with a saline control and stained after two hours of suture occlusions of the MCA.

As a model of prophylactic therapy in the surgical/perioperative stroke setting, PNA was administered to mice both before MCA occlusion and after reperfusion. Because albumin alone may provide modest protection against cerebral ischemia, PNA was tested with both HSA and saline as controls. Referring to FIGS. 35 and 36, the saline-treated rat of FIG. 35 shows massive infarction, while the PNA rat of FIG. 36 shows no grossly visible infarction. Histologic analysis (FIGS. 37A and 37B) shows that saline-treated rats had a mean infarct volume of $192\pm17$ mm$^3$. Treatment with albumin gave a significantly smaller ($p<0.01$) mean infarct volume of $81\pm26$ mm$^3$, and treatment with PNA gave approximately twice as much reduction as albumin alone, with a mean infarct volume of $18\pm22^3$ ($p<0.05$ vs. albumin, $p<0.01$ vs. saline).

Figure 39:
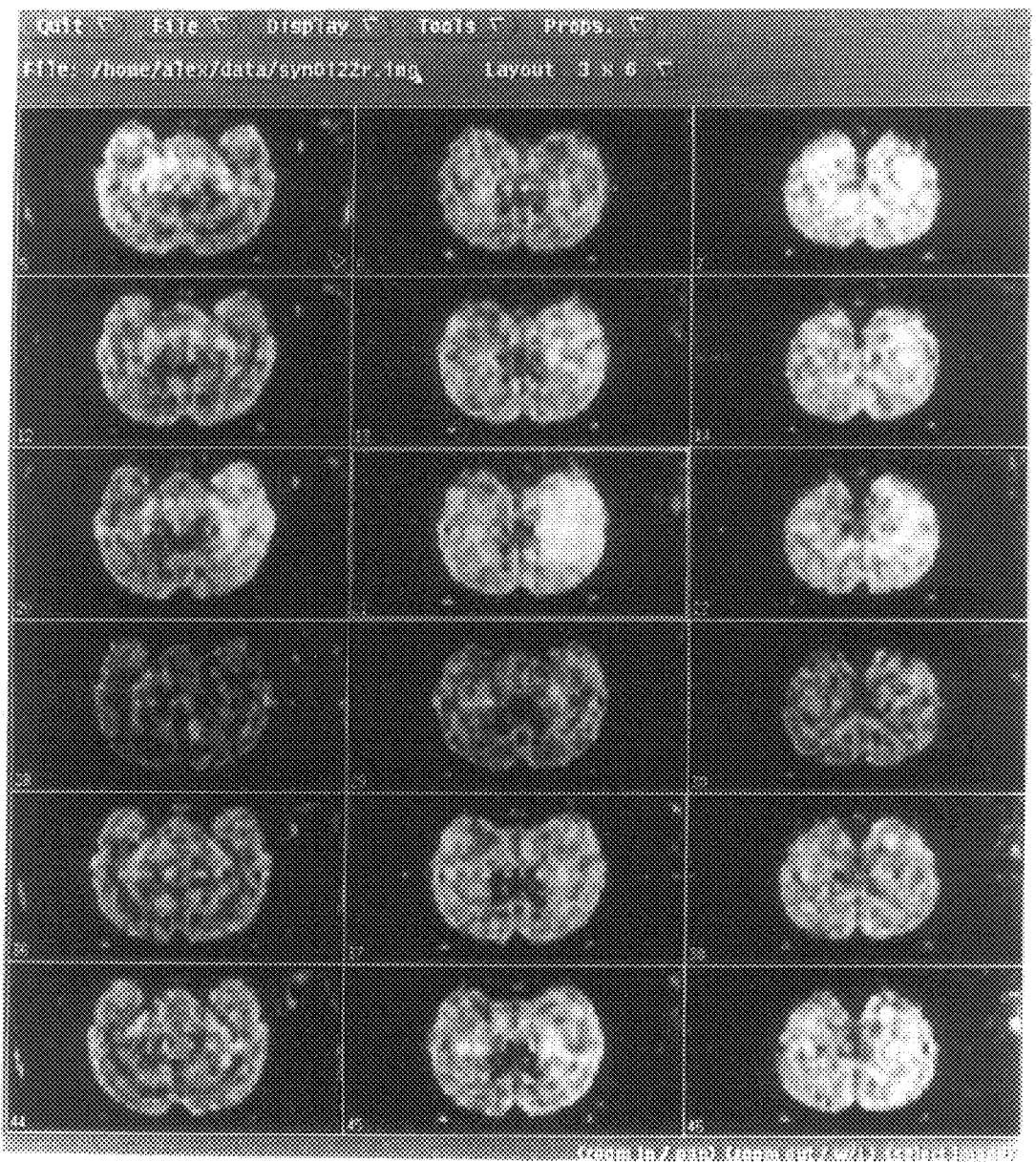
FIG. 39 is a diffusion-weighted magnetic resonance image of the rat brain during occlusion and reperfusion of the MCA.

In parallel with the histological analysis in the rat MCAO model, a magnetic resonance imaging study shows that when present at the onset of MCA occlusion, PNA slows the development of the diffusion-weighted imaging (DWI) hyperintensity during cerebral ischemia (FIG. 39). In addition, the protection offered by PNA against reperfusion injury is indicated by the rapid disappearance of DWI hyperintensity following reperfusion.

In addition to the results herein demonstrating protection for cerebral ischemia in mice, the compounds of the invention have shown efficacy in a rat model of stroke.

Referring to FIGS. 35a and 35b, representative coronal sections of the brain of a rat treated with normal saline (FIG. 35) and a rat treated with PNA (FIG. 36) reveal significant tissue necrosis in the saline group and significantly less necrosis in the PNA treated group. Rats were subjected to 2 hours of suture occlusion of the MCA, followed by 22 hours of reperfusion. Drug or saline was administered IV in a total dose of 1% of body weight (v/w), divided as follows: ½ the total dose was given 5 minutes before MCA occlusion; ¼ of the total dose was given five minutes before the suture was removed to allow reperfusion of the MCA; and the final ¼ of the total dose was given 2 hours after reperfusion. Brain sections were stained with TTC.

Figure 37A:
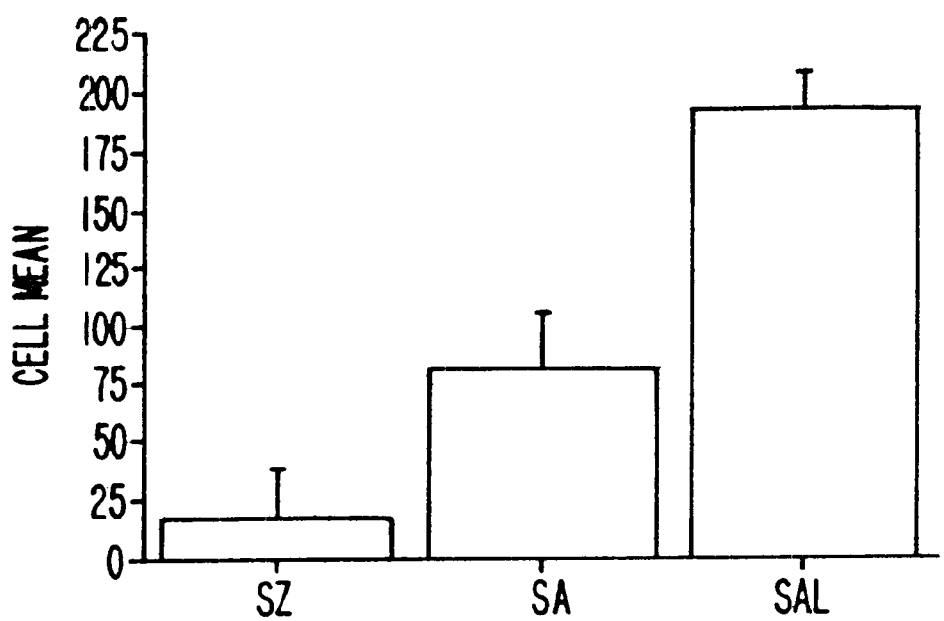
FIGS. 37A and 37B are histological analyses of infarct volume and percentage of infarction in rats following transient MCA occlusion and administration of saline, human serum albumin, and PNA.
Figure 37B:
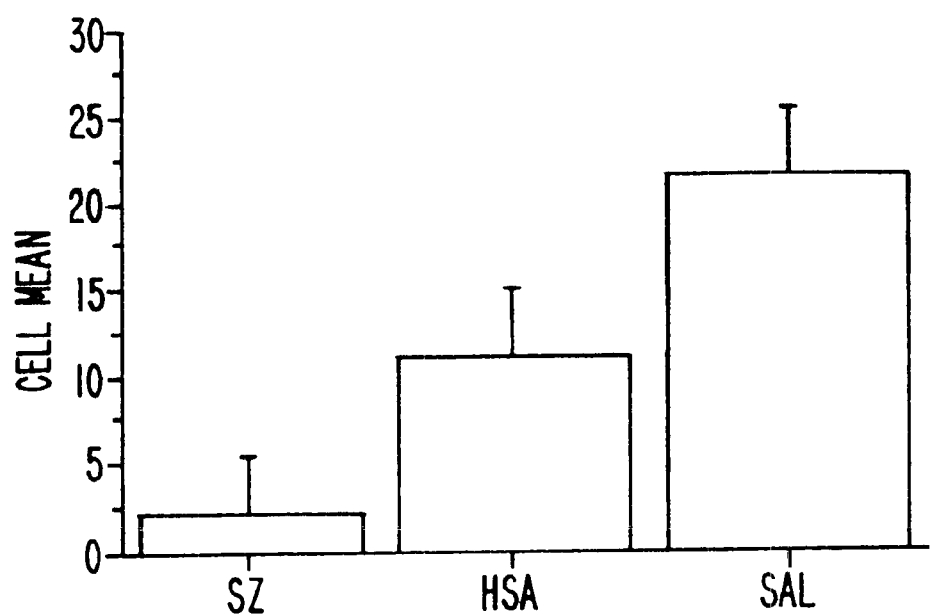

Referring to FIGS. 37A and 37B, histological analysis of infarct volume and percent infarction in rats subjected to transient MCA occlusion and treated with saline, human serum albumin (administered as a 25 g/dl solution, total dose 1% of body weight), or PNA shows protection of the brain tissue against ischemic/reperfusion injury. Animals treated with PNA showed approximately $2\pm36\%$ infarction; animals treated with albumin showed approximately $11\pm4\%$ infarction; and animals treated with saline showed approximately $22\pm4\%$ infarction. The fact albumin alone, has approximately 50% protective effort as compared to that of PNA, suggest the potential role of plasma expansion in stroke therapy. Therefore, PNA in hypertonic saline may further improve its efficiency in stroke therapy. The fact that albumin gave substantial protection in this experiment suggests a potentially beneficial role for plasma expansion in stroke therapy. The fact that PNA gave approximately twice as much protection as albumin suggests that polynitroxylated compounds may be useful in increasing efficacy of hypertonic or hyperoncotic therapies in stroke.

Figure 38:
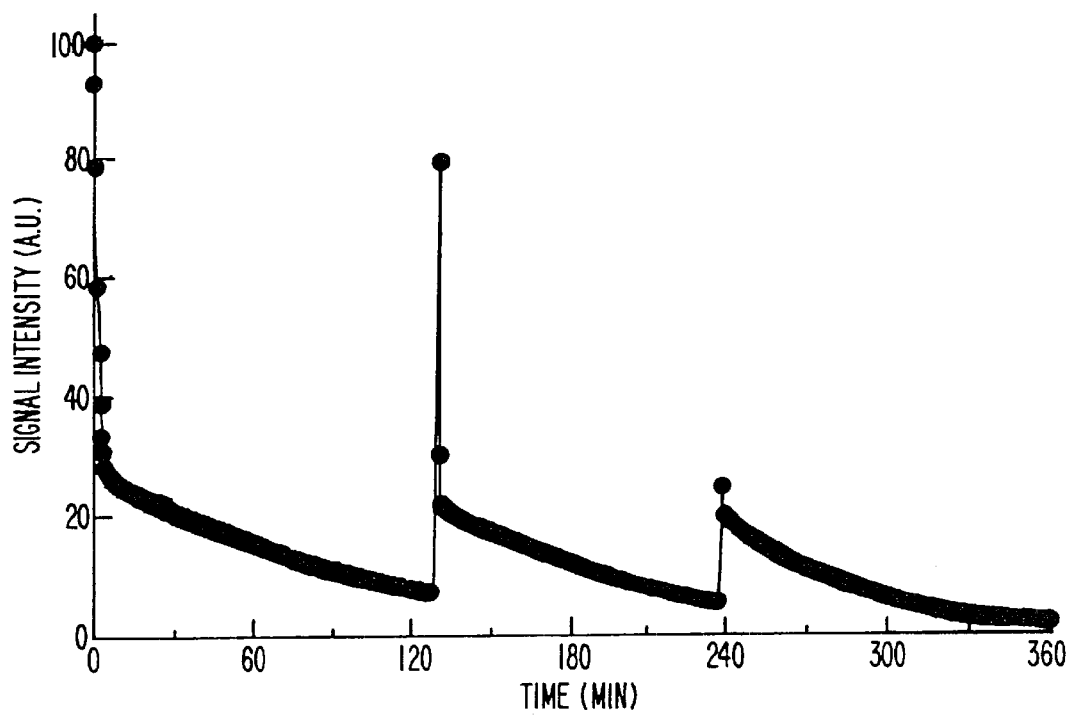
FIG. 38 is the spin density of rat blood measured as a function of time following three PNA injections at 2 hr intervals.

Referring to FIG. 38, due to the absence of significant quantities of naturally occurring paramagnetic species in vivo, the concentration of active PNA-bound nitroxide can be measured by in vivo EPR spectroscopy. In this experiment, a femoral arteriovenous shunt was created in the rat using PE50 polyethylene tubing. Part of the tubing was placed in the cavity of an EPR spectrometer, allowing measurement of the spin density of the blood flowing through the shunt. PNA was injected via a catheter in the contralateral femoral vein, and the spin density of the blood was measured as a function of time following PNA injection. Comparison with a standard curve (not shown) indicated that, with three injections at two-hour intervals, the EPR signal of PNA was maintained in the blood at levels in the range of 1–6 mM nitroxide for five hours.

Referring to FIG. 39, Diffusion-weighted magnetic resonance imaging (DWI) has been shown to indicate changes in the apparent diffusion coefficient (ADC) of water. In stroke, hyperintensity on DWI is thought to be a real-time indicator of the course of cerebral damage during ischemia. Perfusion-weighted imaging (PWI) was used in this experiment to confirm the occlusion and reperfusion of the MCA (images not shown). The figure shows DWI images made before, during, and after a 1.5-hour period of MCA occlusion in the rat, each row shows images made in three planes of the same brain. Row A shows that before MCA occlusion there is no DWI hyperintensity. Row B shows that 30 minutes after MCA occlusion, an area of DWI hyperintensity begins to appear, and is clearly defined at 1 hour of MCA occlusion (Row C). For comparison, in control images (not shown) a distinct DWI image typically appears within 5–10 minutes of MCA occlusion. Thus, when present before the onset of ischemia, PNA is capable of substantially slowing the progression of ischemic injury in the brain. Row D shows images made 8 minutes after reperfusion; the DWI image has essentially disappeared, indicating that the ADC change which occurred during ischemia resolved quickly upon reperfusion in the presence of PNA. For comparison, control images typically show progression of the DWI image after reperfusion, reflecting reperfusion injury. Rows E and F show images made, respectively, 1 hour and 2 hours post-reperfusion, confirming the absence of a DWI image. This animal was sacrificed 24 hours post-MCA occlusion and found histologically to have a small infarct in the basal ganglia, and no cortical infarct.

EXAMPLE TWELVE

Vasodilatory and Vasoneutral Formulation of Hemoglobin-based Red Cell Substitute (HRCS)

Figure 13:
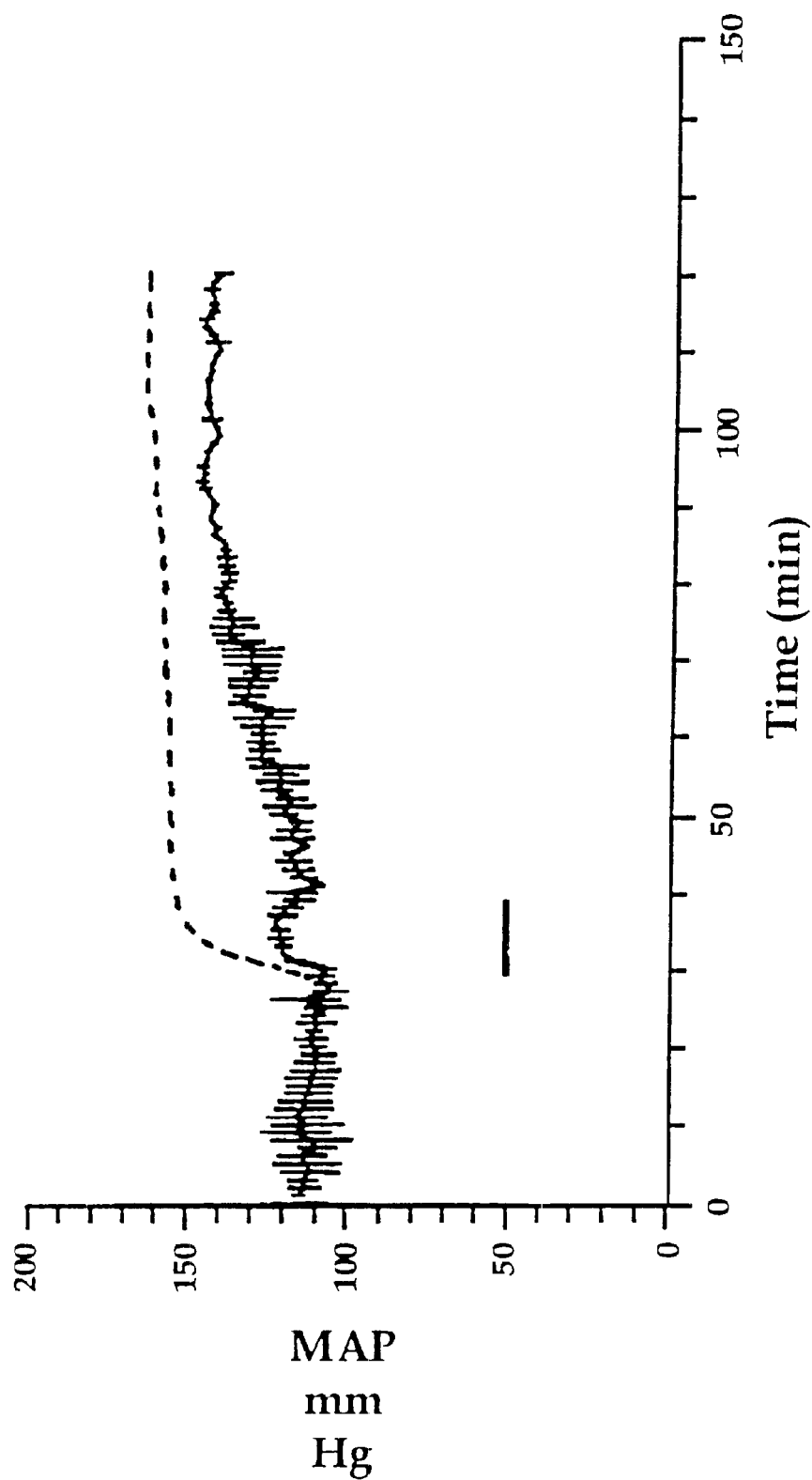
FIG. 13 shows the mean arterial pressure (MAP) response in a rat to intravenous infusion of 7.8 g/dl 10 v/v DBBF-Hb alone in Ringer's lactated solution (broken line) and 7.89/dl 10% v/v DBBF-Hb+polynitroxide albumin (PNA) 5 g/dl+ TPL 100 mM 10% v/v (solid line) in conscious rats. The rats were allowed to recover from surgery and anesthesia for approximately 7 days prior to study.
Figure 14:
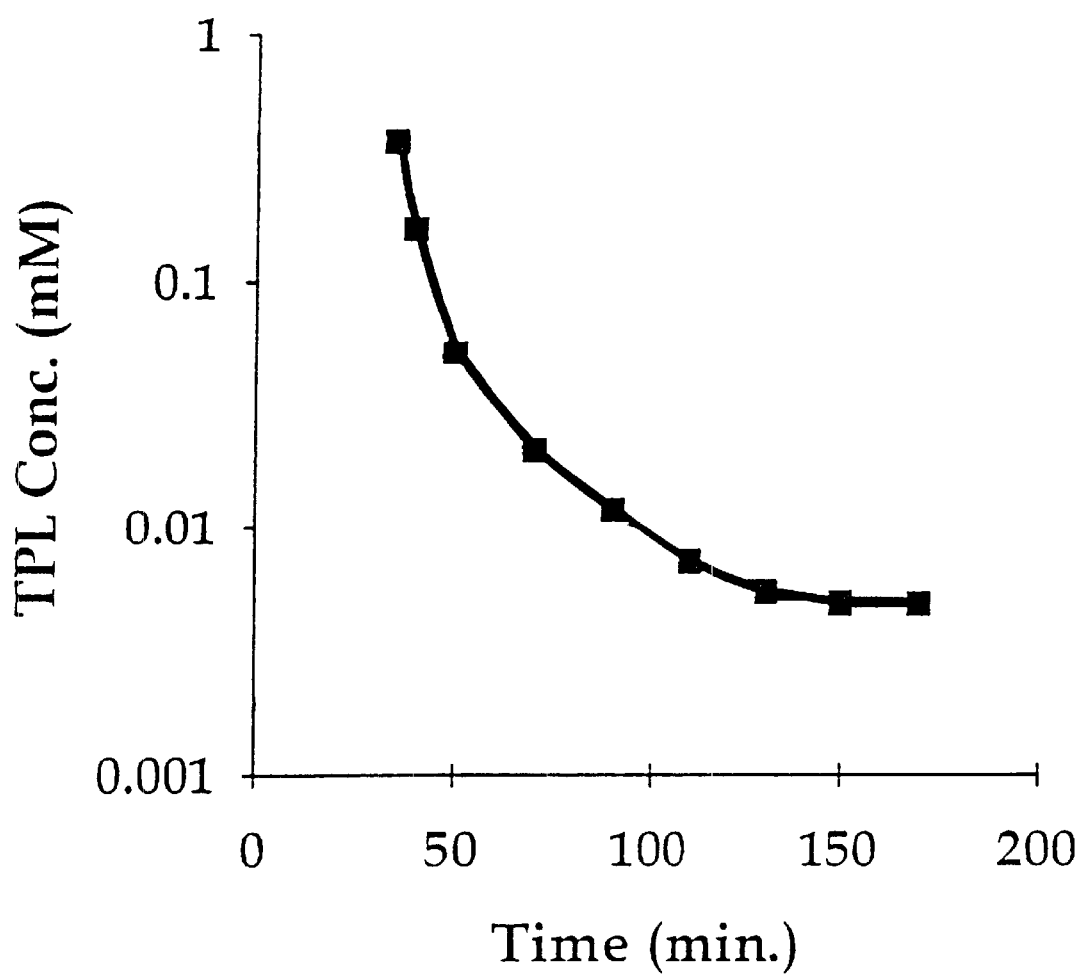
FIG. 14 is a plot showing time dependence of rat plasma concentrations of TPL after intravenous injections. Plasma samples were obtained from rats described in FIG. 13. TPL concentrations were determined from EPR spin density measurements.
Figure 29:
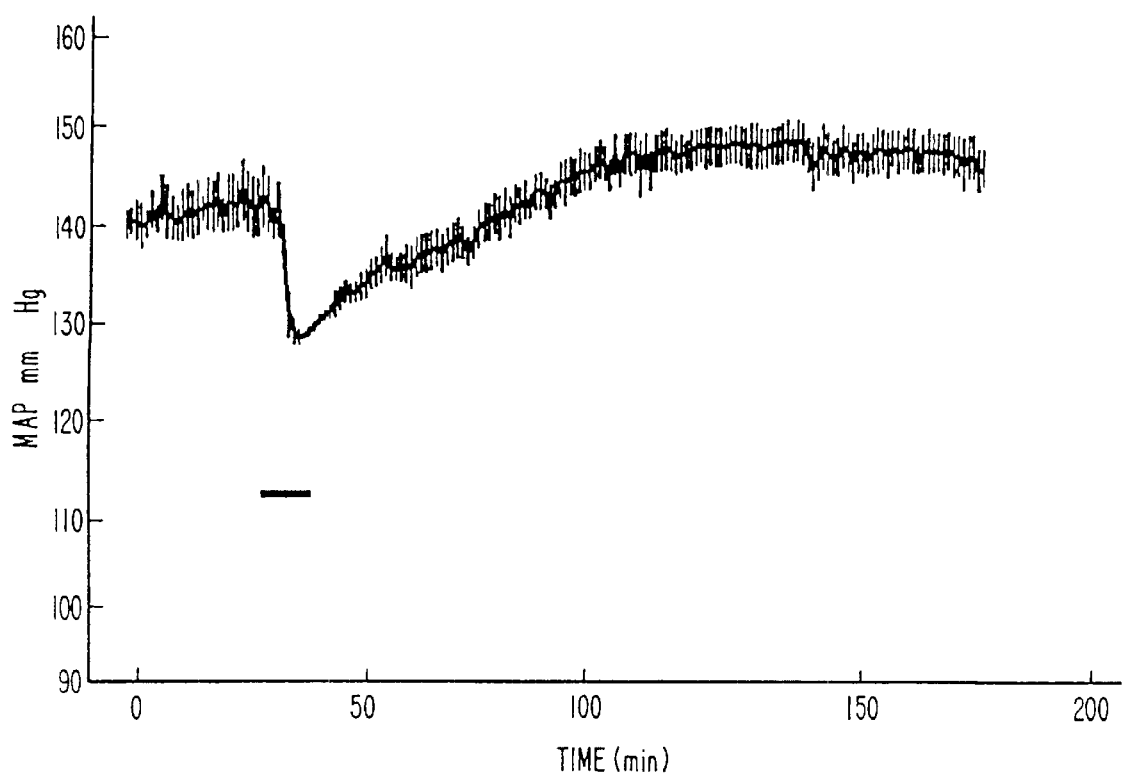
FIG. 29 shows the mean arterial pressure (MAP) response to intravenous infusion of 7.8 g/dl 10% v/v DBBF-Hb+PNA 7.5 g/dl+TPL 100 mM 10% v/v (n=4) in conscious rats. The rats were allowed to recover from surgery and anesthesia for approximately seven days prior to study.

FIG. 13 shows the effect of the compositions of this invention on the vasoconstrictive effect of hemoglobin-based oxygen carriers (HBOC), specifically DBBF-Hb. This vasoconstriction is demonstrated in conscious rat models by measuring the increase in mean arterial pressure (MAP) when a 10% v/v top load of this solution is infused. Referring to FIG. 13, the dotted line indicates the mean arterial pressure as a function of time following infusion of an HBOC. Pursuant to this invention, the same PNA and TPL solution used for radiation protection, ERI, and ischemia/reperfusion injury protection is shown to possess a broad range of enzyme mimic and radical detoxification functions. PNA or TPL, when injected alone with HBOC were found to have no antihypertensive effect. Further, PNA (5 g/dl) or TPL (100 mM) alone, 10% v/v top load, in conscious rats produces no significant vasodilatory effect. However, PNA (5%/dl)/TPL (100 mM) as top loaded at 10% v/v produces a significant and sustained vasodilatory effect was observed (FIG. 29). This vasodilatory effect coincides with the sustained plasma TPL levels in these rats (FIG. 14). In the absence of PNA, the plasma half-life of TPL in these rats is less than 60 seconds. Therefore, by mixing equal volumes of PNA (5 g/dl)/100 mM TPL with DBBF-Hb 7.8 g/dl and top load a 20% v/v in these rats a vasoneutral HRCS formulation is produced (FIG. 13). The hypotensive affect observed in FIG. 29 coincides with the sustained elevation of TPL (FIG. 14) in the vascular smooth muscles, which prevent the destruction of nitric oxide (i.e., endothelium derived relaxing factor (EDRF) by superoxide), thus enhancing the vasodilation and lowering the MAP in the rat (FIG. 29). In the case of a vasoneutral HRCS formulation (FIG. 13), the vasoconstrictive and vasodilatory activities of the HBOC and PNA/TPL cancelled each other's effect on the nitric oxide levels in vivo. Therefore, this vasoneutral formulation of HRCS is a significant improvement of the HBOC currently in clinical development, based on the global protection of free radical and oxidative stress.

EXAMPLE THIRTEEN

Inhibition of Lipid Oxidation

Oxidation of lipids is implicated in reperfusion injury and atherosclerosis as well as tissue injury to the brain and central nervous system. The nitroxide-labelled macromolecules of the invention are demonstrated to alleviate lipid oxidation.

Approximately 60 mL of heparinized blood was obtained from healthy, non-smoking men. Plasma LDL was prepared from EDTA (1 mg/mL)-anticoagulated venous blood after centrifugation of blood at 2000 g at 4° C. for 20 minutes. Blood, plasma, and LDL samples were processed in subdued light on ice to inhibit photoxidation of LDL antioxidants. LDL was isolated from plasma by rate zonal density gradient ultra-centrifugation. The density of plasma was raised to 1.3 g/mL by adding 5 g KBr to 10 mL of plasma. The KBr was dissolved in plasma by gentle mixing on a tipper for 10 to 15 minutes. Each KBr-plasma sample was layered underneath 23 mL of ice-cold 0.9% NaCl in an EasySeal polyallomer ultracentrifuge tube. The sealed tubes were centrifuged at 50,000 rpm (302,000 g) for 3 hours at 4° C. After centrifugation, the density gradients were fractionated by piercing the bottom of the tube with a needle and pumping Fluorinert into the tube at a rate of 5 mL/minute. The contents were collected from the top of the tube and diverted to a fraction collector. The first 12 mL of the gradient, containing very low density lipoproteins was discarded. Subsequently, six fractions of 1.2 mL each were collected. The dark yellow LDL peak was generally found in the fourth fraction. LDL was pooled from the peak fraction plus one fraction after the peak and two fractions before the peak. This LDL gave a single β-migrating band after agarose electrophoresis, indicating that the LDL was free from contamination by other lipoproteins. LDL samples were dialyzed against 6 L of HBSS buffer, three times before use. The isolated LDL samples were stored on ice in the dark. LDL protein content was determined by the Peterson-Lowry method with bovine serum albumin as a standard.

Lipid oxidation was measured by oxidation of LDL with hemin and $H_2O_2$. LDL 200 μg/mL was added to cuvette that contained 5 μmol hemin and 50 μmol $H_2O_2$. The final assay volume was 2 to 3 mL in HBSS buffer at pH 7.4. The assays were started by the addition of $H_2O_2$. In some experiments, PNA plus TPL was diluted in HBSS at 1:100, 1:1000 and 1:10,000. At various time points samples were removed and measurement of thiobarbituric acid reducing substances (TBARS) were measured. This was done by adding the sample to 500 μL of thiobarbituric acid reagent which included thiobarbituric acid, hydrochloric acid, trichloroacetic acid and distilled water. Butylated hydroxytoluene in DSMO was added at a final concentration of 0.1 mg/mL to inhibit spontaneous formation of TBARS during the subsequent heating step. After heating at 1000 for 15 minutes, the samples were cooled to room temperature and centrifuged at 10,000 g for 10 minutes. The clear supernatants were analyzed spectrophotometrically at 532 nm with an extinction coefficient of $1.56\times10^5$ $mol/L^{-1}$ $cm^{-1}$, and the results are presented as nanomoles TBARS per milligram LDL protein. FIGS. 35a–35d illustrate a time course of LDL oxidation in response to hemin $H_2O_2$. In these four separate experiments, the time to oxidation of LDL in the presence of PNA plus TPL at 1:100, 1:1,000, 1:10,000 is potently inhibited. The increase in optical density which reflects TBARS formation is blocked in experiments one and two by 1:100 and 1:10,000 PNA plus TPL.

EXAMPLE FOURTEEN

Inhibition of Leukocyte Activation

The interactions of leukocytes with endothelial cells and platelets are an indicator of the microcirculatory response to several adverse physiological conditions, ranging from localized and systemic ischemia/reperfusion injury, rejection of organ grafts, and the response to the organism to various oxidizing novae. See also Lehr et al., *PNAS*, 791:7688 (August 1984). The mediator role of reactive oxygen species has been documented in many in vitro and in vivo models and, as a consequence, antioxidants and radical scavengers have been applied to counteract leukocyte activation, aggregation, and adhesion to endothelium and the subsequent microcirculatory dysfunction. Using a dorsal skinfold chamber model in Syrian Golden hamsters to study the inhibitory effect of two different polynitroxylated carriers on cigarette smoke induced leukocyte rolling and adhesion to endothelial cells of arterioles and venules, as well as on the formation of leukocyte/platelet aggregates in the blood stream (Lehr et al., *PNAS* 91:7688, 1994), it is demonstrated that a HBOC (DBBF-crosslinked hemoglobin) had no effect on leukocyte activation when compared with saline-treated controls. However, polynitroxylated HBOC inhibited leukocyte activation essentially completely. It is known that albumin provides a degree of protection, as is observed in the following table, where at the dose used it inhibited activation. However, the Table shows that PNA also inhibited activation, and the HBOC and polynitroxyl-HBOC results shown in the Table predict that PNA will give better protection than albumin at lower protein concentrations. Polynitroxylated albumin and polynitroxylated, stabilized hemoglobin based oxygen carrier, as described above, effectively prevent detrimental leukocyte interactions with endothelial cells and platelets as shown in the following table.

| Time points | BASELINE | 15 MINUTES | 60 MINUTES |
|---|---|---|---|
| A. Human serum albumin, 25 g/dl | | | |
| arteriolar rolling (/mm) | 0.0 | 0.1 ± 0.2 | 0.1 ± 0.2 |
| arteriolar sticking (/mm$^2$) | 0.0 | 0.0 ± 0.0 | 0.0 ± 0.0 |
| venular rolling (%) | 4.9 ± 0.2 | 5.5 ± 0.9 | 6.9 ± 2.1 |
| venular sticking (/mm$^2$) | 0.0 ± 0.0 | 0.0 ± 0.0 | 0.0 ± 0.0 |
| aggregate formation (/30 sec) | 0.6 ± 0.7 | 0.7 ± 0.7 | 1.3 ± 1.1 |
| B. Polynitroxylated Albumin | | | |
| arteriolar rolling (/mm) | 0.0 | 0.0 ± 0.0 | 0.0 ± 0.0 |
| arteriolar sticking (/mm$^2$) | 0.0 | 0.0 ± 0.0 | 0.0 ± 0.0 |
| venular rolling (%) | 5.2 ± 0.8 | 5.8 ± 0.8 | 6.3 ± 1.8 |
| venular sticking (/mm$^2$) | 0.0 ± 0.0 | 0.0 ± 0.0 | 0.0 ± 0.0 |
| aggregate formation (/30 sec) | 0.4 ± 0.5 | 0.9 ± 0.7 | 1.2 ± 0.8 |
| C. Hemoglobin-based oxygen carrier (HBOC), DBBF-Hb | | | |
| arteriolar rolling (/mm) | 0.3 | 1.9 ± 2.0 | 3.8 ± 2.9 |
| arteriolar sticking (/mm$^2$) | 0.0 | 31.9 ± 26.4 | 42.0 ± 32.1 |
| venular rolling (%) | 5.8 ± 1.2 | 7.9 ± 2.8 | 9.2 ± 3.8 |
| venular sticking (/mm$^2$) | 0.0 ± 0.0 | 66.0 ± 43.2 | 101.5 ± 76.9 |
| aggregate formation (/30 sec) | 0.3 ± 0.5 | 3.0 ± 1.7 | 4.5 ± 2.6 |
| D. Polynitroxylated hemoglobin-based oxygen carrier | | | |
| arteriolar rolling (/mm) | 0.0 | 0.2 ± 0.3 | 0.1 ± 0.3 |
| arteriolar sticking (/mm$^2$) | 0.0 | 0.0 ± 0.0 | 1.3 ± 2.5 |
| venular rolling (%) | 5.0 ± 0.2 | 6.7 ± 1.0 | 6.3 ± 1.2 |
| venular sticking (/mm$^2$) | 0.0 ± 0.0 | 0.0 ± 0.0 | 0.0 ± 0.0 |
| aggregate formation (/30 sec) | 0.2 ± 0.2 | 1.9 ± 0.2 | 1.4 ± 0.3 |
| E. Isovolemic normal saline (control) | | | |
| arteriolar rolling (/mm) | 0.3 ± 0.2 | 2.5 ± 2.9 | 3.3 ± 2.0 |
| arteriolar sticking (/mm$^2$) | 0.0 ± 0.0 | 36.0 ± 27.6 | 40.0 ± 32.7 |
| venular rolling (%) | 4.5 ± 1.3 | 9.3 ± 1.7 | 10.3 ± 2.5 |
| venular sticking (/mm$^2$) | 0.0 ± 0.0 | 68.0 ± 43.8 | 90 ± 56.7 |
| aggregate formation (/30 sec) | 0.3 ± 0.3 | 3.5 ± 0.6 | 5.1 ± 1.1 |

EXAMPLE FIFTEEN

Topical Application to Skin Diseases, Particularly Psoriasis

Much research has been directed at the underlying causes of several diseases at the skin where free radical levels are elevated or where a free radical cascade is manifested in the dermis. In psoriasis, the causes are multi-faceted, however, the end effectors of the inflammatory process appear to be superoxide and other toxic oxygen radicals. Both skin cells and leukocytes have been reported to contribute to pathologic free radical levels in psoriasis. Dermal fibroblasts from both lesional and uninvolved skin of psoriatic patients have been reported to be higher (by 150% and 100% respectively) than normal controls. Er-Raki A, Charveron M, and Bonafe J L 1993. Increased superoxide anion production in dermal fibroblasts of psoriatic patients. Skin Pharmacol. 6:253–258. Psoriatic sera have been reported to increase superoxide generation by polymorphonuclear leukocytes (PMNs). Miyachi Y and Niwa Y 1983. Effects of psoriatic sera on the generation of oxygenintermediates by polymorphonuclear leukocytes. Arch. Dermatol. Res. 275:23–26. SOD levels in PMNs from psoriatic patients were reported to be significantly lower than normal. Dogan P, Soyuer U, and Tanrikulu G 1989. Superoxide dismutase and myeloperoxidase activity in polymorphonuclear leukocytes, and serum ceruloplasmin and copper levels, in psoriasis. Br. J. Dermatol. 120:239–244. Superoxide dismutase mRNA and immunoreactive enzyme have been reported to be increased in psoriatic skin, perhaps reflecting an attempt to compensate for elevated free radical levels. Kobayashi T, Matsumoto M, Iizuka H, Suzuki K, and Taniguchi N 1991. Superoxide dismutase in psoriasis, squamous cell carcinoma and basal cel epithelioma: an immunohistochemical study. Br. J. Dermatol. 124:555–559. Since free-radical scavengers have been reported to offer benefit in experimental studies on psoriasis, it follows that an agent which detoxifies free radicals may block the inflammatory process by preventing the cytotoxic effects of free radicals at the site of the psoriatic lesion. Haseloff R F, Blasio I E, Meffert H, and Ebert B. 1990. Hydroxyl radical scavenging and antipsoriatic activity of benzoic acid and derivatives. Free Radical Biol. Med. 9:111–115.

Using in vivo EPR spectroscopy in the mouse, the effectiveness of the compounds of the invention can be determined from an analysis of the pharmacokinetics of intradermal PNA and intravenous $^{15}$N-TPL.

A custom-built bridged loop-gap surface resonator, absorption microwave bridge was used for in vivo EPR spectroscopy at 1.25 GHz (L-band) in the mouse. This instrumentation was used to measure local TPL and PNA concentrations at specific sites on the body of the mouse. The anesthetized mouse was placed in a 'sandwich' of two templates which allowed it to be placed on the loop-gap surface resonator, absorption microwave bridge in either the supine position, for spectroscopy of the back of the head, or in the prone position for spectroscopy of the abdomen. A tail vein cannula was used for intravenous injection of $^{15}$N-TEMPOL; this injection site was remote from the resonator.

Figures 40A, 40B, 40C:
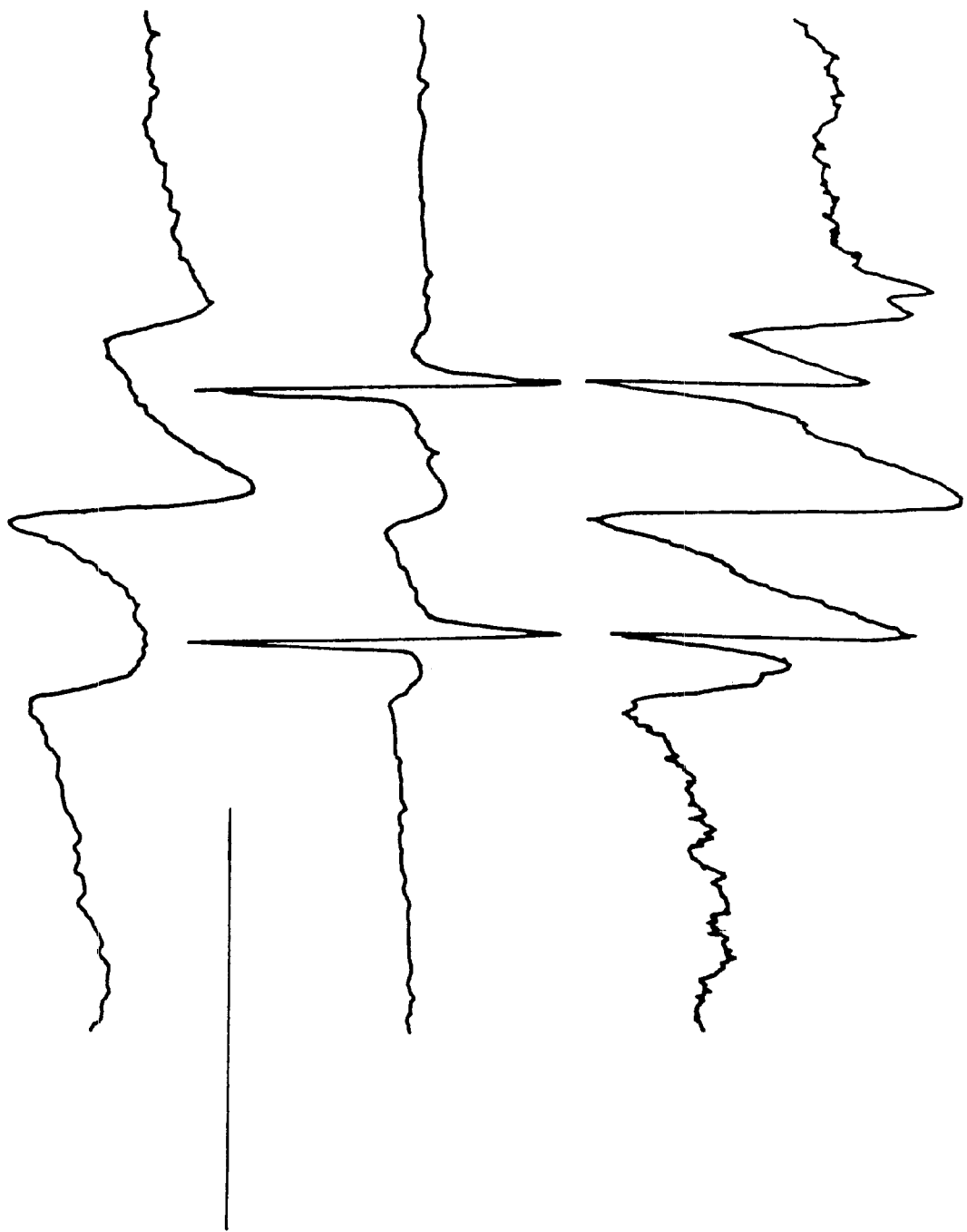
FIGS. 40A, 40B and 40C are EPR spectra of PNA and $^{15}$N-TPL in the skin on the back of an anesthetized mouse. 100 μl of PNA was injected intradermal at the back of an anesthetized mouse and the spectrum shown in (A) was recorded. $^{15}$N-TPL (1% v/w, 20 mg/ml) was then injected intravenously and the spectrum shown as (B) was recorded 1 min. later. Thirty minutes later the spectrum in (C) was recorded.

FIG. 40A shows the EPR spectrum of intradermally injected PNA (100 µl of a 10 g/dl PNA solution), measured at the site of injection on the animal's back.

FIG. 40B shows the composite spectrum of intradermal PNA and intravenous $^{15}$N-TPL, measured at the site of intradermal PNA injection on the animal's back. The broad, asymmetric central peak reflects only PNA concentration, while the sharp low-field peak to the left reflects only $^{15}$N-TPL concentration. The spectrum was made 1 minute after $^{15}$N-TPL was injected via the tail vein. The $^{15}$N-TPL dose was 1% of body weight (w/w) of a stock solution of $^{15}$N-TPL (20 mg/ml or 115 mM, in lactated Ringer's solution), giving a blood concentration of approximately 1.15 mM. FIG. 40B was recorded at approximately ⅕ of the instrument gain used in FIG. 40A in order to accommodate the $^{15}$N-TPL signal. FIG. 40C shows the EPR spectrum made 30 minutes after tail vein injection of $^{5}$N-TPL. The specific $^{15}$N-TPL and PNA peaks remain clearly distinguishable.

The pharmacokinetics of $^{15}$N-TPL at the site of intradermal PNA injection is shown in FIG. 41, a plot of the intensity of the $^{15}$N-TPL-specific peak vs. time. The $^{15}$N-TPL signal increased immediately after the tail vein injection, reaching a maximum at less than 2 minutes after injection, then decayed to a steady-state level. The residual steady-state level corresponds with 17% of the initial $^{15}$N-TPL concentration, assuming complete distribution in the total body water. The initial decay reflects the well-known reduction of TPL to the diamagnetic (EPR-silent) TPH. The persistence of the residual $^{15}$N-TPL signal is attributable to reoxidation of $^{15}$N-TPH to $^{15}$N-TPL by the intradermal PNA.

Figure 42B:
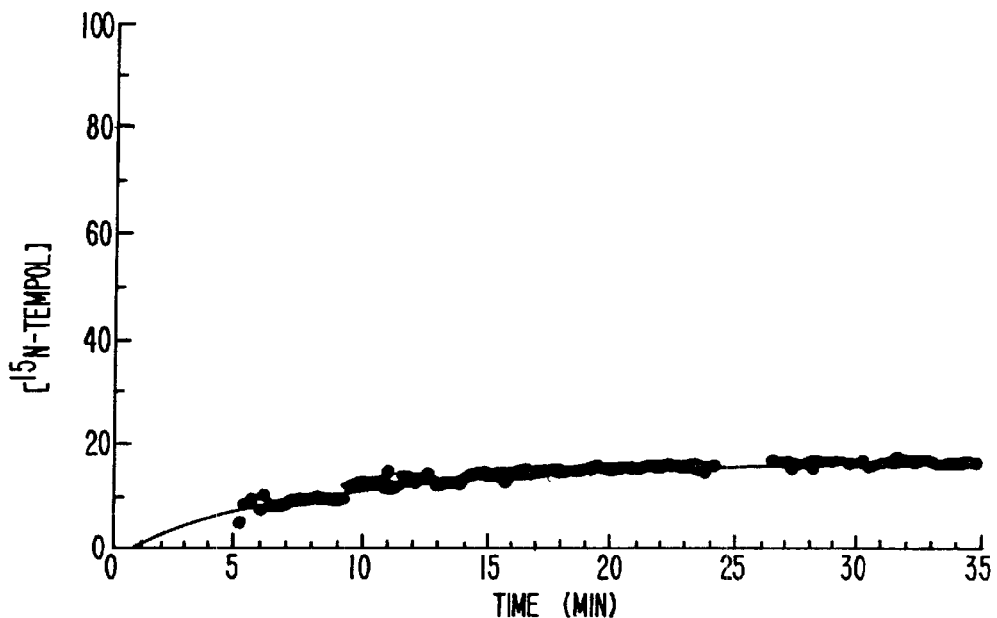

Referring to FIGS. 42A and 42B, to verify the intradermal reoxidation by PNA, the local pharmacokinetics of $^{15}$N-TPL were tested and showed a half-life of 30 seconds. In the absence of intradermal PNA, the decay of $^{15}$N-TPL to $^{15}$N-TPH is complete.

The presence of $^{15}$N-TPH in the skin is demonstrated by the intradermal injection of PNA at the belly. The intradermal PNA (100 µl, 10 g/dl) regenerates and sustains the $^{15}$N-TPL locally at the site of injection. The pharmacokinetics of the in vivo reoxidation of $^{15}$N-TPH is shown by comparing FIGS. 42A and 42B. A +5 minutes after the intradermal injection of PNA, the reoxidation of $^{15}$N-TPH is essentially complete.

EXAMPLE SIXTEEN

Free Radical Toxicity—Renal Injury

Figure 43:
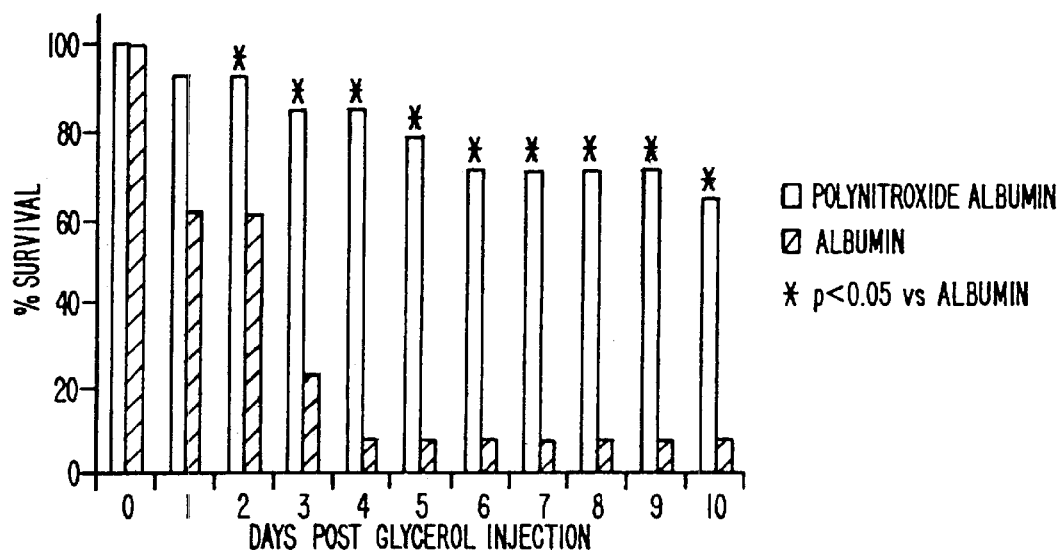
FIG. 43 shows the rate of survival over 10 days in an animal model of rhabdomyolysis involving injection of glycerol into a muscle and subsequent renal failure using polynitroxide albumin with TEMPOL and albumin as a control.

In an animal model of rhabdomyolysis, a bolus injection of glycerine into a major muscle causes heme-induced renal injury. Polynitroxide albumin is shown to reduce glycerol-induced renal injury in a survival study with albumin as a control. Male Sprague-Dawley rats weighing approximately 275 g were dehydrated overnight (16 h) after having baseline serum creatinine determined. On the following morning, 1.25 ml of either polynitroxide albumin and TEMPOL (10 g/dl) or albumin (10 g/dl) was given via tail vein injection. Immediately following the injection, an IM injection of glycerol (50w in water v/v, 10 ml/Kg) was given, ½ of the dose into each anterior thigh muscle. Two hours after the first injection another identical dose was given via tail vein injection. Referring to FIG. 43, for the next 10 days, survival and serum creatinine were monitored. At the end of this time, all rats tested had either suffered mortality or had showed signs of recovery (falling serum creatinine).

The particular examples set forth herein are instructional and should not be interpreted as limitations on the applications to which those of ordinary skill are able to apply this invention. Modifications and other uses are available to those skilled in the art which are encompassed within the spirit of the invention as defined by the scope of the following claims. All references and publications referred to above are specifically incorporated by reference.

What is claimed is:

1. A method to reduce the effect of free radical toxicity in a biological system comprising:

administering a therapeutically active amount of a membrane permeable first nitroxide wherein the first nitroxide is selected from the group consisting of 4,4-Dimethyl-3-oxazolinyloxy-(DOXYL), 2,2,5,5-Tetramethyl-1-pyrrolidinyloxy-(PROXYL), and 2,2,6,6-Tetramethyl-1-piperidinyloxy-(TEMPOL), having a nitroxyl group which donates an electron to a second nitroxide, and administering an amount of the second nitroxide to extend the reactivity of the first nitroxide, wherein the second nitroxide is a polynitroxide macromolecule and has a nitroxyl group which accepts an electron from the first nitroxide.

2. The method of claim 1 wherein the polynitroxide macromolecule is selected from the group consisting of polynitroxide, hydroxylethyl starch, polynitroxide dextran, polynitroxide hemoglobin, or polynitroxide immunoglobin.

* * * * *